US011390856B2

(12) United States Patent
Ybert et al.

(10) Patent No.: US 11,390,856 B2
(45) Date of Patent: Jul. 19, 2022

(54) VARIANTS OF FAMILY A DNA POLYMERASE AND USES THEREOF

(71) Applicant: DNA Script, Le Kremlin-Bicêtre (FR)

(72) Inventors: Thomas Ybert, Paris (FR); Elise Champion, Paris (FR); Omar Vivar, Le Kremlin-Bicêtre (FR); Ahmed Said, Le Kremlin-Bicêtre (FR)

(73) Assignee: DNA Script, Le Kremlin-Bicêtre (FR)

( * ) Notice: Subject to any disclaimer, the term of this patent is extended or adjusted under 35 U.S.C. 154(b) by 0 days.

(21) Appl. No.: 16/636,875

(22) PCT Filed: Aug. 6, 2018

(86) PCT No.: PCT/EP2018/071217
§ 371 (c)(1),
(2) Date: Feb. 5, 2020

(87) PCT Pub. No.: WO2019/030149
PCT Pub. Date: Feb. 14, 2019

(65) Prior Publication Data
US 2020/0370027 A1 Nov. 26, 2020

(30) Foreign Application Priority Data
Aug. 7, 2017 (EP) ..................... 17306052

(51) Int. Cl.
*C12N 9/12* (2006.01)

(52) U.S. Cl.
CPC .... *C12N 9/1252* (2013.01); *C12Y 207/07007* (2013.01)

(58) Field of Classification Search
None
See application file for complete search history.

(56) References Cited

U.S. PATENT DOCUMENTS

| | | | |
|---|---|---|---|
| 4,448,883 A | 5/1984 | Case | |
| 4,772,691 A | 9/1988 | Herman | |
| 5,436,143 A | 7/1995 | Hyman | |
| 5,516,664 A | 5/1996 | Hyman | |
| 5,602,000 A | 2/1997 | Hyman | |
| 5,656,745 A | 8/1997 | Bischofberger | |
| 5,744,595 A | 4/1998 | Srivastava | |
| 5,763,594 A | 6/1998 | Hiatt | |
| 5,808,045 A | 9/1998 | Hiatt | |
| 5,872,244 A | 2/1999 | Hiatt | |
| 5,917,031 A | 6/1999 | Miura | |
| 5,935,527 A | 8/1999 | Andrus | |
| 5,990,300 A | 11/1999 | Hiatt | |
| 6,214,987 B1 | 4/2001 | Hiatt | |
| 6,232,465 B1 | 5/2001 | Hiatt | |
| 6,623,929 B1 | 9/2003 | Densham | |
| 6,777,189 B2 | 8/2004 | Wei | |
| 7,057,026 B2 | 1/2006 | Barnes | |
| 7,078,499 B2 | 7/2006 | Odedra | |
| 7,125,671 B2 | 10/2006 | Sood | |
| 7,270,951 B1 | 9/2007 | Stemple | |
| 7,407,757 B2 | 8/2008 | Brenner | |
| 7,494,797 B2 | 2/2009 | Mueller | |
| 7,544,794 B1 | 6/2009 | Benner | |
| 7,939,259 B2 | 5/2011 | Kokoris | |
| 8,034,923 B1 | 10/2011 | Benner | |
| 8,212,020 B2 | 7/2012 | Benner | |
| 8,263,335 B2 | 9/2012 | Carr | |
| 8,674,086 B2 | 3/2014 | Liu | |
| 8,808,988 B2 | 8/2014 | Zhao | |
| 8,808,989 B1 | 8/2014 | Efcavitch | |
| 9,896,709 B2 | 2/2018 | Makarov | |
| 10,059,929 B2 | 8/2018 | Efcavitch | |
| 10,435,676 B2 | 10/2019 | Champion et al. | |
| 2006/0240439 A1* | 10/2006 | Smith | C12Q 1/6869 435/6.12 |
| 2014/0363851 A1 | 12/2014 | Efcavitch | |
| 2014/0363852 A1 | 12/2014 | Efcavitch | |
| 2016/0108382 A1 | 4/2016 | Efcavitch et al. | |
| 2018/0016609 A1 | 1/2018 | Chen et al. | |
| 2018/0023108 A1 | 1/2018 | Chen | |
| 2018/0274001 A1* | 9/2018 | Efcavitch | C12Y 207/07007 |
| 2018/0312820 A1* | 11/2018 | Pomerantz | C12Q 1/68 |
| 2020/0002690 A1 | 1/2020 | Ybert et al. | |

FOREIGN PATENT DOCUMENTS

| | | |
|---|---|---|
| WO | 2016064880 | 4/2016 |
| WO | 2016128731 | 8/2016 |
| WO | 2017/075421 | 5/2017 |
| WO | 2017216472 | 12/2017 |
| WO | 2018215803 | 11/2018 |

OTHER PUBLICATIONS

Zahn et al., Human DNA polymerase θ grasps the primer terminus to mediate DNA repair, Nature Structural Mol. Biol. 22, 2015, 304-11. (Year: 2015).*
Yousefzadeh et al., Mechanism of Suppression of Chromosomal Instability by DNA Polymerase POLQ, PLOS Genetics 10, 2014, e1004654. (Year: 2014).*
Zahn et al., Human DNA polymerase theta grasps the primer terminus to mediate DNA repair, Nature Struct. Mol. Biol. 22, 2015, 304-11. (Year: 2015).*
Patel et al., DNA polymerase active site is highly mutable: Evolutionary consequences, Proc. Natl. Acad. Sci. USA 97, 2000, 5095-100. (Year: 2000).*
Shultz et al., Taq DNA Polymerase Mutants and 2'-Modified Sugar Recognition, Biochemistry 54 , 2015, 5999-6008. (Year: 2015).*
Li et al., Crystal structures of open and closed forms of binary and ternary complexes of the large fragment of Thermus aquaticus DNA polymerase I, EMBO J. 17, 1998, 7514-25. (Year: 1998).*

(Continued)

*Primary Examiner* — Robert B Mondesi
*Assistant Examiner* — Todd M Epstein
(74) *Attorney, Agent, or Firm* — Bozicevic, Field & Francis LLP; Edward J. Baba

(57) ABSTRACT

The present invention relates to variant of Family A polymerases able to synthesize a nucleic acid fragment without template and to incorporate a reversible modified terminator nucleotide during the nucleic acid fragment synthesis. The present invention further relates to uses thereof for enzymatic synthesis of nucleic acid molecules.

2 Claims, 13 Drawing Sheets

Specification includes a Sequence Listing.

(56) References Cited

OTHER PUBLICATIONS

Uniprot, Accession No. O75417, 2016, www.uniprot.org. (Year: 2016).*
Song et al., Large-Scale de novo Oligonucleotide Synthesis for Whole-Genome Synthesis and Data Storage, Frontiers Bioeng. Biotechnol. 9, 2021, 689797. (Year: 2021).*
Accession No. A4PCE2, (2007).
Aoufouchi et al. (2000) "Two novel human and mouse DNA polymerases of the polX family," Nucleic Acids Research, 28(18): 3684-3693.
Arana et al. (2008) "Low-fidelity DNA synthesis by human DNA polymerase theta" Nucleic Acids Research 36(11): 3847-3856.
Beabealashvilli et al. (1986) "Nucleoside 5'-triphosphates modified at sugar residues as subsliates for calf thymus terminal deoxynucleotidyl transferase and for AMV reverse transcriptase," Biochim. Biophys. Acta., 868(2-3): 136-144.
Bentoila et al. (1995) "The two isoforms of mouse terminal deoxynucleotidyl transferase differ in both the ability to add N regions and subcellular localization," The EMBO Journal, 14(17): 4221-4229.
Boule et al. (1998) "High-level expression of murine terminal deoxynucleotidyl transferase in *Escherichia coli* grown at low temperature and overexpressing argU tRNA," Molecular Biotechnology, 10: 199-208.
Database EPO Proteins, (2016) "Sequence 8 from Patent WO2016128731", XP002779827.
Database UniProt, (2017) SubName: Full=DNA nucleotidylexotransferase isoform X1{EC0:0000313:RefSeq:XP_008057295.1}, XP002779838.
Delarue et al. (2002) "Crystal structures of a template-independent DNA polymerase: murine terminal deoxynucleotidyltransferase," The EMBO Journal, 21(3): 427-439.
Dominguez et al. (2000) "DNA polymerase mu (Pol □), homologous to TdT, could act as a DNA mutator in eukaryotic cells," The EMBO Journal, 19(17): 1731-1742.
Flickinger et al. (1992) "Differential incorporation of biotinylated nucleotides by terminal deoxynucleotidyl transferase," Nucleic Acids Research, 20(9): 2382.
Gouge et al. (2013) "Structures of intermediates along the catalytic cycle of terminal deoxynucleotidyltransferase dynamical aspects of the two-metal ion mechanism," J. Mol. Biol., 425: 4334-4352.
Hogg et al. (2012) "Promiscuous DNA synthesis by human DNA polymerase θ" Nucleic Acids Research 40(6): 2611-2622.
International Search Report from PCT International Application No. PCT/EP2018/071217 dated Feb. 14, 2019.
International Search Report from PCT International Application No. PCT/EP2019/050334 dated Feb. 22, 2019.
International Search Report from PCT International Application No. PCT/FR2017/051519 dated Jan. 18, 2018.
Koiwai et al. (1986) "Isolation and characterization of bovine and mouse terminal deoxynucleotidyltransferase cDNAS expressible in mammalian cells," Nucleic Acids Research, 14(14): 5777-5792.
Michelson et al. (1982) "Characterization of the homopolymer tailing reaction catalyzed by terminal deoxynucleotidyl transferase," J. Biol. Chem., 257(24): 14773-14782.
Motea et al. (2010) "Terminal deoxynucleotidyl transferase: The story of a misguided DNA polymerase," Biochim Biophys Acta, 1804(5): 1151-1166.
PIR Accession No. WXHU, published Dec. 4, 1986 (Year: 1986).
PIR Accession No. A23595, published Sep. 10, 1999 (Year: 1999).
PIR Accession No. S55786, published Oct. 27, 1995 (Year: 1995).
PIR Accession No. 151658, published Sep. 13, 1996 (Year: 1996).
Romain et al. (2009) "Conferring a template-dependent polymerase activity to terminal deoxynucleotidyltransferase by mutations in the Loop1 region," Nucleic Acids Research, 37(14): 4642-4656.
Schmitz et al. (1999) "Solid-phase enzymatic synthesis of oligonucleotides," Organic Lett., 1(11): 1729-1731.
Schott et al. (1984) "Single-step elongation of oligodeoxynucleotides using terminal deoxynucleotidyl transferase," Eur. J. Biochem., 143: 613-620.
Singapore Patent Office, Written Opinion in Singapore Patent Application No. 11201809961T (dated Apr. 24, 2020).
Troshchynsky et al. (2015) "Functional analyses of polymorphic variants of human terminal deoxynucleotidyl transferase," Genes and Immunity, 16: 388-398.
Ud-Dean, (2008) "A theoretical model for template-free synthesis of long DNA sequence," Syst. Synth. Biol., 2: 67-73.
Written Opinion from PCT International Application No. PCT/EP2018/071217 dated Feb. 14, 2019.
Written Opinion from PCT International Application No. PCT/FR2017/051519 dated Jan. 18, 2018.
Yamtich et al. (2010) "DNA polymerase family X: function, structure, and cellular roles," Biochim. Biophys. Acta., 1804(5): 1136-1150.
Yang et al. (1994) "Mutational analysis of residues in the nucleotide binding domain of human terminal deoxynucleotidyl transferase," Journal of Biological Chemistry, 269(16): 11859-11868.
Yang et al. (1995) "T-cell specific avian TdT: characterization of the cDNA and recombinant ezyme," Nucleic Acids Research, 23(11): 2041-2048.
Zahn et al. (2015) "Human DNA polymerase θ grasps the primer terminus to mediate DNA repair" Nat Struc Mol Biol 22(4): 304-3011.
Database Refseq (2016) Predicted: DNA polymerase theta isoform X1 [Rhinolophus sinicus], XP-002776331, 2 pages.
Shima et al. (2003) "Phenotype-Based Identification of Mouse Chromosome Instability Mutants" Genetics 163: 1031-1040.

* cited by examiner

3'-O-Azidomethyl 3'-O-Amino 3'-O-Allyl

SEQUENCE LISTING

<160> NUMBER OF SEQ ID NOS: 19

<210> SEQ ID NO 1
<211> LENGTH: 2590
<212> TYPE: PRT
<213> ORGANISM: artificial sequence
<220> FEATURE:
<223> OTHER INFORMATION: Human Pol theta

<400> SEQUENCE: 1

```
Met Asn Leu Leu Arg Arg Ser Gly Lys Arg Arg Ser Glu Ser Gly
1               5                   10                  15

Ser Asp Ser Phe Ser Gly Ser Gly Gly Asp Ser Ser Ala Ser Pro Gln
                20                  25                  30

Phe Leu Ser Gly Ser Val Leu Ser Pro Pro Gly Leu Gly Arg Cys
            35                  40                  45

Leu Lys Ala Ala Ala Ala Gly Glu Cys Lys Pro Thr Val Pro Asp Tyr
    50                  55                  60

Glu Arg Asp Lys Leu Leu Leu Ala Asn Trp Gly Leu Pro Lys Ala Val
65                  70                  75                  80

Leu Glu Lys Tyr His Ser Phe Gly Val Lys Lys Met Phe Glu Trp Gln
                85                  90                  95

Ala Glu Cys Leu Leu Leu Gly Gln Val Leu Glu Gly Lys Asn Leu Val
                100                 105                 110

Tyr Ser Ala Pro Thr Ser Ala Gly Lys Thr Leu Val Ala Glu Leu Leu
            115                 120                 125

Ile Leu Lys Arg Val Leu Glu Met Arg Lys Lys Ala Leu Phe Ile Leu
    130                 135                 140

Pro Phe Val Ser Val Ala Lys Glu Lys Lys Tyr Tyr Leu Gln Ser Leu
145                 150                 155                 160

Phe Gln Glu Val Gly Ile Lys Val Asp Gly Tyr Met Gly Ser Thr Ser
                165                 170                 175

Pro Ser Arg His Phe Ser Ser Leu Asp Ile Ala Val Cys Thr Ile Glu
            180                 185                 190

Arg Ala Asn Gly Leu Ile Asn Arg Leu Ile Glu Glu Asn Lys Met Asp
    195                 200                 205

Leu Leu Gly Met Val Val Val Asp Glu Leu His Met Leu Gly Asp Ser
    210                 215                 220

His Arg Gly Tyr Leu Leu Glu Leu Leu Leu Thr Lys Ile Cys Tyr Ile
225                 230                 235                 240

Thr Arg Lys Ser Ala Ser Cys Gln Ala Asp Leu Ala Ser Ser Leu Ser
                245                 250                 255

Asn Ala Val Gln Ile Val Gly Met Ser Ala Thr Leu Pro Asn Leu Glu
            260                 265                 270
```

```
Leu Val Ala Ser Trp Leu Asn Ala Glu Leu Tyr His Thr Asp Phe Arg
        275                 280                 285

Pro Val Pro Leu Leu Glu Ser Val Lys Val Gly Asn Ser Ile Tyr Asp
290                 295                 300

Ser Ser Met Lys Leu Val Arg Glu Phe Glu Pro Met Leu Gln Val Lys
305                 310                 315                 320

Gly Asp Glu Asp His Val Val Ser Leu Cys Tyr Glu Thr Ile Cys Asp
                325                 330                 335

Asn His Ser Val Leu Leu Phe Cys Pro Ser Lys Lys Trp Cys Glu Lys
                340                 345                 350

Leu Ala Asp Ile Ile Ala Arg Glu Phe Tyr Asn Leu His His Gln Ala
        355                 360                 365

Glu Gly Leu Val Lys Pro Ser Glu Cys Pro Val Ile Leu Glu Gln
        370                 375                 380

Lys Glu Leu Leu Glu Val Met Asp Gln Leu Arg Arg Leu Pro Ser Gly
385                 390                 395                 400

Leu Asp Ser Val Leu Gln Lys Thr Val Pro Trp Gly Val Ala Phe His
                405                 410                 415

His Ala Gly Leu Thr Phe Glu Glu Arg Asp Ile Ile Glu Gly Ala Phe
        420                 425                 430

Arg Gln Gly Leu Ile Arg Val Leu Ala Ala Thr Ser Thr Leu Ser Ser
        435                 440                 445

Gly Val Asn Leu Pro Ala Arg Arg Val Ile Ile Arg Thr Pro Ile Phe
        450                 455                 460

Gly Gly Arg Pro Leu Asp Ile Leu Thr Tyr Lys Gln Met Val Gly Arg
465                 470                 475                 480

Ala Gly Arg Lys Gly Val Asp Thr Val Gly Glu Ser Ile Leu Ile Cys
                485                 490                 495

Lys Asn Ser Glu Lys Ser Lys Gly Ile Ala Leu Leu Gln Gly Ser Leu
            500                 505                 510

Lys Pro Val Arg Ser Cys Leu Gln Arg Arg Glu Gly Glu Glu Val Thr
        515                 520                 525

Gly Ser Met Ile Arg Ala Ile Leu Glu Ile Ile Gly Gly Val Ala
        530                 535                 540

Ser Thr Ser Gln Asp Met His Thr Tyr Ala Ala Cys Thr Phe Leu Ala
545                 550                 555                 560

Ala Ser Met Lys Glu Gly Lys Gln Gly Ile Gln Arg Asn Gln Glu Ser
                565                 570                 575

Val Gln Leu Gly Ala Ile Glu Ala Cys Val Met Trp Leu Leu Glu Asn
            580                 585                 590

Glu Phe Ile Gln Ser Thr Glu Ala Ser Asp Gly Thr Glu Gly Lys Val
        595                 600                 605

Tyr His Pro Thr His Leu Gly Ser Ala Thr Leu Ser Ser Ser Leu Ser
        610                 615                 620

Pro Ala Asp Thr Leu Asp Ile Phe Ala Asp Leu Gln Arg Ala Met Lys
625                 630                 635                 640

Gly Phe Val Leu Glu Asn Asp Leu His Ile Leu Tyr Leu Val Thr Pro
                645                 650                 655

Met Phe Glu Asp Trp Thr Thr Ile Asp Trp Tyr Arg Phe Phe Cys Leu
                660                 665                 670

Trp Glu Lys Leu Pro Thr Ser Met Lys Arg Val Ala Glu Leu Val Gly
            675                 680                 685
```

-continued

Val Glu Glu Gly Phe Leu Ala Arg Cys Val Lys Gly Lys Val Val Ala
690                     695                 700

Arg Thr Glu Arg Gln His Arg Gln Met Ala Ile His Lys Arg Phe Phe
705                     710                 715                 720

Thr Ser Leu Val Leu Leu Asp Leu Ile Ser Glu Val Pro Leu Arg Glu
            725                 730                 735

Ile Asn Gln Lys Tyr Gly Cys Asn Arg Gly Gln Ile Gln Ser Leu Gln
            740                 745                 750

Gln Ser Ala Ala Val Tyr Ala Gly Met Ile Thr Val Phe Ser Asn Arg
            755                 760                 765

Leu Gly Trp His Asn Met Glu Leu Leu Leu Ser Gln Phe Gln Lys Arg
770                     775                 780

Leu Thr Phe Gly Ile Gln Arg Glu Leu Cys Asp Leu Val Arg Val Ser
785                     790                 795                 800

Leu Leu Asn Ala Gln Arg Ala Arg Val Leu Tyr Ala Ser Gly Phe His
            805                 810                 815

Thr Val Ala Asp Leu Ala Arg Ala Asn Ile Val Glu Val Glu Val Ile
            820                 825                 830

Leu Lys Asn Ala Val Pro Phe Lys Ser Ala Arg Lys Ala Val Asp Glu
            835                 840                 845

Glu Glu Glu Ala Val Glu Gly Arg Asn Met Arg Thr Ile Trp Val
850                     855                 860

Thr Gly Arg Lys Gly Leu Thr Glu Arg Glu Ala Ala Leu Ile Val
865                     870                 875                 880

Glu Glu Ala Arg Met Ile Leu Gln Gln Asp Leu Val Glu Met Gly Val
            885                 890                 895

Gln Trp Asn Pro Cys Ala Leu Leu His Ser Ser Thr Cys Ser Leu Thr
            900                 905                 910

His Ser Glu Ser Glu Val Lys Glu His Thr Phe Ile Ser Gln Thr Lys
            915                 920                 925

Ser Ser Tyr Lys Lys Leu Thr Ser Lys Asn Lys Ser Asn Thr Ile Phe
930                     935                 940

Ser Asp Ser Tyr Ile Lys His Ser Pro Asn Ile Val Gln Asp Leu Asn
945                     950                 955                 960

Lys Ser Arg Glu His Thr Ser Ser Phe Asn Cys Asn Phe Gln Asn Gly
            965                 970                 975

Asn Gln Glu His Gln Thr Cys Ser Ile Phe Arg Ala Arg Lys Arg Ala
            980                 985                 990

Ser Leu Asp Ile Asn Lys Glu Lys Pro Gly Ala Ser Gln Asn Glu Gly
            995                 1000                1005

Lys Thr Ser Asp Lys Lys Val Val Gln Thr Phe Ser Gln Lys Thr
    1010                1015                1020

Lys Lys Ala Pro Leu Asn Phe Asn Ser Glu Lys Met Ser Arg Ser
    1025                1030                1035

Phe Arg Ser Trp Lys Arg Arg Lys His Leu Lys Arg Ser Arg Asp
    1040                1045                1050

Ser Ser Pro Leu Lys Asp Ser Gly Ala Cys Arg Ile His Leu Gln
    1055                1060                1065

Gly Gln Thr Leu Ser Asn Pro Ser Leu Cys Glu Asp Pro Phe Thr
    1070                1075                1080

Leu Asp Glu Lys Lys Thr Glu Phe Arg Asn Ser Gly Pro Phe Ala
    1085                1090                1095

Lys Asn Val Ser Leu Ser Gly Lys Glu Lys Asp Asn Lys Thr Ser

```
                   1100                1105                1110
Phe Pro Leu Gln Ile Lys Gln Asn Cys Ser Trp Asn Ile Thr Leu
            1115                1120                1125
Thr Asn Asp Asn Phe Val Glu His Ile Val Thr Gly Ser Gln Ser
            1130                1135                1140
Lys Asn Val Thr Cys Gln Ala Thr Ser Val Val Ser Glu Lys Gly
            1145                1150                1155
Arg Gly Val Ala Val Glu Ala Lys Ile Asn Glu Val Leu Ile
            1160                1165                1170
Gln Asn Gly Ser Lys Asn Gln Asn Val Tyr Met Lys His His Asp
            1175                1180                1185
Ile His Pro Ile Asn Gln Tyr Leu Arg Lys Gln Ser His Glu Gln
            1190                1195                1200
Thr Ser Thr Ile Thr Lys Gln Lys Asn Ile Ile Glu Arg Gln Met
            1205                1210                1215
Pro Cys Glu Ala Val Ser Ser Tyr Ile Asn Arg Asp Ser Asn Val
            1220                1225                1230
Thr Ile Asn Cys Glu Arg Ile Lys Leu Asn Thr Glu Glu Asn Lys
            1235                1240                1245
Pro Ser His Phe Gln Ala Leu Gly Asp Asp Ile Ser Arg Thr Val
            1250                1255                1260
Ile Pro Ser Glu Val Leu Pro Ser Ala Gly Ala Phe Ser Lys Ser
            1265                1270                1275
Glu Gly Gln His Glu Asn Phe Leu Asn Ile Ser Arg Leu Gln Glu
            1280                1285                1290
Lys Thr Gly Thr Tyr Thr Thr Asn Lys Thr Lys Asn Asn His Val
            1295                1300                1305
Ser Asp Leu Gly Leu Val Leu Cys Asp Phe Glu Asp Ser Phe Tyr
            1310                1315                1320
Leu Asp Thr Gln Ser Glu Lys Ile Ile Gln Gln Met Ala Thr Glu
            1325                1330                1335
Asn Ala Lys Leu Gly Ala Lys Asp Thr Asn Leu Ala Ala Gly Ile
            1340                1345                1350
Met Gln Lys Ser Leu Val Gln Gln Asn Ser Met Asn Ser Phe Gln
            1355                1360                1365
Lys Glu Cys His Ile Pro Phe Pro Ala Glu Gln His Pro Leu Gly
            1370                1375                1380
Ala Thr Lys Ile Asp His Leu Asp Leu Lys Thr Val Gly Thr Met
            1385                1390                1395
Lys Gln Ser Ser Asp Ser His Gly Val Asp Ile Leu Thr Pro Glu
            1400                1405                1410
Ser Pro Ile Phe His Ser Pro Ile Leu Leu Glu Glu Asn Gly Leu
            1415                1420                1425
Phe Leu Lys Lys Asn Glu Val Ser Val Thr Asp Ser Gln Leu Asn
            1430                1435                1440
Ser Phe Leu Gln Gly Tyr Gln Thr Gln Glu Thr Val Lys Pro Val
            1445                1450                1455
Ile Leu Leu Ile Pro Gln Lys Arg Thr Pro Thr Gly Val Glu Gly
            1460                1465                1470
Glu Cys Leu Pro Val Pro Glu Thr Ser Leu Asn Met Ser Asp Ser
            1475                1480                1485
Leu Leu Phe Asp Ser Phe Ser Asp Asp Tyr Leu Val Lys Glu Gln
            1490                1495                1500
```

```
Leu Pro Asp Met Gln Met Lys Glu Pro Leu Pro Ser Glu Val Thr
1505                1510                1515

Ser Asn His Phe Ser Asp Ser Leu Cys Leu Gln Glu Asp Leu Ile
1520                1525                1530

Lys Lys Ser Asn Val Asn Glu Asn Gln Asp Thr His Gln Gln Leu
1535                1540                1545

Thr Cys Ser Asn Asp Glu Ser Ile Ile Phe Ser Glu Met Asp Ser
1550                1555                1560

Val Gln Met Val Glu Ala Leu Asp Asn Val Asp Ile Phe Pro Val
1565                1570                1575

Gln Glu Lys Asn His Thr Val Val Ser Pro Arg Ala Leu Glu Leu
1580                1585                1590

Ser Asp Pro Val Leu Asp Glu His His Gln Gly Asp Gln Asp Gly
1595                1600                1605

Gly Asp Gln Asp Glu Arg Ala Glu Lys Ser Lys Leu Thr Gly Thr
1610                1615                1620

Arg Gln Asn His Ser Phe Ile Trp Ser Gly Ala Ser Phe Asp Leu
1625                1630                1635

Ser Pro Gly Leu Gln Arg Ile Leu Asp Lys Val Ser Ser Pro Leu
1640                1645                1650

Glu Asn Glu Lys Leu Lys Ser Met Thr Ile Asn Phe Ser Ser Leu
1655                1660                1665

Asn Arg Lys Asn Thr Glu Leu Asn Glu Glu Gln Glu Val Ile Ser
1670                1675                1680

Asn Leu Glu Thr Lys Gln Val Gln Gly Ile Ser Phe Ser Ser Asn
1685                1690                1695

Asn Glu Val Lys Ser Lys Ile Glu Met Leu Glu Asn Asn Ala Asn
1700                1705                1710

His Asp Glu Thr Ser Ser Leu Leu Pro Arg Lys Glu Ser Asn Ile
1715                1720                1725

Val Asp Asp Asn Gly Leu Ile Pro Pro Thr Pro Ile Pro Thr Ser
1730                1735                1740

Ala Ser Lys Leu Thr Phe Pro Gly Ile Leu Glu Thr Pro Val Asn
1745                1750                1755

Pro Trp Lys Thr Asn Asn Val Leu Gln Pro Gly Glu Ser Tyr Leu
1760                1765                1770

Phe Gly Ser Pro Ser Asp Ile Lys Asn His Asp Leu Ser Pro Gly
1775                1780                1785

Ser Arg Asn Gly Phe Lys Asp Asn Ser Pro Ile Ser Asp Thr Ser
1790                1795                1800

Phe Ser Leu Gln Leu Ser Gln Asp Gly Leu Gln Leu Thr Pro Ala
1805                1810                1815

Ser Ser Ser Glu Ser Leu Ser Ile Ile Asp Val Ala Ser Asp
1820                1825                1830

Gln Asn Leu Phe Gln Thr Phe Ile Lys Glu Trp Arg Cys Lys Lys
1835                1840                1845

Arg Phe Ser Ile Ser Leu Ala Cys Glu Lys Ile Arg Ser Leu Thr
1850                1855                1860

Ser Ser Lys Thr Ala Thr Ile Gly Ser Arg Phe Lys Gln Ala Ser
1865                1870                1875

Ser Pro Gln Glu Ile Pro Ile Arg Asp Asp Gly Phe Pro Ile Lys
1880                1885                1890
```

Gly Cys Asp Asp Thr Leu Val Val Gly Leu Ala Val Cys Trp Gly
1895                 1900                1905

Gly Arg Asp Ala Tyr Tyr Phe Ser Leu Gln Lys Glu Gln Lys His
1910                 1915                1920

Ser Glu Ile Ser Ala Ser Leu Val Pro Pro Ser Leu Asp Pro Ser
1925                 1930                1935

Leu Thr Leu Lys Asp Arg Met Trp Tyr Leu Gln Ser Cys Leu Arg
1940                 1945                1950

Lys Glu Ser Asp Lys Glu Cys Ser Val Val Ile Tyr Asp Phe Ile
1955                 1960                1965

Gln Ser Tyr Lys Ile Leu Leu Leu Ser Cys Gly Ile Ser Leu Glu
1970                 1975                1980

Gln Ser Tyr Glu Asp Pro Lys Val Ala Cys Trp Leu Leu Asp Pro
1985                 1990                1995

Asp Ser Gln Glu Pro Thr Leu His Ser Ile Val Thr Ser Phe Leu
2000                 2005                2010

Pro His Glu Leu Pro Leu Leu Glu Gly Met Glu Thr Ser Gln Gly
2015                 2020                2025

Ile Gln Ser Leu Gly Leu Asn Ala Gly Ser Glu His Ser Gly Arg
2030                 2035                2040

Tyr Arg Ala Ser Val Glu Ser Ile Leu Ile Phe Asn Ser Met Asn
2045                 2050                2055

Gln Leu Asn Ser Leu Leu Gln Lys Glu Asn Leu Gln Asp Val Phe
2060                 2065                2070

Arg Lys Val Glu Met Pro Ser Gln Tyr Cys Leu Ala Leu Leu Glu
2075                 2080                2085

Leu Asn Gly Ile Gly Phe Ser Thr Ala Glu Cys Glu Ser Gln Lys
2090                 2095                2100

His Ile Met Gln Ala Lys Leu Asp Ala Ile Glu Thr Gln Ala Tyr
2105                 2110                2115

Gln Leu Ala Gly His Ser Phe Ser Phe Thr Ser Ser Asp Asp Ile
2120                 2125                2130

Ala Glu Val Leu Phe Leu Glu Leu Lys Leu Pro Pro Asn Arg Glu
2135                 2140                2145

Met Lys Asn Gln Gly Ser Lys Lys Thr Leu Gly Ser Thr Arg Arg
2150                 2155                2160

Gly Ile Asp Asn Gly Arg Lys Leu Arg Leu Gly Arg Gln Phe Ser
2165                 2170                2175

Thr Ser Lys Asp Val Leu Asn Lys Leu Lys Ala Leu His Pro Leu
2180                 2185                2190

Pro Gly Leu Ile Leu Glu Trp Arg Arg Ile Thr Asn Ala Ile Thr
2195                 2200                2205

Lys Val Val Phe Pro Leu Gln Arg Glu Lys Cys Leu Asn Pro Phe
2210                 2215                2220

Leu Gly Met Glu Arg Ile Tyr Pro Val Ser Gln Ser His Thr Ala
2225                 2230                2235

Thr Gly Arg Ile Thr Phe Thr Glu Pro Asn Ile Gln Asn Val Pro
2240                 2245                2250

Arg Asp Phe Glu Ile Lys Met Pro Thr Leu Val Gly Glu Ser Pro
2255                 2260                2265

Pro Ser Gln Ala Val Gly Lys Gly Leu Leu Pro Met Gly Arg Gly
2270                 2275                2280

Lys Tyr Lys Lys Gly Phe Ser Val Asn Pro Arg Cys Gln Ala Gln

```
            2285                2290                2295

Met Glu Glu Arg Ala Ala Asp Arg Gly Met Pro Phe Ser Ile Ser
    2300                2305                2310

Met Arg His Ala Phe Val Pro Phe Pro Gly Gly Ser Ile Leu Ala
    2315                2320                2325

Ala Asp Tyr Ser Gln Leu Glu Leu Arg Ile Leu Ala His Leu Ser
    2330                2335                2340

His Asp Arg Arg Leu Ile Gln Val Leu Asn Thr Gly Ala Asp Val
    2345                2350                2355

Phe Arg Ser Ile Ala Ala Glu Trp Lys Met Ile Glu Pro Glu Ser
    2360                2365                2370

Val Gly Asp Asp Leu Arg Gln Gln Ala Lys Gln Ile Cys Tyr Gly
    2375                2380                2385

Ile Ile Tyr Gly Met Gly Ala Lys Ser Leu Gly Glu Gln Met Gly
    2390                2395                2400

Ile Lys Glu Asn Asp Ala Ala Cys Tyr Ile Asp Ser Phe Lys Ser
    2405                2410                2415

Arg Tyr Thr Gly Ile Asn Gln Phe Met Thr Glu Thr Val Lys Asn
    2420                2425                2430

Cys Lys Arg Asp Gly Phe Val Gln Thr Ile Leu Gly Arg Arg Arg
    2435                2440                2445

Tyr Leu Pro Gly Ile Lys Asp Asn Asn Pro Tyr Arg Lys Ala His
    2450                2455                2460

Ala Glu Arg Gln Ala Ile Asn Thr Ile Val Gln Gly Ser Ala Ala
    2465                2470                2475

Asp Ile Val Lys Ile Ala Thr Val Asn Ile Gln Lys Gln Leu Glu
    2480                2485                2490

Thr Phe His Ser Thr Phe Lys Ser His Gly His Arg Glu Gly Met
    2495                2500                2505

Leu Gln Ser Asp Gln Thr Gly Leu Ser Arg Lys Arg Lys Leu Gln
    2510                2515                2520

Gly Met Phe Cys Pro Ile Arg Gly Gly Phe Phe Ile Leu Gln Leu
    2525                2530                2535

His Asp Glu Leu Leu Tyr Glu Val Ala Glu Glu Asp Val Val Gln
    2540                2545                2550

Val Ala Gln Ile Val Lys Asn Glu Met Glu Ser Ala Val Lys Leu
    2555                2560                2565

Ser Val Lys Leu Lys Val Lys Val Lys Ile Gly Ala Ser Trp Gly
    2570                2575                2580

Glu Leu Lys Asp Phe Asp Val
    2585                2590

<210> SEQ ID NO 2
<211> LENGTH: 799
<212> TYPE: PRT
<213> ORGANISM: artificial sequence
<220> FEATURE:
<223> OTHER INFORMATION: pol Theta polymerase domain

<400> SEQUENCE: 2

Gly Phe Lys Asp Asn Ser Pro Ile Ser Asp Thr Ser Phe Ser Leu Gln
1               5                   10                  15

Leu Ser Gln Asp Gly Leu Gln Leu Thr Pro Ala Ser Ser Ser Ser Glu
                20                  25                  30

Ser Leu Ser Ile Ile Asp Val Ala Ser Asp Gln Asn Leu Phe Gln Thr
```

```
                35                  40                  45
Phe Ile Lys Glu Trp Arg Cys Lys Lys Arg Phe Ser Ile Ser Leu Ala
 50                  55                  60

Cys Glu Lys Ile Arg Ser Leu Thr Ser Ser Lys Thr Ala Thr Ile Gly
 65                  70                  75                  80

Ser Arg Phe Lys Gln Ala Ser Ser Pro Gln Glu Ile Pro Ile Arg Asp
                 85                  90                  95

Asp Gly Phe Pro Ile Lys Gly Cys Asp Asp Thr Leu Val Val Gly Leu
                100                 105                 110

Ala Val Cys Trp Gly Gly Arg Asp Ala Tyr Tyr Phe Ser Leu Gln Lys
            115                 120                 125

Glu Gln Lys His Ser Glu Ile Ser Ala Ser Leu Val Pro Pro Ser Leu
        130                 135                 140

Asp Pro Ser Leu Thr Leu Lys Asp Arg Met Trp Tyr Leu Gln Ser Cys
145                 150                 155                 160

Leu Arg Lys Glu Ser Asp Lys Glu Cys Ser Val Val Ile Tyr Asp Phe
                165                 170                 175

Ile Gln Ser Tyr Lys Ile Leu Leu Ser Cys Gly Ile Ser Leu Glu
            180                 185                 190

Gln Ser Tyr Glu Asp Pro Lys Val Ala Cys Trp Leu Asp Pro Asp
        195                 200                 205

Ser Gln Glu Pro Thr Leu His Ser Ile Val Thr Ser Phe Leu Pro His
210                 215                 220

Glu Leu Pro Leu Leu Glu Gly Met Glu Thr Ser Gln Gly Ile Gln Ser
225                 230                 235                 240

Leu Gly Leu Asn Ala Gly Ser Glu His Ser Gly Arg Tyr Arg Ala Ser
                245                 250                 255

Val Glu Ser Ile Leu Ile Phe Asn Ser Met Asn Gln Leu Asn Ser Leu
            260                 265                 270

Leu Gln Lys Glu Asn Leu Gln Asp Val Phe Arg Lys Val Glu Met Pro
        275                 280                 285

Ser Gln Tyr Cys Leu Ala Leu Leu Glu Leu Asn Gly Ile Gly Phe Ser
290                 295                 300

Thr Ala Glu Cys Glu Ser Gln Lys His Ile Met Gln Ala Lys Leu Asp
305                 310                 315                 320

Ala Ile Glu Thr Gln Ala Tyr Gln Leu Ala Gly His Ser Phe Ser Phe
                325                 330                 335

Thr Ser Ser Asp Asp Ile Ala Glu Val Leu Phe Leu Glu Leu Lys Leu
            340                 345                 350

Pro Pro Asn Arg Glu Met Lys Asn Gln Gly Ser Lys Lys Thr Leu Gly
        355                 360                 365

Ser Thr Arg Arg Gly Ile Asp Asn Gly Arg Lys Leu Arg Leu Gly Arg
370                 375                 380

Gln Phe Ser Thr Ser Lys Asp Val Leu Asn Lys Leu Lys Ala Leu His
385                 390                 395                 400

Pro Leu Pro Gly Leu Ile Leu Glu Trp Arg Arg Ile Thr Asn Ala Ile
                405                 410                 415

Thr Lys Val Val Phe Pro Leu Gln Arg Glu Lys Cys Leu Asn Pro Phe
            420                 425                 430

Leu Gly Met Glu Arg Ile Tyr Pro Val Ser Gln Ser His Thr Ala Thr
        435                 440                 445

Gly Arg Ile Thr Phe Thr Glu Pro Asn Ile Gln Asn Val Pro Arg Asp
450                 455                 460
```

```
Phe Glu Ile Lys Met Pro Thr Leu Val Gly Glu Ser Pro Pro Ser Gln
465                 470                 475                 480

Ala Val Gly Lys Gly Leu Leu Pro Met Gly Arg Gly Lys Tyr Lys Lys
            485                 490                 495

Gly Phe Ser Val Asn Pro Arg Cys Gln Ala Gln Met Glu Glu Arg Ala
        500                 505                 510

Ala Asp Arg Gly Met Pro Phe Ser Ile Ser Met Arg His Ala Phe Val
    515                 520                 525

Pro Phe Pro Gly Gly Ser Ile Leu Ala Ala Asp Tyr Ser Gln Leu Glu
530                 535                 540

Leu Arg Ile Leu Ala His Leu Ser His Asp Arg Arg Leu Ile Gln Val
545                 550                 555                 560

Leu Asn Thr Gly Ala Asp Val Phe Arg Ser Ile Ala Ala Glu Trp Lys
            565                 570                 575

Met Ile Glu Pro Glu Ser Val Gly Asp Asp Leu Arg Gln Gln Ala Lys
        580                 585                 590

Gln Ile Cys Tyr Gly Ile Ile Tyr Gly Met Gly Ala Lys Ser Leu Gly
    595                 600                 605

Glu Gln Met Gly Ile Lys Glu Asn Asp Ala Ala Cys Tyr Ile Asp Ser
610                 615                 620

Phe Lys Ser Arg Tyr Thr Gly Ile Asn Gln Phe Met Thr Glu Thr Val
625                 630                 635                 640

Lys Asn Cys Lys Arg Asp Gly Phe Val Gln Thr Ile Leu Gly Arg Arg
            645                 650                 655

Arg Tyr Leu Pro Gly Ile Lys Asp Asn Asn Pro Tyr Arg Lys Ala His
        660                 665                 670

Ala Glu Arg Gln Ala Ile Asn Thr Ile Val Gln Gly Ser Ala Ala Asp
    675                 680                 685

Ile Val Lys Ile Ala Thr Val Asn Ile Gln Lys Gln Leu Glu Thr Phe
690                 695                 700

His Ser Thr Phe Lys Ser His Gly His Arg Glu Gly Met Leu Gln Ser
705                 710                 715                 720

Asp Gln Thr Gly Leu Ser Arg Lys Arg Lys Leu Gln Gly Met Phe Cys
            725                 730                 735

Pro Ile Arg Gly Gly Phe Phe Ile Leu Gln Leu His Asp Glu Leu Leu
        740                 745                 750

Tyr Glu Val Ala Glu Glu Asp Val Gln Val Ala Gln Ile Val Lys
    755                 760                 765

Asn Glu Met Glu Ser Ala Val Lys Leu Ser Val Lys Leu Lys Val Lys
770                 775                 780

Val Lys Ile Gly Ala Ser Trp Gly Glu Leu Lys Asp Phe Asp Val
785                 790                 795

<210> SEQ ID NO 3
<211> LENGTH: 10
<212> TYPE: PRT
<213> ORGANISM: artificial sequence
<220> FEATURE:
<223> OTHER INFORMATION: fragment of Pol theta

<400> SEQUENCE: 3

Asp Tyr Ser Gln Leu Glu Leu Arg Ile Leu
1               5                   10

<210> SEQ ID NO 4
```

```
<211> LENGTH: 8
<212> TYPE: PRT
<213> ORGANISM: artificial sequence
<220> FEATURE:
<223> OTHER INFORMATION: fragment of Pol Theta

<400> SEQUENCE: 4

Pro Gly Gly Ser Ile Leu Ala Ala
1               5

<210> SEQ ID NO 5
<211> LENGTH: 16
<212> TYPE: PRT
<213> ORGANISM: artificial sequence
<220> FEATURE:
<223> OTHER INFORMATION: fragment of Pol Theta

<400> SEQUENCE: 5

Asp Asp Leu Arg Gln Gln Ala Lys Gln Ile Cys Tyr Gly Ile Ile Tyr
1               5                   10                  15

<210> SEQ ID NO 6
<211> LENGTH: 6
<212> TYPE: PRT
<213> ORGANISM: artificial sequence
<220> FEATURE:
<223> OTHER INFORMATION: fragment of Pol Theta

<400> SEQUENCE: 6

Glu Trp Arg Arg Ile Thr
1               5

<210> SEQ ID NO 7
<211> LENGTH: 20
<212> TYPE: DNA
<213> ORGANISM: artificial sequence
<220> FEATURE:
<223> OTHER INFORMATION: synthetic sequence

<400> SEQUENCE: 7
taatacgact cactataggg                                              20

<210> SEQ ID NO 8
<211> LENGTH: 19
<212> TYPE: DNA
<213> ORGANISM: artificial sequence
<220> FEATURE:
<223> OTHER INFORMATION: synthetic sequence

<400> SEQUENCE: 8
gctagttatt gctcagcgg                                               19

<210> SEQ ID NO 9
<211> LENGTH: 18
<212> TYPE: DNA
<213> ORGANISM: artificial sequence
<220> FEATURE:
<223> OTHER INFORMATION: synthetic sequence

<400> SEQUENCE: 9
aaaaaaaaaa aaaagggg                                                18

<210> SEQ ID NO 10
<211> LENGTH: 2590
<212> TYPE: PRT
<213> ORGANISM: Homo sapiens
```

<400> SEQUENCE: 10

```
Met Asn Leu Leu Arg Arg Ser Gly Lys Arg Arg Ser Glu Ser Gly
1               5                   10                  15

Ser Asp Ser Phe Ser Gly Ser Gly Gly Asp Ser Ser Ala Ser Pro Gln
            20                  25                  30

Phe Leu Ser Gly Ser Val Leu Ser Pro Pro Gly Leu Gly Arg Cys
            35                  40                  45

Leu Lys Ala Ala Ala Gly Glu Cys Lys Pro Thr Val Pro Asp Tyr
50                  55                  60

Glu Arg Asp Lys Leu Leu Leu Ala Asn Trp Gly Leu Pro Lys Ala Val
65                  70                  75                  80

Leu Glu Lys Tyr His Ser Phe Gly Val Lys Met Phe Glu Trp Gln
                85                  90                  95

Ala Glu Cys Leu Leu Leu Gly Gln Val Leu Glu Gly Lys Asn Leu Val
            100                 105                 110

Tyr Ser Ala Pro Thr Ser Ala Gly Lys Thr Leu Val Ala Glu Leu Leu
            115                 120                 125

Ile Leu Lys Arg Val Leu Glu Met Arg Lys Lys Ala Leu Phe Ile Leu
130                 135                 140

Pro Phe Val Ser Val Ala Lys Glu Lys Lys Tyr Tyr Leu Gln Ser Leu
145                 150                 155                 160

Phe Gln Glu Val Gly Ile Lys Val Asp Gly Tyr Met Gly Ser Thr Ser
                165                 170                 175

Pro Ser Arg His Phe Ser Ser Leu Asp Ile Ala Val Cys Thr Ile Glu
            180                 185                 190

Arg Ala Asn Gly Leu Ile Asn Arg Leu Ile Glu Glu Asn Lys Met Asp
            195                 200                 205

Leu Leu Gly Met Val Val Asp Glu Leu His Met Leu Gly Asp Ser
210                 215                 220

His Arg Gly Tyr Leu Leu Glu Leu Leu Leu Thr Lys Ile Cys Tyr Ile
225                 230                 235                 240

Thr Arg Lys Ser Ala Ser Cys Gln Ala Asp Leu Ala Ser Ser Leu Ser
            245                 250                 255

Asn Ala Val Gln Ile Val Gly Met Ser Ala Thr Leu Pro Asn Leu Glu
            260                 265                 270

Leu Val Ala Ser Trp Leu Asn Ala Glu Leu Tyr His Thr Asp Phe Arg
            275                 280                 285

Pro Val Pro Leu Leu Glu Ser Val Lys Val Gly Asn Ser Ile Tyr Asp
290                 295                 300

Ser Ser Met Lys Leu Val Arg Glu Phe Glu Pro Met Leu Gln Val Lys
305                 310                 315                 320

Gly Asp Glu Asp His Val Ser Leu Cys Tyr Glu Thr Ile Cys Asp
            325                 330                 335

Asn His Ser Val Leu Leu Phe Cys Pro Ser Lys Lys Trp Cys Glu Lys
            340                 345                 350

Leu Ala Asp Ile Ile Ala Arg Glu Phe Tyr Asn Leu His His Gln Ala
            355                 360                 365

Glu Gly Leu Val Lys Pro Ser Glu Cys Pro Val Ile Leu Glu Gln
370                 375                 380

Lys Glu Leu Leu Glu Val Met Asp Gln Leu Arg Arg Leu Pro Ser Gly
385                 390                 395                 400

Leu Asp Ser Val Leu Gln Lys Thr Val Pro Trp Gly Val Ala Phe His
            405                 410                 415
```

```
His Ala Gly Leu Thr Phe Glu Arg Asp Ile Ile Glu Gly Ala Phe
            420                 425                 430
Arg Gln Gly Leu Ile Arg Val Leu Ala Ala Thr Ser Thr Leu Ser Ser
        435                 440                 445
Gly Val Asn Leu Pro Ala Arg Arg Val Ile Ile Arg Thr Pro Ile Phe
    450                 455                 460
Gly Gly Arg Pro Leu Asp Ile Leu Thr Tyr Lys Gln Met Val Gly Arg
465                 470                 475                 480
Ala Gly Arg Lys Gly Val Asp Thr Val Gly Glu Ser Ile Leu Ile Cys
                485                 490                 495
Lys Asn Ser Glu Lys Ser Lys Gly Ile Ala Leu Leu Gln Gly Ser Leu
            500                 505                 510
Lys Pro Val Arg Ser Cys Leu Gln Arg Arg Glu Gly Glu Val Thr
        515                 520                 525
Gly Ser Met Ile Arg Ala Ile Leu Glu Ile Ile Val Gly Gly Val Ala
    530                 535                 540
Ser Thr Ser Gln Asp Met His Thr Tyr Ala Ala Cys Thr Phe Leu Ala
545                 550                 555                 560
Ala Ser Met Lys Glu Gly Lys Gln Gly Ile Gln Arg Asn Gln Glu Ser
                565                 570                 575
Val Gln Leu Gly Ala Ile Glu Ala Cys Val Met Trp Leu Leu Glu Asn
            580                 585                 590
Glu Phe Ile Gln Ser Thr Glu Ala Ser Asp Gly Thr Glu Gly Lys Val
        595                 600                 605
Tyr His Pro Thr His Leu Gly Ser Ala Thr Leu Ser Ser Ser Leu Ser
    610                 615                 620
Pro Ala Asp Thr Leu Asp Ile Phe Ala Asp Leu Gln Arg Ala Met Lys
625                 630                 635                 640
Gly Phe Val Leu Glu Asn Asp Leu His Ile Leu Tyr Leu Val Thr Pro
                645                 650                 655
Met Phe Glu Asp Trp Thr Thr Ile Asp Trp Tyr Arg Phe Phe Cys Leu
            660                 665                 670
Trp Glu Lys Leu Pro Thr Ser Met Lys Arg Val Ala Glu Leu Val Gly
        675                 680                 685
Val Glu Glu Gly Phe Leu Ala Arg Cys Val Lys Gly Lys Val Val Ala
    690                 695                 700
Arg Thr Glu Arg Gln His Arg Gln Met Ala Ile His Lys Arg Phe Phe
705                 710                 715                 720
Thr Ser Leu Val Leu Leu Asp Leu Ile Ser Glu Val Pro Leu Arg Glu
                725                 730                 735
Ile Asn Gln Lys Tyr Gly Cys Asn Arg Gly Gln Ile Gln Ser Leu Gln
            740                 745                 750
Gln Ser Ala Ala Val Tyr Ala Gly Met Ile Thr Val Phe Ser Asn Arg
        755                 760                 765
Leu Gly Trp His Asn Met Glu Leu Leu Leu Ser Gln Phe Gln Lys Arg
    770                 775                 780
Leu Thr Phe Gly Ile Gln Arg Glu Leu Cys Asp Leu Val Arg Val Ser
785                 790                 795                 800
Leu Leu Asn Ala Gln Arg Ala Arg Val Leu Tyr Ala Ser Gly Phe His
                805                 810                 815
Thr Val Ala Asp Leu Ala Arg Ala Asn Ile Val Glu Val Glu Val Ile
            820                 825                 830
```

Leu Lys Asn Ala Val Pro Phe Lys Ser Ala Arg Lys Ala Val Asp Glu
        835                 840                 845

Glu Glu Glu Ala Val Glu Arg Arg Asn Met Arg Thr Ile Trp Val
850                 855                 860

Thr Gly Arg Lys Gly Leu Thr Glu Arg Glu Ala Ala Ala Leu Ile Val
865                 870                 875                 880

Glu Glu Ala Arg Met Ile Leu Gln Gln Asp Leu Val Glu Met Gly Val
                885                 890                 895

Gln Trp Asn Pro Cys Ala Leu Leu His Ser Ser Thr Cys Ser Leu Thr
                900                 905                 910

His Ser Glu Ser Glu Val Lys Glu His Thr Phe Ile Ser Gln Thr Lys
            915                 920                 925

Ser Ser Tyr Lys Lys Leu Thr Ser Lys Asn Lys Ser Asn Thr Ile Phe
    930                 935                 940

Ser Asp Ser Tyr Ile Lys His Ser Pro Asn Ile Val Gln Asp Leu Asn
945                 950                 955                 960

Lys Ser Arg Glu His Thr Ser Ser Phe Asn Cys Asn Phe Gln Asn Gly
                965                 970                 975

Asn Gln Glu His Gln Thr Cys Ser Ile Phe Arg Ala Arg Lys Arg Ala
                980                 985                 990

Ser Leu Asp Ile Asn Lys Glu Lys Pro Gly Ala Ser Gln Asn Glu Gly
            995                 1000                1005

Lys Thr Ser Asp Lys Lys Val Val Gln Thr Phe Ser Gln Lys Thr
    1010                1015                1020

Lys Lys Ala Pro Leu Asn Phe Asn Ser Glu Lys Met Ser Arg Ser
    1025                1030                1035

Phe Arg Ser Trp Lys Arg Arg Lys His Leu Lys Arg Ser Arg Asp
    1040                1045                1050

Ser Ser Pro Leu Lys Asp Ser Gly Ala Cys Arg Ile His Leu Gln
    1055                1060                1065

Gly Gln Thr Leu Ser Asn Pro Ser Leu Cys Glu Asp Pro Phe Thr
    1070                1075                1080

Leu Asp Glu Lys Lys Thr Glu Phe Arg Asn Ser Gly Pro Phe Ala
    1085                1090                1095

Lys Asn Val Ser Leu Ser Gly Lys Glu Lys Asp Asn Lys Thr Ser
    1100                1105                1110

Phe Pro Leu Gln Ile Lys Gln Asn Cys Ser Trp Asn Ile Thr Leu
    1115                1120                1125

Thr Asn Asp Asn Phe Val Glu His Ile Val Thr Gly Ser Gln Ser
    1130                1135                1140

Lys Asn Val Thr Cys Gln Ala Thr Ser Val Val Ser Glu Lys Gly
    1145                1150                1155

Arg Gly Val Ala Val Glu Ala Glu Lys Ile Asn Glu Val Leu Ile
    1160                1165                1170

Gln Asn Gly Ser Lys Asn Gln Asn Val Tyr Met Lys His His Asp
    1175                1180                1185

Ile His Pro Ile Asn Gln Tyr Leu Arg Lys Gln Ser His Glu Gln
    1190                1195                1200

Thr Ser Thr Ile Thr Lys Gln Lys Asn Ile Ile Glu Arg Gln Met
    1205                1210                1215

Pro Cys Glu Ala Val Ser Ser Tyr Ile Asn Arg Asp Ser Asn Val
    1220                1225                1230

Thr Ile Asn Cys Glu Arg Ile Lys Leu Asn Thr Glu Glu Asn Lys

```
                    1235                1240                1245
Pro Ser His Phe Gln Ala Leu Gly Asp Asp Ile Ser Arg Thr Val
    1250                1255                1260

Ile Pro Ser Glu Val Leu Pro Ser Ala Gly Ala Phe Ser Lys Ser
    1265                1270                1275

Glu Gly Gln His Glu Asn Phe Leu Asn Ile Ser Arg Leu Gln Glu
    1280                1285                1290

Lys Thr Gly Thr Tyr Thr Thr Asn Lys Thr Lys Asn Asn His Val
    1295                1300                1305

Ser Asp Leu Gly Leu Val Leu Cys Asp Phe Glu Asp Ser Phe Tyr
    1310                1315                1320

Leu Asp Thr Gln Ser Glu Lys Ile Ile Gln Gln Met Ala Thr Glu
    1325                1330                1335

Asn Ala Lys Leu Gly Ala Lys Asp Thr Asn Leu Ala Ala Gly Ile
    1340                1345                1350

Met Gln Lys Ser Leu Val Gln Gln Asn Ser Met Asn Ser Phe Gln
    1355                1360                1365

Lys Glu Cys His Ile Pro Phe Pro Ala Glu Gln His Pro Leu Gly
    1370                1375                1380

Ala Thr Lys Ile Asp His Leu Asp Leu Lys Thr Val Gly Thr Met
    1385                1390                1395

Lys Gln Ser Ser Asp Ser His Gly Val Asp Ile Leu Thr Pro Glu
    1400                1405                1410

Ser Pro Ile Phe His Ser Pro Ile Leu Leu Glu Glu Asn Gly Leu
    1415                1420                1425

Phe Leu Lys Lys Asn Glu Val Ser Val Thr Asp Ser Gln Leu Asn
    1430                1435                1440

Ser Phe Leu Gln Gly Tyr Gln Thr Gln Glu Thr Val Lys Pro Val
    1445                1450                1455

Ile Leu Leu Ile Pro Gln Lys Arg Thr Pro Thr Gly Val Glu Gly
    1460                1465                1470

Glu Cys Leu Pro Val Pro Glu Thr Ser Leu Asn Met Ser Asp Ser
    1475                1480                1485

Leu Leu Phe Asp Ser Phe Ser Asp Asp Tyr Leu Val Lys Glu Gln
    1490                1495                1500

Leu Pro Asp Met Gln Met Lys Glu Pro Leu Pro Ser Glu Val Thr
    1505                1510                1515

Ser Asn His Phe Ser Asp Ser Leu Cys Leu Gln Glu Asp Leu Ile
    1520                1525                1530

Lys Lys Ser Asn Val Asn Glu Asn Gln Asp Thr His Gln Gln Leu
    1535                1540                1545

Thr Cys Ser Asn Asp Glu Ser Ile Ile Phe Ser Glu Met Asp Ser
    1550                1555                1560

Val Gln Met Val Glu Ala Leu Asp Asn Val Asp Ile Phe Pro Val
    1565                1570                1575

Gln Glu Lys Asn His Thr Val Val Ser Pro Arg Ala Leu Glu Leu
    1580                1585                1590

Ser Asp Pro Val Leu Asp Glu His His Gln Gly Asp Gln Asp Gly
    1595                1600                1605

Gly Asp Gln Asp Glu Arg Ala Glu Lys Ser Lys Leu Thr Gly Thr
    1610                1615                1620

Arg Gln Asn His Ser Phe Ile Trp Ser Gly Ala Ser Phe Asp Leu
    1625                1630                1635
```

```
Ser Pro Gly Leu Gln Arg Ile Leu Asp Lys Val Ser Ser Pro Leu
    1640                1645                1650

Glu Asn Glu Lys Leu Lys Ser Met Thr Ile Asn Phe Ser Ser Leu
    1655                1660                1665

Asn Arg Lys Asn Thr Glu Leu Asn Glu Glu Gln Glu Val Ile Ser
    1670                1675                1680

Asn Leu Glu Thr Lys Gln Val Gln Gly Ile Ser Phe Ser Ser Asn
    1685                1690                1695

Asn Glu Val Lys Ser Lys Ile Glu Met Leu Glu Asn Asn Ala Asn
    1700                1705                1710

His Asp Glu Thr Ser Ser Leu Leu Pro Arg Lys Glu Ser Asn Ile
    1715                1720                1725

Val Asp Asp Asn Gly Leu Ile Pro Pro Thr Pro Ile Pro Thr Ser
    1730                1735                1740

Ala Ser Lys Leu Thr Phe Pro Gly Ile Leu Glu Thr Pro Val Asn
    1745                1750                1755

Pro Trp Lys Thr Asn Asn Val Leu Gln Pro Gly Glu Ser Tyr Leu
    1760                1765                1770

Phe Gly Ser Pro Ser Asp Ile Lys Asn His Asp Leu Ser Pro Gly
    1775                1780                1785

Ser Arg Asn Gly Phe Lys Asp Asn Ser Pro Ile Ser Asp Thr Ser
    1790                1795                1800

Phe Ser Leu Gln Leu Ser Gln Asp Gly Leu Gln Leu Thr Pro Ala
    1805                1810                1815

Ser Ser Ser Ser Glu Ser Leu Ser Ile Ile Asp Val Ala Ser Asp
    1820                1825                1830

Gln Asn Leu Phe Gln Thr Phe Ile Lys Glu Trp Arg Cys Lys Lys
    1835                1840                1845

Arg Phe Ser Ile Ser Leu Ala Cys Glu Lys Ile Arg Ser Leu Thr
    1850                1855                1860

Ser Ser Lys Thr Ala Thr Ile Gly Ser Arg Phe Lys Gln Ala Ser
    1865                1870                1875

Ser Pro Gln Glu Ile Pro Ile Arg Asp Asp Gly Phe Pro Ile Lys
    1880                1885                1890

Gly Cys Asp Asp Thr Leu Val Val Gly Leu Ala Val Cys Trp Gly
    1895                1900                1905

Gly Arg Asp Ala Tyr Tyr Phe Ser Leu Gln Lys Glu Gln Lys His
    1910                1915                1920

Ser Glu Ile Ser Ala Ser Leu Val Pro Pro Ser Leu Asp Pro Ser
    1925                1930                1935

Leu Thr Leu Lys Asp Arg Met Trp Tyr Leu Gln Ser Cys Leu Arg
    1940                1945                1950

Lys Glu Ser Asp Lys Glu Cys Ser Val Val Ile Tyr Asp Phe Ile
    1955                1960                1965

Gln Ser Tyr Lys Ile Leu Leu Ser Cys Gly Ile Ser Leu Glu
    1970                1975                1980

Gln Ser Tyr Glu Asp Pro Lys Val Ala Cys Trp Leu Leu Asp Pro
    1985                1990                1995

Asp Ser Gln Glu Pro Thr Leu His Ser Ile Val Thr Ser Phe Leu
    2000                2005                2010

Pro His Glu Leu Pro Leu Leu Glu Gly Met Glu Thr Ser Gln Gly
    2015                2020                2025
```

-continued

```
Ile Gln Ser Leu Gly Leu Asn Ala Gly Ser Glu His Ser Gly Arg
    2030                2035                2040

Tyr Arg Ala Ser Val Glu Ser Ile Leu Ile Phe Asn Ser Met Asn
    2045                2050                2055

Gln Leu Asn Ser Leu Leu Gln Lys Glu Asn Leu Gln Asp Val Phe
    2060                2065                2070

Arg Lys Val Glu Met Pro Ser Gln Tyr Cys Leu Ala Leu Leu Glu
    2075                2080                2085

Leu Asn Gly Ile Gly Phe Ser Thr Ala Glu Cys Glu Ser Gln Lys
    2090                2095                2100

His Ile Met Gln Ala Lys Leu Asp Ala Ile Glu Thr Gln Ala Tyr
    2105                2110                2115

Gln Leu Ala Gly His Ser Phe Ser Phe Thr Ser Ser Asp Asp Ile
    2120                2125                2130

Ala Glu Val Leu Phe Leu Glu Leu Lys Leu Pro Pro Asn Arg Glu
    2135                2140                2145

Met Lys Asn Gln Gly Ser Lys Lys Thr Leu Gly Ser Thr Arg Arg
    2150                2155                2160

Gly Ile Asp Asn Gly Arg Lys Leu Arg Leu Gly Arg Gln Phe Ser
    2165                2170                2175

Thr Ser Lys Asp Val Leu Asn Lys Leu Lys Ala Leu His Pro Leu
    2180                2185                2190

Pro Gly Leu Ile Leu Glu Trp Arg Arg Ile Thr Asn Ala Ile Thr
    2195                2200                2205

Lys Val Val Phe Pro Leu Gln Arg Glu Lys Cys Leu Asn Pro Phe
    2210                2215                2220

Leu Gly Met Glu Arg Ile Tyr Pro Val Ser Gln Ser His Thr Ala
    2225                2230                2235

Thr Gly Arg Ile Thr Phe Thr Glu Pro Asn Ile Gln Asn Val Pro
    2240                2245                2250

Arg Asp Phe Glu Ile Lys Met Pro Thr Leu Val Gly Glu Ser Pro
    2255                2260                2265

Pro Ser Gln Ala Val Gly Lys Gly Leu Leu Pro Met Gly Arg Gly
    2270                2275                2280

Lys Tyr Lys Lys Gly Phe Ser Val Asn Pro Arg Cys Gln Ala Gln
    2285                2290                2295

Met Glu Glu Arg Ala Ala Asp Arg Gly Met Pro Phe Ser Ile Ser
    2300                2305                2310

Met Arg His Ala Phe Val Pro Phe Pro Gly Gly Ser Ile Leu Ala
    2315                2320                2325

Ala Asp Tyr Ser Gln Leu Glu Leu Arg Ile Leu Ala His Leu Ser
    2330                2335                2340

His Asp Arg Arg Leu Ile Gln Val Leu Asn Thr Gly Ala Asp Val
    2345                2350                2355

Phe Arg Ser Ile Ala Ala Glu Trp Lys Met Ile Glu Pro Glu Ser
    2360                2365                2370

Val Gly Asp Asp Leu Arg Gln Gln Ala Lys Gln Ile Cys Tyr Gly
    2375                2380                2385

Ile Ile Tyr Gly Met Gly Ala Lys Ser Leu Gly Glu Gln Met Gly
    2390                2395                2400

Ile Lys Glu Asn Asp Ala Ala Cys Tyr Ile Asp Ser Phe Lys Ser
    2405                2410                2415

Arg Tyr Thr Gly Ile Asn Gln Phe Met Thr Glu Thr Val Lys Asn
```

-continued

```
            2420                2425                2430
Cys Lys Arg Asp Gly Phe Val Gln Thr Ile Leu Gly Arg Arg Arg
        2435                2440                2445

Tyr Leu Pro Gly Ile Lys Asp Asn Pro Tyr Arg Lys Ala His
    2450                2455                2460

Ala Glu Arg Gln Ala Ile Asn Thr Ile Val Gln Gly Ser Ala Ala
2465                2470                2475

Asp Ile Val Lys Ile Ala Thr Val Asn Ile Gln Lys Gln Leu Glu
    2480                2485                2490

Thr Phe His Ser Thr Phe Lys Ser His Gly His Arg Glu Gly Met
    2495                2500                2505

Leu Gln Ser Asp Gln Thr Gly Leu Ser Arg Lys Arg Lys Leu Gln
    2510                2515                2520

Gly Met Phe Cys Pro Ile Arg Gly Gly Phe Phe Ile Leu Gln Leu
    2525                2530                2535

His Asp Glu Leu Leu Tyr Glu Val Ala Glu Asp Val Val Gln
    2540                2545                2550

Val Ala Gln Ile Val Lys Asn Glu Met Glu Ser Ala Val Lys Leu
2555                2560                2565

Ser Val Lys Leu Lys Val Lys Val Ile Gly Ala Ser Trp Gly
    2570                2575                2580

Glu Leu Lys Asp Phe Asp Val
    2585                2590

<210> SEQ ID NO 11
<211> LENGTH: 2536
<212> TYPE: PRT
<213> ORGANISM: Tupaia chinensis

<400> SEQUENCE: 11

Met Asn Leu Leu Arg Arg Ser Gly Lys Arg Arg Thr Asp Ser Gly
1               5                   10                  15

Ser Asp Ser Phe Ser Gly Ser Gly Gly Asp Ser Cys Ala Ser Thr Val
                20                  25                  30

Leu Leu Ser Lys Gln Leu Gly Cys Gly Gln Ile Pro Leu Pro Gly Glu
            35                  40                  45

Gly Arg Ala Pro Thr Arg Val Gln Tyr Ser Leu Gln Ile Leu Asn Pro
        50                  55                  60

Gly Glu Cys Lys Gln Thr Asp Pro Asp Pro Ile Asp Lys Leu Leu
65                  70                  75                  80

Leu Ala Asn Trp Gly Leu Pro Lys Ala Val Leu Glu Lys Tyr His Ser
                85                  90                  95

Phe Gly Val Lys Lys Met Phe Glu Trp Gln Ala Glu Cys Leu Leu Leu
            100                 105                 110

Gly Gln Val Leu Glu Gly Lys Asn Leu Val Tyr Ser Ala Pro Thr Ser
        115                 120                 125

Ala Gly Lys Thr Leu Val Ala Glu Leu Leu Ile Leu Lys Arg Val Leu
    130                 135                 140

Glu Met Arg Lys Lys Ala Leu Phe Ile Leu Pro Phe Val Ser Val Ala
145                 150                 155                 160

Lys Glu Lys Lys Tyr Tyr Leu Gln Ser Leu Phe Gln Glu Val Gly Ile
                165                 170                 175

Lys Val Asp Gly Tyr Val Gly Ser Thr Ser Pro Thr Gly His Phe Ser
            180                 185                 190
```

```
Ser Leu Asp Ile Ala Val Cys Thr Ile Glu Arg Ala Asn Gly Leu Ile
            195                 200                 205

Asn Arg Leu Ile Glu Glu Asn Lys Met Asp Leu Leu Gly Met Val Val
    210                 215                 220

Val Asp Glu Leu His Met Leu Gly Asp Ser His Arg Gly Tyr Leu Leu
225                 230                 235                 240

Glu Leu Leu Leu Thr Lys Ile Cys Tyr Ile Thr Gln Lys Ser Ala Ser
                245                 250                 255

Cys Gln Ala Asp Leu Val Ser Pro Leu Phe Asn Gly Val Gln Ile Val
            260                 265                 270

Gly Met Ser Ala Thr Leu Pro Asn Leu Asp Leu Ile Ala Ser Trp Leu
        275                 280                 285

Asn Ala Glu Leu Tyr His Thr Asp Phe Arg Pro Val Pro Leu Leu Glu
    290                 295                 300

Thr Val Lys Ile Gly Asn Ser Ile Tyr Asp Ser Ser Met Lys Leu Val
305                 310                 315                 320

Arg Glu Phe Gln Pro Met Leu Gln Val Lys Gly Asp Glu Asp His Ile
                325                 330                 335

Val Ser Leu Cys Tyr Glu Thr Ile Cys Asp Asn His Ser Val Leu Leu
            340                 345                 350

Phe Cys Pro Ser Lys Lys Trp Cys Glu Lys Leu Ala Asp Thr Ile Ala
        355                 360                 365

Arg Glu Phe Tyr Asn Leu His His Gln Ala Glu Gly Leu Val Lys Pro
    370                 375                 380

Pro Glu Phe Pro Pro Val Thr Leu Glu Pro Lys Gly Leu Gln Glu Val
385                 390                 395                 400

Met Asp Gln Leu Lys His Leu Pro Ser Gly Leu Asp Ser Val Leu Gln
                405                 410                 415

Lys Thr Val Pro Trp Gly Val Ala Phe His His Ala Gly Leu Thr Phe
            420                 425                 430

Glu Glu Arg Asp Ile Ile Glu Gly Ala Phe Arg Gln Gly Leu Ile Arg
        435                 440                 445

Val Leu Ala Ala Thr Ser Thr Leu Ser Ser Gly Val Asn Leu Pro Ala
    450                 455                 460

Arg Arg Val Ile Ile Arg Thr Pro Ile Phe Ser Gly Arg Pro Leu Asp
465                 470                 475                 480

Val Leu Thr Tyr Lys Gln Met Val Gly Arg Ala Gly Arg Lys Gly Val
                485                 490                 495

Asp Thr Val Gly Glu Ser Ile Leu Val Cys Lys Ile Ser Glu Lys Ser
            500                 505                 510

Lys Gly Thr Ala Leu Leu Gln Gly Ser Leu Lys Pro Val Cys Ser Cys
        515                 520                 525

Leu Arg Arg His Glu Gly Glu Val Thr Ala Cys Met Ile Arg Ala
    530                 535                 540

Ile Leu Glu Ile Ile Val Gly Gly Val Ala Ser Thr Pro Gln Asp Met
545                 550                 555                 560

Gln Asn Tyr Ala Ser Cys Thr Phe Leu Ala Ala Ser Met Lys Glu Gly
                565                 570                 575

Gln Gln Glu Ile Glu Arg Asn Gln Asn Ser Val Gln Leu Gly Ala Ile
            580                 585                 590

Glu Ala Cys Val Met Trp Leu Leu Glu Asn Glu Phe Ile Gln Val Ala
        595                 600                 605

Glu Val Gly Asp Gly Thr Glu Gly Lys Val Tyr His Pro Thr His Leu
```

```
                    610             615             620
Gly Ser Ala Thr Leu Ser Ser Leu Ser Pro Thr Asp Thr Leu Asp
625             630             635             640

Ile Phe Ala Asp Leu Gln Arg Ala Met Lys Gly Phe Val Leu Glu Asn
                645             650             655

Asp Leu His Ile Val Tyr Leu Ile Thr Pro Met Phe Glu Asp Trp Thr
                660             665             670

Thr Ile Asp Trp Tyr Arg Phe Phe Cys Leu Trp Glu Lys Leu Pro Ile
        675             680             685

Ser Met Lys Arg Val Ala Glu Leu Val Gly Val Glu Glu Gly Phe Leu
690             695             700

Ala Arg Cys Val Lys Gly Lys Val Val Ala Arg Thr Glu Arg Gln His
705             710             715             720

Arg Gln Met Ala Ile His Lys Arg Phe Phe Thr Ser Leu Val Leu Leu
                725             730             735

Asp Leu Ile Ser Glu Val Pro Leu Lys Glu Ile Asn Gln Lys Tyr Gly
                740             745             750

Cys Asn Arg Gly Gln Ile Gln Ser Leu Gln Gln Ser Ala Ala Val Tyr
        755             760             765

Ala Gly Met Ile Thr Val Phe Ser Asn Arg Leu Gly Trp His Asn Met
770             775             780

Glu Leu Leu Leu Ser Gln Phe Gln Lys Arg Leu Thr Phe Gly Ile Gln
785             790             795             800

Arg Glu Leu Cys Asp Leu Val Arg Val Ser Leu Leu Asn Ala Gln Arg
                805             810             815

Ala Arg Ala Leu Tyr Ala Ser Gly Phe Leu Thr Val Ala Asp Leu Ala
        820             825             830

Arg Ala Asn Ile Ala Asp Val Glu Met Val Leu Lys Asn Ala Val Pro
        835             840             845

Phe Lys Ser Ala Arg Lys Ala Val Asp Glu Glu Asp Ala Ala Glu
        850             855             860

Glu Arg Arg Asn Met Gln Thr Ile Trp Val Thr Gly Arg Lys Gly Leu
865             870             875             880

Thr Glu Arg Glu Ala Ala Leu Ile Val Glu Glu Ala Lys Met Ile
                885             890             895

Leu Gln Glu Asp Leu Val Glu Met Gly Val Gln Trp Asn Pro His Ser
                900             905             910

Pro Leu Asn Ser Ser Lys Leu Ser Leu Thr Ser Ser Asp Ser Glu Val
        915             920             925

Lys Glu Leu Ile Phe Ile Pro Gln Thr Gln Ser Ser Cys Lys Arg Leu
930             935             940

Ile Ser Lys Asn Lys Ser Asn Ser Ile Phe Ser Asp Ser Tyr Val Lys
945             950             955             960

Arg Ser Leu Asn Thr Val Gln Asp Leu Asp Lys Ser Arg Glu Arg His
                965             970             975

Thr Ser Pro Ile Tyr Lys Phe Gln Asp Lys Asn Gln Glu Tyr Gln Arg
        980             985             990

His Ser Ile Ser Lys Arg Ala Cys Leu Asp Ile Ser Lys Glu Lys Pro
        995             1000            1005

Gly Thr Ser Leu Asn Glu Gly Arg Lys Ser Thr Gln Lys Ala Val
        1010            1015            1020

Gln Thr Phe Ser Phe Glu Lys Thr Lys Ile Ala Ser Asn Phe Ser
        1025            1030            1035
```

-continued

```
Ser Asp Lys Met Ser Thr Ser Phe Arg Ser Trp Lys His Arg Lys
1040                1045                1050

His Leu Lys Gln Ser Arg Ser Ser Ser Val Lys Asp Ser Ser
    1055                1060                1065

Ile Ser Arg Thr Asp Leu Gln Arg Trp Arg Lys Ser Ser Pro Ile
1070                1075                1080

Leu Cys Glu Asp Pro Ser Ala Leu Gly Glu Arg Asn Val Glu Phe
    1085                1090                1095

Arg Ser Pro Gly Pro Phe Ala Lys Asn Val Ser Phe Cys Val Glu
1100                1105                1110

Arg Lys Tyr Asp Gln Thr Glu Gln Ser Cys Thr Arg Ser Gly Ala
    1115                1120                1125

Ile Ser Asn Asp Ile Phe Val Glu His Phe Asp Thr Gly Ser Gln
1130                1135                1140

Ser Lys Thr Met Ala Cys Gln Thr Phe Gly Val Val Ser Glu Asn
    1145                1150                1155

Gly Arg Gly Leu Ala Ile Val Glu Thr Glu Lys Ile Asn Lys Val
1160                1165                1170

Leu Ile Gln Asn Asp Ser Lys Asn Gln Asn Val Asn Leu Lys Tyr
    1175                1180                1185

Cys Val Thr His Pro Val Asn Gln Asp Leu Gly Lys Gln Cys Asp
1190                1195                1200

Gln Gln Thr Asp Thr Cys Thr Lys Gln Lys Glu Ile Thr Glu Arg
    1205                1210                1215

Gln Met Pro Phe Glu Ala Val Ser Ser Asn Thr Asn Gly Asp Ser
1220                1225                1230

Asp Val Thr Ser Val Lys Cys Lys Ser Val Lys Phe Asn Ser Glu
    1235                1240                1245

Glu Asn Lys Pro Ser His Phe Gln Ala Phe Gly Asn Asn Ile Ser
1250                1255                1260

Arg Thr Gln Ile Pro Ser Glu Ile Gln Val Leu Thr Gly Thr Phe
    1265                1270                1275

Arg Glu Ser Gly Gly Gln His Asp Ser Phe Gln Asn Thr Ser Lys
1280                1285                1290

Ile Gln Glu Lys Ala Cys Ala Tyr Leu Thr Asn Lys Thr Glu Asn
    1295                1300                1305

Asn Asn Val Ser Asp Leu Gly Leu Val Leu Cys Asp Phe Glu Asp
1310                1315                1320

Ser Phe Tyr Leu Asp Thr Gln Ser Glu Lys Ile Ile Gln Glu Ile
    1325                1330                1335

Ala Thr Glu Asn Ala Lys Gln Ala Ala Glu Asp Pro Asn Leu Ala
1340                1345                1350

Ala Glu Lys Met Gln Thr Asn Val Gln Lys Gln Asn Leu Ile Ser
    1355                1360                1365

Ser Phe Gln Asn Ala Leu Cys Val Thr Leu Pro Gly Glu Gln His
1370                1375                1380

Ser Pro Gly Val Thr Asn Thr Glu Pro Leu Asp His Lys Thr Gly
    1385                1390                1395

Asp Thr Arg His Lys Pro Ser Thr Asp Ser Cys Arg Val Asp Ile
1400                1405                1410

Leu Thr Arg Glu Asn Ser Val Phe His Ser Pro Ile Leu Leu Glu
    1415                1420                1425
```

-continued

Glu Asn Ser Pro Cys Phe Lys Gly Asn Glu Leu Ser Val Thr Asp
1430                1435                1440

Ser Gln Leu Asn Asn Phe Leu Gln Gly Tyr Gln Thr Gln Glu Thr
1445                1450                1455

Val Lys Pro Gly Ile Pro Val Val Pro Gln Lys Glu Thr Pro Thr
1460                1465                1470

Ala Met Glu Gly Glu Cys Leu Pro Val Pro Glu Thr Ser Leu Asn
1475                1480                1485

Met Ser Asp Ser Leu Leu Phe Asp Ser Phe Asn Glu Asp Tyr Leu
1490                1495                1500

Val Lys Glu Gln Pro Ala Lys Val Gln Ala Lys Glu Thr Phe Leu
1505                1510                1515

Thr Thr Glu Ile Thr Ser Asp His Phe Ser Asp Ser Leu Asn Ile
1520                1525                1530

Arg Glu Gly Pro Ala Lys Thr Ser Asp Ile Asn Gly Asn Gln Asp
1535                1540                1545

Ile His Gln Gln Leu Thr Cys Phe Asn Asp Glu Ser Leu Met Phe
1550                1555                1560

Ser Glu Met Asp Ser Ala Gln Val Val Glu Val Leu Asp Lys Leu
1565                1570                1575

Asp Ile Phe Pro Ile Gln Glu Lys His Asn Thr Ala Val Ser Leu
1580                1585                1590

Ser Thr Leu Lys Leu Ser Asp Pro Val Ile Val Asn Asn His
1595                1600                1605

Arg Gln Gly Glu Val Ile Gly Gly Glu Gln Asp Glu Lys Ala Gln
1610                1615                1620

Gln Ser Lys Ile Thr Glu Thr Gly Gln Asn Asn Ser Phe Met Trp
1625                1630                1635

Ser Gly Ala Ser Phe Asp Leu Ser Pro Gly Leu Gln Arg Ile Leu
1640                1645                1650

Asp Lys Val Ser Ser Pro Leu Glu Asn Glu Met Leu Lys Ser Met
1655                1660                1665

Pro Ile Asn Leu Ser Ser Leu Lys Gly Lys Asn Arg Glu Leu Asn
1670                1675                1680

Glu Lys Gln Glu Val Ile Ser Asn Leu Asp Thr Ser Gln Met Gln
1685                1690                1695

Arg Ile Ser Cys Phe His Thr Asn Glu Val Lys Asn Asn Ile Ala
1700                1705                1710

Pro Glu Asn Ser Val Asn His Gly Ala His Leu Ser Pro Leu Ser
1715                1720                1725

Phe Lys Glu Ser Cys Ile Val Asp Asp Asn Gly Leu Ile Pro Pro
1730                1735                1740

Thr Pro Val Pro Ala Ser Ala Ser Lys Phe Ser Phe Pro Gly Ile
1745                1750                1755

Leu Gly Thr Ser Ala Val Leu Gln Asn Thr Gly Ser Val Leu Gln
1760                1765                1770

Ser Gly Gly Ser Tyr Leu Phe Gly Ser Pro Ser Asp Thr Lys Asn
1775                1780                1785

His Glu Leu Ser Pro Asp Ser Arg Asn Gly Phe Lys Asp Glu Ser
1790                1795                1800

Pro Arg Lys Glu Lys Ser Phe Ser Leu Gln Phe Ser Gln Asp Gly
1805                1810                1815

Leu Gln Leu Thr Pro Ala Ser Ser Asn Ser Gln Ser Leu Ala Ile

-continued

```
                   1820                1825               1830
Ile Asp Val Ala Ser Asn Gln Thr Leu Phe Gln Thr Phe Ile Lys
                   1835                1840               1845
Glu Trp Gln Cys Lys Lys Arg Phe Ser Ile Ser Leu Ala Cys Glu
                   1850                1855               1860
Lys Ile Gly Ser Ser Ala Ser Ser Lys Thr Ala Thr Ile Gly Gly
                   1865                1870               1875
Arg Phe Lys Gln Gly Ser Ser Gln Glu Thr Pro Ile Arg Asp
                   1880                1885               1890
Gly Gly Phe Pro Val Lys Gly His Glu Asp Ile Leu Val Val Gly
                   1895                1900               1905
Leu Ala Val Cys Trp Gly Gly Arg Asp Ala Tyr Tyr Phe Ser Leu
                   1910                1915               1920
Gln Gln Glu Gln Lys His Ser Glu Ile Ser Ala Ser Leu Asn Pro
                   1925                1930               1935
Pro Pro Leu Asp Pro Gly Leu Thr Val Lys Asp Arg Leu Trp His
                   1940                1945               1950
Leu Gln Ser Cys Leu Gln Lys Lys Ser Gly Lys Glu Cys Ser Val
                   1955                1960               1965
Ile Ile Tyr Asp Phe Ile Gln Ser Tyr Lys Ile Leu Leu Leu Ser
                   1970                1975               1980
Cys Gly Ile Ser Leu Glu Gln Asp Phe Glu Asp Pro Lys Val Ala
                   1985                1990               1995
Cys Trp Leu Leu Asp Pro Asp Ser Lys Glu Pro Thr Leu His Ser
                   2000                2005               2010
Ile Val Thr Ser Phe Leu Pro His Glu Leu Pro Leu Leu Glu Gly
                   2015                2020               2025
Met Glu Thr Gly Glu Gly Ile Gln Ser Leu Gly Leu Asn Val Asn
                   2030                2035               2040
Thr Glu His Ser Gly Arg Tyr Arg Ala Ser Val Glu Ser Val Leu
                   2045                2050               2055
Ile Phe Ser Cys Met Thr Gln Leu Asn Ser Leu Leu Gln Lys Glu
                   2060                2065               2070
Asn Leu Gln Asp Val Phe Cys Lys Val Glu Met Pro Ser Gln Tyr
                   2075                2080               2085
Cys Leu Ala Leu Leu Glu Leu Asn Gly Ile Gly Phe Ser Thr Ala
                   2090                2095               2100
Glu Cys Glu Ser Gln Lys Gln Ile Met Gln Ala Lys Leu Asp Ala
                   2105                2110               2115
Ile Glu Thr Glu Ala Tyr Gln Leu Ala Gly His Ser Phe Ser Phe
                   2120                2125               2130
Thr Ser Ser Asp Asp Ile Ala Glu Val Leu Phe Leu Glu Leu Lys
                   2135                2140               2145
Leu Pro Pro Asn Gly Glu Met Lys Asn Gln Gly Ile Lys Lys Thr
                   2150                2155               2160
Leu Gly Ser Thr Arg Arg Gly Ile Asp Ser Gly Arg Lys Leu Arg
                   2165                2170               2175
Leu Gly Arg Gln Phe Ser Thr Arg Arg Ile Thr Phe Thr Glu Pro
                   2180                2185               2190
Asn Ile Gln Asn Val Pro Arg Asp Phe Glu Ile Lys Met Pro Thr
                   2195                2200               2205
Leu Val Glu Glu Ser Pro Pro Ser Gln Ala Leu Gly Lys Gly Leu
                   2210                2215               2220
```

```
Leu Pro Met Gly Arg Gly Lys Ile Lys Gly Arg Arg Leu Asn
        2225                2230                2235

Pro Glu His Gln Ala His Leu Glu Arg Ala Ser Asp Lys Gly
    2240                2245                2250

Met Pro Phe Ser Val Ser Met Arg His Ala Phe Val Pro Phe Pro
    2255                2260                2265

Gly Gly Leu Ile Leu Ala Ala Asp Tyr Ser Gln Leu Glu Leu Arg
    2270                2275                2280

Ile Leu Ala His Leu Ser His Asp His Arg Leu Ile Gln Val Leu
    2285                2290                2295

Asn Thr Gly Ala Asp Val Phe Arg Ser Ile Ala Ala Glu Trp Lys
    2300                2305                2310

Met Ile Glu Pro Glu Thr Val Gly Asn Glu Leu Arg Gln Gln Ala
    2315                2320                2325

Lys Gln Ile Cys Tyr Gly Ile Ile Tyr Gly Met Gly Ala Lys Ser
    2330                2335                2340

Leu Gly Glu Gln Met Gly Ile Lys Glu Asn Asp Ala Ala Cys Tyr
    2345                2350                2355

Ile Asp Ser Phe Lys Ser Arg Tyr Thr Gly Ile Asn His Phe Met
    2360                2365                2370

Arg Glu Thr Val Lys Asn Cys Lys Arg Asp Gly Phe Val Gln Thr
    2375                2380                2385

Ile Leu Gly Arg Arg Arg Tyr Leu Pro Gly Ile Lys Asp Asn Asn
    2390                2395                2400

Pro Tyr His Lys Ala His Ala Glu Arg Gln Ala Ile Asn Thr Thr
    2405                2410                2415

Val Gln Gly Ser Ala Ala Asp Ile Val Lys Val Ala Thr Val Asn
    2420                2425                2430

Ile Gln Lys Gln Leu Glu Thr Leu Arg Ser Thr Phe Lys Ser His
    2435                2440                2445

Gly His Arg Glu Ser Met Leu Arg Arg Asp Lys Thr Gly Leu Leu
    2450                2455                2460

Pro Lys Arg Lys Leu Gln Gly Met Phe Cys Pro Ile Arg Gly Gly
    2465                2470                2475

Phe Phe Ile Leu Gln Leu His Asp Glu Leu Leu Tyr Glu Val Ala
    2480                2485                2490

Glu Glu Asp Ala Val Gln Val Ala Gln Ile Val Lys Asn Glu Met
    2495                2500                2505

Glu Asn Ala Ile Lys Leu Ser Val Lys Leu Lys Val Lys Val Lys
    2510                2515                2520

Ile Gly Ala Ser Trp Ala Glu Leu Arg Asp Phe Asp Val
    2525                2530                2535

<210> SEQ ID NO 12
<211> LENGTH: 2383
<212> TYPE: PRT
<213> ORGANISM: Cricetulus griseus

<400> SEQUENCE: 12

Met Arg Lys Lys Ala Leu Phe Ile Leu Pro Phe Val Ser Val Ala Lys
1               5                   10                  15

Glu Lys Lys Tyr Tyr Leu Gln Ser Leu Phe Gln Glu Val Gly Ile Lys
                20                  25                  30

Val Asp Gly Tyr Met Gly Ser Ser Ser Pro Thr Gly Arg Phe Ser Ser
```

```
            35                  40                  45
Leu Asp Ile Ala Val Cys Thr Ile Glu Arg Ala Asn Gly Leu Ile Asn
 50                  55                  60

Arg Leu Ile Glu Glu Asn Lys Met Asp Leu Leu Gly Met Val Val Val
 65                  70                  75                  80

Asp Glu Leu His Met Leu Gly Asp Ser His Arg Gly Tyr Leu Leu Glu
                 85                  90                  95

Leu Leu Leu Thr Lys Ile Cys Tyr Val Thr Arg Lys Ser Thr Leu Cys
                100                 105                 110

Gln Ala Asp Ser Ala Arg Ala Leu Cys Asn Ala Val Gln Ile Val Gly
            115                 120                 125

Met Ser Ala Thr Leu Pro Asn Leu Gln Leu Val Ala Ser Trp Leu Asp
        130                 135                 140

Ala Glu Leu Tyr His Thr Asp Phe Arg Pro Val Pro Leu Leu Glu Ser
145                 150                 155                 160

Ile Lys Ile Gly Asn Ser Ile Tyr Asp Ser Ser Met Lys Leu Val Arg
                165                 170                 175

Glu Leu Gln Pro Val Leu Gln Val Lys Gly Asp Glu Asp His Ile Val
            180                 185                 190

Ser Leu Cys Tyr Glu Thr Val Cys Asp Asn His Ser Val Leu Leu Phe
        195                 200                 205

Cys Pro Ser Lys Lys Trp Cys Glu Lys Val Ala Asp Ile Ile Ala Arg
210                 215                 220

Glu Phe Tyr Asn Leu His His Gln Pro Glu Arg Leu Val Lys Pro Ser
225                 230                 235                 240

Glu Phe Pro Pro Val Asn Leu Asp Gln Lys Ser Leu Leu Glu Val Met
                245                 250                 255

Asp Gln Leu Lys Arg Ser Pro Ser Gly Leu Asp Ser Val Leu Lys Asn
            260                 265                 270

Thr Val Pro Trp Gly Val Ala Phe His His Ala Gly Leu Thr Phe Glu
        275                 280                 285

Glu Arg Asp Ile Ile Glu Gly Ala Phe Arg Gln Gly Leu Ile Arg Val
290                 295                 300

Leu Ala Ala Thr Ser Thr Leu Ser Ser Gly Val Asn Leu Pro Ala Arg
305                 310                 315                 320

Arg Val Ile Ile Arg Thr Pro Val Phe Gly Gly Gln Thr Leu Asp Ile
                325                 330                 335

Leu Thr Tyr Lys Gln Met Val Gly Arg Ala Gly Arg Lys Gly Val Asp
            340                 345                 350

Thr Met Ala Ala Val Tyr Asp Asp Phe Gln Ile Ile Val Gly Gly Val
        355                 360                 365

Ala Ser Thr Ser Gln Asp Met Gln Thr Tyr Ala Ser Cys Thr Phe Leu
            370                 375                 380

Ala Ala Ala Val Lys Glu Gly Lys Gln Gly Ile Gln Arg Asn Gln Asp
385                 390                 395                 400

Asp Val His Phe Gly Ala Ile Asp Ala Cys Val Thr Trp Leu Leu Glu
                405                 410                 415

Asn Glu Phe Ile Gln Glu Ala Glu Pro Ser Asp Gly Ser Gly Gly Lys
            420                 425                 430

Val Tyr His Pro Thr His Leu Gly Ser Ala Thr Leu Ser Ser Ser Leu
        435                 440                 445

Ser Pro Thr Asp Thr Leu Asp Ile Phe Ala Asp Leu Gln Arg Ala Met
450                 455                 460
```

```
Lys Gly Phe Val Leu Glu Asn Asp Leu His Ile Val Tyr Leu Val Thr
465                 470                 475                 480

Pro Val Phe Glu Asp Trp Thr Gly Ile Asp Trp Tyr Arg Phe Phe Cys
                485                 490                 495

Leu Trp Glu Lys Leu Pro Thr Ser Met Lys Arg Val Ala Glu Leu Val
            500                 505                 510

Gly Val Glu Glu Gly Phe Leu Ala Arg Cys Val Lys Gly Lys Val Val
        515                 520                 525

Ala Arg Thr Asp Arg Gln His Arg Gln Met Ala Ile His Lys Arg Phe
530                 535                 540

Phe Thr Ser Leu Val Leu Leu Asp Leu Ile Ser Glu Ile Pro Leu Lys
545                 550                 555                 560

Glu Ile Asn Gln Lys Tyr Gly Cys Asn Arg Gly Gln Ile Gln Ser Leu
                565                 570                 575

Gln Gln Ser Ala Ala Val Tyr Ala Gly Met Ile Thr Val Phe Ser Asn
            580                 585                 590

Arg Leu Gly Trp His Asn Met Glu Leu Leu Ser Gln Phe Gln Lys
        595                 600                 605

Arg Leu Thr Phe Gly Ile Gln Arg Glu Leu Cys Asp Leu Ile Arg Val
610                 615                 620

Ser Leu Leu Asn Ala Gln Arg Ala Arg Phe Leu Tyr Ala Ser Gly Phe
625                 630                 635                 640

Leu Thr Val Ala Asp Leu Ala Arg Ala Asn Val Ala Glu Val Glu Val
                645                 650                 655

Val Leu Lys Asn Ala Val Pro Phe Lys Ser Thr Arg Lys Ala Val Asp
            660                 665                 670

Glu Glu Glu Glu Ala Ala Glu Glu Arg Arg Asn Met Gln Thr Ile Trp
        675                 680                 685

Val Ser Gly Arg Lys Gly Leu Ser Ala Arg Glu Ala Ala Thr Leu Ile
        690                 695                 700

Val Glu Glu Ala Lys Thr Ile Leu Gln Gln Asp Leu Leu Glu Met Gly
705                 710                 715                 720

Val Gln Trp Asp Pro Asn Ser Ser Leu Ser Ser Thr Ser Ser Leu
                725                 730                 735

Thr Ser Ser Glu Ser Glu Val Asn Glu Arg Thr Leu Gln Ser Gln Thr
            740                 745                 750

Lys Asn Ser His Lys Arg Leu Thr Ser Lys Asn Arg Asn Ser Met Arg
                755                 760                 765

Ala Ser Val Ser Asn Asp Lys Pro Ser Pro Asp Thr Ala Gln Gly Leu
            770                 775                 780

Gly Glu His Ser Glu His Thr Asp Ser Leu Cys Leu Leu Gln Gly Asn
785                 790                 795                 800

Lys His Gln His Gln Pro His Ser Val Cys Arg Ala Arg Lys Arg Thr
                805                 810                 815

Ser Leu Gly Ile Asn Lys Glu Lys Leu Arg Met Ser Leu Asn Gly Gly
            820                 825                 830

Glu Pro Ser Thr Lys Glu Val Leu Gln Thr Phe Ser Met Glu Lys Thr
                835                 840                 845

Arg Lys Ala Ala Leu Thr Ala Asn Ser Glu Gln Thr Asn Thr Ser Phe
850                 855                 860

Pro Ser Trp Arg Asp Arg Lys His Arg Lys Lys Ser Trp Gly Ser Ser
865                 870                 875                 880
```

```
Pro Val Arg Asp Ser Arg Ala Asn His His Arg Asp Asp Phe Gln Glu
            885                 890                 895

His Thr Val Ser Arg Ser Thr Leu Cys Glu Glu Pro Leu Ser Leu Asp
        900                 905                 910

Lys Gln Asn Ile Glu Phe Arg Ser Ser Gly Leu Leu Ile Lys Asn Ala
        915                 920                 925

Ser Phe Cys Ala Asn Glu Lys Tyr Asn Lys Thr Ser Phe Ser Leu Gln
        930                 935                 940

Met Gln Gln Pro Cys Leu Arg Lys Lys Thr Glu Ser Thr Gly Ala Val
945                 950                 955                 960

Glu His Ser Phe Ala Glu Ser Gln Ser Lys Asn Val Thr Gly Gln Ser
        965                 970                 975

Pro Gly Val Ala Ser Asn Gly Arg Glu Leu Ala Asp Thr Glu Thr Gly
        980                 985                 990

Lys Ile Asn Glu Val Leu Ile Glu  Asn Gly Ala Glu Ser  Gln Asn Val
        995             1000                 1005

Ser Val  Lys His His Asp Thr  His Pro Ile Ser Gln  Cys Leu Glu
    1010                 1015                 1020

Asn Gln  Cys Asp Lys Gln Thr  Asn Thr Cys Thr Lys  Arg Lys Ala
    1025                 1030                 1035

Leu Ile  Glu Arg Gln Val Ser  Cys Glu Ala Val Ser  Tyr Met Ala
    1040                 1045                 1050

Arg Asp  Ser Asn Asp Val Ser  Thr Ile Asn Ser Glu  Ser Ile Lys
    1055                 1060                 1065

Leu His  Ser Lys Asp Asp Glu  Ser Asn His Cys Gln  Val Leu Gly
    1070                 1075                 1080

Asn Asn  Thr Gly Arg Ser Glu  Ala Pro Arg Gly Leu  Leu Gln Ser
    1085                 1090                 1095

Ala Ala  Glu Phe Ser Gln Ala  Asp Gly Gln His Glu  His Leu Leu
    1100                 1105                 1110

Asn Ser  Ser Gly Ile Gln Glu  Lys Thr Asp Ala Tyr  Ala Thr Asn
    1115                 1120                 1125

Lys Thr  Glu His Asn His Val  Ser Asn Leu Ala Pro  Cys Asp Phe
    1130                 1135                 1140

Gly Asp  Ser Phe Tyr Leu Asp  Thr Gln Ser Glu Lys  Ile Ile Glu
    1145                 1150                 1155

Gln Leu  Ala Thr Glu His Ala  Lys Gln Arg Thr Lys  Ala Val Thr
    1160                 1165                 1170

Ala Lys  Gly Ser Asp Thr Arg  Asn Ser Gly Ser Ser  Phe Gln Asn
    1175                 1180                 1185

Lys Cys  His Ser Thr Arg Gly  Glu Gln His Phe Gln  Arg Ala Ala
    1190                 1195                 1200

Asn Thr  Asp His Leu Asp Ser  Lys Ser Val Glu Thr  Thr Lys Gln
    1205                 1210                 1215

Asn Pro  Glu Lys Ser Ile Gly  Arg Leu Thr Ala Glu  Ser Ile Ile
    1220                 1225                 1230

Phe His  Ser Pro Thr Pro Gln  Gly Glu Asn Gly Pro  Cys Phe Arg
    1235                 1240                 1245

Val Asn  Glu Gln Ser Val Thr  Asp Ser Gln Leu Asn  Ser Phe Leu
    1250                 1255                 1260

Gln Gly  Phe Glu Thr Gln Glu  Met Val Lys Pro Val  Leu Ser Leu
    1265                 1270                 1275

Ala Pro  Leu Ala Gly Thr Pro  Thr Gly Leu Glu Glu  Glu Asn Leu
```

-continued

```
                1280                1285                1290
Pro Glu Thr Ser Leu Asn Met Ser Asp Ser Ile Leu Phe Asp Ser
    1295                1300                1305
Phe Gly Glu Asp Asp Leu Val Lys Gly Gln Ser Pro Asp Val Gln
    1310                1315                1320
Ala Lys Gln Pro Leu Leu Ser Val Met Thr Pro Asn His Leu Ser
    1325                1330                1335
Ser Ser Leu Cys Pro Arg Glu Asp Pro Val Met Lys Ala Asn Val
    1340                1345                1350
Asn Asp His Gln Gly Ile Gln Gln Pro Glu Thr Cys Ser Ser Gly
    1355                1360                1365
Glu Ser Val Ile Phe Ser Glu Val Asp Ser Ala Gln Met Ile Glu
    1370                1375                1380
Ala Leu Asp Ser Val Ala Ala Leu His Val Gln Gln Asn Cys Asn
    1385                1390                1395
Ser Val Thr Leu Lys Thr Leu Glu Leu Ser Asp Ser Ala Met Leu
    1400                1405                1410
Asp Asn Glu Cys Pro Gln Gly Lys Val Ala Arg Gly Asp Lys Ser
    1415                1420                1425
Glu Arg Ala Gln Met Ser Lys Leu Thr Glu Thr Asn Gln Asp Asn
    1430                1435                1440
Ser Ile Thr Trp Ser Gly Ala Ser Phe Asp Leu Ser Pro Glu Leu
    1445                1450                1455
Gln Arg Ile Leu Asp Lys Gly Ser Ser Pro Leu Glu Asn Glu Arg
    1460                1465                1470
Pro Lys Leu Thr Gln Thr Asn Leu Ser Cys Phe Glu Arg Asn Gly
    1475                1480                1485
Thr Glu Leu Asn Glu Arg Gln Glu Met Asn Pro Asn Leu Glu Ala
    1490                1495                1500
Val Gln Ile Gln Arg Thr Ser Leu Phe Pro Asn Asn Gly Val Gln
    1505                1510                1515
Asn Lys Ile Glu Gly Ile Gly Asn Asp Thr Arg Arg Gly Glu Ala
    1520                1525                1530
Leu Tyr Pro Ser Ala Arg Lys Glu Ser Asp Thr Ala Asp Asp Asn
    1535                1540                1545
Gly Leu Ile Pro Pro Thr Pro Ile Leu Ala Ser Thr Ser Lys Leu
    1550                1555                1560
Ser Phe Pro Glu Ile Leu Gly Thr Ser Val Asn His Leu Lys Ala
    1565                1570                1575
Asp Ser Val Phe Leu Pro Gly Glu Ser Cys Leu Phe Gly Ser Pro
    1580                1585                1590
Ser Asp Ser Gln Glu Arg Arg Asp Ser Phe Lys Asp Asp Arg Ser
    1595                1600                1605
Val Gly Asp Thr Ser Phe Ser Leu Gln Phe Ser Gln Asp Glu Leu
    1610                1615                1620
Gln Leu Thr Pro Ala Ser Cys Ser Ser Glu Ser Leu Ala Ile Ile
    1625                1630                1635
Asp Val Ala Ser Asp His Thr Leu Phe Glu Thr Phe Val Lys Glu
    1640                1645                1650
Trp Arg Cys Gln Lys Arg Phe Ser Ile Ser Leu Ala Cys Glu Lys
    1655                1660                1665
Ile Arg Ser Pro Thr Ser Ser Lys Thr Ala Thr Ile Gly Gly Arg
    1670                1675                1680
```

```
Leu Lys Gln Val Ser Ser Pro Gln Lys Thr Ser Ala Glu Asp Asp
    1685            1690                1695

Gly Phe Pro Val His Gly Ser Asp Gly Val Ile Val Val Gly Leu
    1700            1705                1710

Ala Val Cys Trp Gly Gly Arg Asp Ala Tyr Tyr Leu Ser Leu Gln
    1715            1720                1725

Lys Glu Gln Lys His Ser Val Phe Pro Leu Arg Leu Leu Leu Gln
    1730            1735                1740

Leu Asn Glu Phe Asn Phe Tyr Ile Lys Thr Val Leu Phe Gln Glu
    1745            1750                1755

Ile Ser Pro Ser Leu Ala Pro Pro Pro Leu Asp Thr Thr Leu Thr
    1760            1765                1770

Val Glu Glu Arg Met Glu His Leu Gln Ser Cys Leu Gln Lys Lys
    1775            1780                1785

Ser Asp Lys Glu Gln Thr Val Val Thr Tyr Asp Phe Ile Gln Ser
    1790            1795                1800

Tyr Lys Ile Leu Leu Leu Ser Cys Gly Val Ser Leu Glu Pro Ser
    1805            1810                1815

Tyr Glu Asp Pro Lys Val Ala Cys Trp Leu Leu Asp Pro Asp Ser
    1820            1825                1830

Lys Glu Pro Thr Leu His Ser Ile Val Thr Ser Phe Leu Pro Glu
    1835            1840                1845

Glu Leu Pro Leu Leu Glu Gly Ile Glu Thr Gly Gln Gly Ile Gln
    1850            1855                1860

Ser Leu Gly Leu Asn Val Asp Thr Glu His Ser Gly Arg Tyr Arg
    1865            1870                1875

Ala Ser Val Glu Ser Ile Leu Ile Phe Asn Ser Met Asn Gln Leu
    1880            1885                1890

Asn Ser Leu Leu Gln Lys Glu Asn Leu His Asp Ile Phe Cys Lys
    1895            1900                1905

Val Glu Met Pro Ser Gln Tyr Cys Leu Ala Leu Leu Glu Leu Asn
    1910            1915                1920

Gly Ile Gly Phe Ser Thr Ala Glu Cys Glu Ser Gln Lys His Ile
    1925            1930                1935

Met Gln Ala Lys Leu Asp Ala Ile Glu Thr Gln Ala Tyr Gln Leu
    1940            1945                1950

Ala Gly His Ser Phe Ser Phe Thr Ser Ala Asp Asp Ile Ala Gln
    1955            1960                1965

Asp Val Leu Asn Lys Leu Lys Ala Leu His Pro Leu Pro Gly Leu
    1970            1975                1980

Ile Leu Glu Trp Arg Arg Ile Ser Asn Ala Ile Thr Lys Val Val
    1985            1990                1995

Phe Pro Leu Gln Arg Glu Lys Arg Leu Asn Pro Phe Leu Arg Met
    2000            2005                2010

Glu Arg Leu Tyr Pro Val Ser Gln Ser His Thr Ala Thr Gly Arg
    2015            2020                2025

Ile Thr Phe Ile Glu Pro Asn Ile Gln Asn Val Pro Arg Asp Phe
    2030            2035                2040

Glu Ile Lys Met Pro Thr Val Val Arg Glu Ser Pro Pro Ser Gln
    2045            2050                2055

Ala Pro Gly Lys Arg Leu Leu Pro Met Thr Arg Gly Gln Asn Lys
    2060            2065                2070
```

Lys Phe Tyr Gly Leu His Pro Gly Asn Gly Thr Leu Met Glu Glu
2075                2080                2085

Lys Ala Ser Asp Arg Gly Val Pro Phe Ser Val Ser Met Arg His
2090                2095                2100

Ala Phe Val Pro Phe Pro Val Asp Asn Leu Leu Glu Leu Arg Ile
2105                2110                2115

Leu Ala His Leu Ser Arg Asp Cys Arg Leu Ile Gln Val Leu Asn
2120                2125                2130

Thr Gly Ala Asp Val Phe Arg Ser Ile Ala Ala Glu Trp Lys Met
2135                2140                2145

Ile Glu Pro Asp Ser Val Gly Glu Asp Leu Arg Gln Gln Ala Lys
2150                2155                2160

Gln Ile Cys Tyr Gly Ile Ile Tyr Gly Met Gly Ala Lys Ser Leu
2165                2170                2175

Gly Glu Gln Met Gly Ile Lys Glu Asn Asp Ala Ala Cys Tyr Ile
2180                2185                2190

Asp Ser Phe Lys Ser Arg Tyr Thr Gly Ile Asn His Phe Leu Arg
2195                2200                2205

Asp Thr Val Lys Lys Cys Arg Arg Asp Gly Phe Val Gln Thr Ile
2210                2215                2220

Leu Gly Arg Arg Arg Tyr Leu Pro Gly Ile Lys Asp Asn Asn Pro
2225                2230                2235

Tyr His Lys Ala His Ala Glu Arg Gln Ala Ile Asn Thr Thr Val
2240                2245                2250

Gln Gly Ser Ala Ala Asp Ile Val Lys Thr Ala Thr Val Asn Ile
2255                2260                2265

Gln Lys Gln Leu Glu Thr Phe His Ser Ala Phe Lys Ser His Gly
2270                2275                2280

His Arg Glu Ser Met Leu Gln His Gly Gln Thr Gly Cys Gly Asp
2285                2290                2295

Leu Ser Pro Ser Pro Gly Gln Leu Val Gly Leu Leu Pro Lys Lys
2300                2305                2310

Lys Leu Lys Gly Met Phe Cys Pro Met Arg Gly Gly Phe Phe Ile
2315                2320                2325

Leu Gln Leu His Asp Glu Leu Leu Tyr Glu Val Ala Glu Glu Asp
2330                2335                2340

Val Val Gln Val Ala Gln Ile Val Lys Lys Glu Met Glu Cys Ala
2345                2350                2355

Val Lys Leu Ser Val Lys Leu Lys Val Lys Val Arg Met Gly Ala
2360                2365                2370

Ser Trp Gly Gln Leu Glu Asp Phe Asp Val
2375                2380

<210> SEQ ID NO 13
<211> LENGTH: 2530
<212> TYPE: PRT
<213> ORGANISM: Rattus norvegicus

<400> SEQUENCE: 13

Met Ser Leu Pro Arg Arg Ser Gly Lys Arg Arg Ser Ser Ser Gly
1               5                   10                  15

Ser Asp Ser Phe Ser Phe Ser Gly Asp Gly Asp Ser Cys Val Ser Pro
                20                  25                  30

Gln Leu Leu Cys Arg Pro Val Leu Ser Pro Pro Gly Leu Gly Arg
                35                  40                  45

```
Gly Arg Arg Leu Ala Gly Thr Gly Thr Cys Lys Gln Arg Val Ser Asp
     50                  55                  60

Asp Gln Ile Asp Gln Leu Leu Ala Asn Trp Gly Leu Pro Lys Ala
65                  70                  75                  80

Val Leu Glu Lys Tyr His Asn Phe Gly Val Lys Lys Met Phe Glu Trp
                 85                  90                  95

Gln Ala Glu Cys Leu Leu Gly Gln Val Leu Glu Gly Lys Asn Leu
             100                 105                 110

Val Tyr Ser Ala Pro Thr Ser Ala Gly Lys Thr Leu Val Ala Glu Leu
         115                 120                 125

Leu Ile Leu Lys Arg Val Leu Glu Thr Arg Lys Lys Ala Leu Phe Ile
     130                 135                 140

Leu Pro Phe Val Ser Val Ala Lys Glu Lys Lys Tyr Tyr Leu Gln Ser
145                 150                 155                 160

Leu Phe Gln Glu Val Gly Ile Lys Val Asp Gly Tyr Met Gly Ser Thr
                 165                 170                 175

Ser Pro Thr Gly Arg Phe Ser Ser Leu Asp Val Ala Val Cys Thr Ile
             180                 185                 190

Glu Arg Ala Asn Gly Leu Ile Asn Arg Leu Ile Glu Glu Asn Lys Met
         195                 200                 205

Asp Leu Leu Gly Thr Val Val Asp Glu Leu His Met Leu Gly Asp
210                 215                 220

Ser His Arg Gly Tyr Leu Leu Glu Leu Leu Leu Thr Lys Val Cys Phe
225                 230                 235                 240

Val Thr Arg Lys Ser Ala Ser Cys Gln Ala Asp Ser Ala Ser Ala Leu
                 245                 250                 255

Ala Cys Ala Val Gln Ile Val Gly Met Ser Ala Thr Leu Pro Asn Leu
             260                 265                 270

Gln Leu Val Ala Ser Trp Leu Asn Ala Glu Leu Tyr His Thr Asp Phe
         275                 280                 285

Arg Pro Val Pro Leu Leu Glu Ser Ile Lys Val Gly Asn Ser Ile Tyr
     290                 295                 300

Asp Ser Ser Met Lys Leu Val Arg Glu Phe Gln Pro Leu Leu Gln Val
305                 310                 315                 320

Lys Gly Asp Glu Asp His Ile Val Ser Leu Cys Tyr Glu Thr Val Arg
                 325                 330                 335

Asp Asn His Ser Val Leu Val Phe Cys Pro Ser Lys Lys Trp Cys Glu
             340                 345                 350

Lys Val Ala Asp Ile Ile Ala Arg Glu Phe Tyr Asn Leu His His Gln
         355                 360                 365

Pro Glu Gly Leu Val Lys Ser Ser Glu Phe Pro Pro Val Ile Leu Asp
     370                 375                 380

Gln Lys Ser Leu Leu Glu Val Ile Asp Gln Leu Lys Arg Ser Pro Ser
385                 390                 395                 400

Gly Leu Asp Ser Val Leu Lys Asn Thr Val Pro Trp Gly Val Ala Phe
                 405                 410                 415

His His Ala Gly Leu Thr Phe Glu Glu Arg Asp Ile Ile Glu Gly Ala
             420                 425                 430

Phe Arg Gln Gly Leu Ile Arg Val Leu Ala Ala Thr Ser Thr Leu Ser
         435                 440                 445

Ser Gly Val Asn Leu Pro Ala Arg Arg Val Ile Ile Arg Thr Pro Val
     450                 455                 460
```

-continued

Phe Gly Gly Gln Pro Leu Asp Ile Leu Thr Tyr Lys Gln Met Val Gly
465                 470                 475                 480

Arg Ala Gly Arg Lys Gly Val Asp Thr Met Gly Glu Ser Ile Leu Val
            485                 490                 495

Cys Lys Asn Ser Glu Lys Ser Lys Gly Ile Ala Leu Leu Gln Gly Ser
        500                 505                 510

Leu Glu Pro Val His Ser Cys Leu Gln Ser Gln Gly Glu Val Thr Ser
    515                 520                 525

Thr Met Ile Arg Ala Ile Leu Glu Ile Ile Val Ser Gly Val Ala Ser
530                 535                 540

Thr Ser Gln Asp Met Gln Thr Tyr Ala Ala Cys Thr Phe Leu Ala Ala
545                 550                 555                 560

Asp Val Lys Glu Gly Lys Gln Gly Ile Gln Arg Asn Arg Asp Asp Val
            565                 570                 575

Gln Arg Gly Ala Val Asp Ala Cys Val Thr Trp Leu Leu Glu Asn Glu
        580                 585                 590

Phe Ile Gln Ala Ala Glu Pro Ser Asp Gly Thr Gly Gly Lys Val Tyr
    595                 600                 605

His Pro Thr His Leu Gly Ser Ala Thr Leu Ser Ser Ser Leu Ser Pro
610                 615                 620

Thr Asp Thr Leu Asp Ile Phe Ala Asp Leu Gln Arg Ala Met Lys Gly
625                 630                 635                 640

Phe Val Leu Glu Asn Asp Leu His Ile Val Tyr Leu Val Thr Pro Val
            645                 650                 655

Phe Glu Asp Trp Thr Ser Ile Asp Trp Tyr Arg Phe Phe Cys Leu Trp
        660                 665                 670

Glu Lys Leu Pro Thr Ser Met Lys Arg Val Ala Glu Leu Val Gly Val
    675                 680                 685

Glu Glu Gly Phe Leu Ala Arg Cys Val Lys Gly Lys Val Val Ala Arg
690                 695                 700

Thr Glu Arg Gln His Arg Gln Met Ala Ile His Lys Arg Phe Phe Thr
705                 710                 715                 720

Ser Leu Val Leu Leu Asp Leu Ile Ser Glu Ile Pro Leu Lys Glu Ile
            725                 730                 735

Asn Gln Lys Tyr Gly Cys Asn Arg Gly Gln Ile Gln Ser Leu Gln Gln
        740                 745                 750

Ser Ala Ala Val Tyr Ala Gly Met Ile Thr Val Phe Ser Asn Arg Leu
    755                 760                 765

Gly Trp His Asn Met Glu Leu Leu Leu Ser Gln Phe Gln Lys Arg Leu
770                 775                 780

Thr Phe Gly Ile Gln Arg Glu Leu Cys Asp Leu Ile Arg Val Ser Ser
785                 790                 795                 800

Leu Asn Ala Gln Arg Ala Arg Phe Leu Tyr Ala Ser Gly Phe Leu Thr
            805                 810                 815

Val Ala Asp Leu Ala Arg Ala Asp Thr Val Glu Val Glu Ala Ala Leu
        820                 825                 830

Lys Asp Ala Leu Pro Phe Lys Ser Ala Arg Lys Ala Val Asp Glu Glu
    835                 840                 845

Glu Glu Ala Ala Glu Glu Arg Arg Ser Met Arg Thr Ile Trp Val Ala
850                 855                 860

Gly Lys Ser Leu Ser Ala Arg Glu Ala Ala Leu Ile Val Glu Glu
865                 870                 875                 880

Ala Lys Val Ile Leu Gln Gln Asp Leu Ile Glu Met Gly Val Gln Trp

```
                885                 890                 895
Gly Pro His Ser Pro Leu Ser Ser Thr His Ser Leu Thr Ser Gly
                900                 905                 910

Ser Glu Val Lys Glu His Thr Phe Lys Ser Gln Thr Lys Ser His
            915                 920                 925

Lys Arg Leu Ala Ser Lys Ser Arg Asn Ser Met Arg Val Ser Gly Ser
            930                 935                 940

Asn Gly Lys Gln Ser Pro Glu Ala Gly Gln Gly Leu Asp Glu Cys Arg
945                 950                 955                 960

Glu Arg Pro Asp Ser Leu Cys Lys Phe Gln Gly Asn His Glu Ile Gln
                965                 970                 975

Thr Pro Ser Val Tyr Arg Ala Arg Lys Arg Thr Ser Leu Gly Val Asn
                980                 985                 990

Lys Glu Met Leu Arg Thr Ser Leu  Lys Glu Gly Lys Pro  Ser Thr Lys
                995                 1000                1005

Glu Val  Leu Gln Thr Leu Ser  Phe Glu Lys Thr Arg  Lys Ala Ala
    1010                1015                1020

Leu Ser  Phe Ser Ser Glu Gln  Ala Asn Asn Ser Phe  Pro Ser Gly
    1025                1030                1035

Arg Asp  Arg Lys Tyr Arg Lys  Lys Ser Trp Gly Ser  Ser Pro Met
    1040                1045                1050

Ser Asp  Ser Val Met His Arg  Asp Asp Leu Gln Gly  Gln Thr Met
    1055                1060                1065

Cys Lys  Ser Thr Leu Cys Glu  Asp Pro Gln Lys Ser  Leu Glu Glu
    1070                1075                1080

Gln Asn  Thr Glu Tyr Arg Ser  Pro Gly Leu Phe Ala  Lys Asn Val
    1085                1090                1095

Ser Phe  Cys Ala Lys Glu Lys  Cys Asn Lys Thr Ser  Phe Pro Leu
    1100                1105                1110

Gln Met  Gln Gln Pro Cys Leu  Arg Arg Lys Pro Glu  Ser Gly Ala
    1115                1120                1125

Ala Val  Asp His Ser Val Ala  Val Ser Gln Asn Lys  Asn Val Val
    1130                1135                1140

Glu Gln  Pro Pro Gly Ala Pro  Arg Asp Arg Arg Gly  Leu Ala Ala
    1145                1150                1155

His Gly  Arg Ala Glu Val Asn  Glu Val Leu Thr Glu  Asn Gly Thr
    1160                1165                1170

Glu Ser  Gln Leu His Asp Thr  His Pro Val Ser Gln  Cys Leu Glu
    1175                1180                1185

Asn His  Ser Glu Lys Gln Thr  Asn Thr Cys Thr Arg  Gln Lys Thr
    1190                1195                1200

Leu Thr  Glu Gly Gln Ala Gly  Ile Ser His Val Thr  Arg Gly Ser
    1205                1210                1215

Asn Asp  Leu Thr Pro Ile Arg  Cys Glu Arg Leu Lys  Leu Asn Ser
    1220                1225                1230

Lys Glu  His Asp Ser Asn Pro  Cys Pro Gln Ala Leu  Gly Thr Asn
    1235                1240                1245

Ala Gly  Arg Thr Glu Ala Pro  Gln Ser Ser Glu Ala  Leu Gly Gln
    1250                1255                1260

Ala Gly  Gly Gln Cys Glu Asn  Leu Leu Asn Ser Pro  Gly Ile Gln
    1265                1270                1275

Glu Lys  Thr Ser Ala His Ala  Thr Asn Lys Thr Glu  His Ser His
    1280                1285                1290
```

-continued

Val Ala Asn Gln Ala Phe Cys Asp Phe Gly Asp Ser Leu Tyr Leu
1295            1300                1305

Asp Thr Gln Ser Glu Glu Ile Ile Glu Gln Met Ala Thr Lys Asn
1310            1315                1320

Ala Thr Gln Gly Ala Glu Ala Gly Ile Thr Glu Glu Gly Ser
1325            1330                1335

Ala Thr Gln Asn Glu Pro His Ser Thr Thr Gly Gly Gln His Ile
1340            1345                1350

Pro Gly Ala Ala Asn Thr Asp His Val Asp Arg Lys Asn Thr Glu
1355            1360                1365

Ser Val Lys Glu Asn Pro Lys Asn Ile Asp Arg Arg Thr Pro
1370            1375                1380

His Ser Leu Ile Phe His Ser Pro Thr Pro Gln Gly Gly Asn Ser
1385            1390                1395

Ala Cys Phe Lys Glu Asn Glu His Ser Val Thr Asp Ser Gln Leu
1400            1405                1410

Asn Ser Phe Leu Gln Gly Leu Glu Thr Gln Asp Lys Pro Ile Ile
1415            1420                1425

Pro Leu Ala Pro Gln Met Arg Thr Ser Thr Gly Val Glu Glu Glu
1430            1435                1440

Ser Leu Pro Glu Thr Ser Leu Asn Met Ser Asp Ser Ile Leu Phe
1445            1450                1455

Asp Ser Phe Gly Glu Asp Ser Phe Gly Gln Arg Gln Ser Leu Asp
1460            1465                1470

Val Lys Ala Lys Gln Pro Leu Leu Ser Glu Met Thr Pro Asn His
1475            1480                1485

Phe His Asn Pro Pro Tyr Pro Gln Glu Asp Pro Val Met Thr Pro
1490            1495                1500

His Met Ser Glu Pro Gln Gly Thr Leu Glu Arg Met Ala Cys Leu
1505            1510                1515

Ser Gly Glu Ser Ile Ile Phe Ser Glu Ile Asp Ser Ala Gln Val
1520            1525                1530

Ile Glu Ala Leu Asp Asn Met Ala Ala Phe Tyr Met Gln Glu Asn
1535            1540                1545

Cys Asn Pro Ile Thr Leu Lys Thr Glu Pro Arg Asp Leu Ala Ala
1550            1555                1560

Leu Gly Asn Glu Cys Pro Gln Gly Glu Val Val Arg Gly Glu Gln
1565            1570                1575

His Glu Gly Ser Ser Lys Pro Lys Phe Met Glu Ile Asn Gln Asp
1580            1585                1590

Asn Ser Phe Thr Trp Ser Ala Ala Ser Phe Asn Leu Ser Pro Glu
1595            1600                1605

Leu Gln Arg Ile Leu Asp Lys Val Ser Thr Pro Arg Glu Asn Glu
1610            1615                1620

Glu Pro Glu Leu Met His Ala Asp Leu Ser Cys Phe Glu Glu Asn
1625            1630                1635

Ser Thr Glu Ser His Glu Arg Gln Asp Met Asn Ser Asp Leu Gly
1640            1645                1650

Thr Val Gln Arg Thr Ser Phe Leu Pro Ser Asn Gly Val Lys Ser
1655            1660                1665

Arg Thr Glu Gly Leu Glu Ser Lys Ala Lys His Gly Gly Ala Ser
1670            1675                1680

```
Ser Ala Leu Pro His Lys Ala Ala Asp Asp Asn Gly Leu Ile
1685                1690                1695

Pro Pro Thr Pro Leu Pro Ala Ser Ala Ser Ala Ser Lys
    1700                1705                1710

Leu Ala Leu Pro Glu Ile Leu Gly Thr Ser Val Lys His Gln Lys
        1715                1720                1725

Ala Ser Cys Leu Phe Asp Ser Pro Ser Asp Asn Gln Asn Gln Asp
        1730                1735                1740

Leu Ser Gln Glu Leu Arg Asp Ser Leu Lys Asp Ser Asp Gly Ser
    1745                1750                1755

Val Val Asp Thr Ser Phe Phe Leu Gln Ser Gln Asp Gly Leu Leu
    1760                1765                1770

Leu Thr Gln Ala Ser Cys Ser Ser Glu Ser Leu Ala Ile Ile Asp
    1775                1780                1785

Val Ala Ser Asp Gln Ile Leu Phe Gln Thr Phe Val Lys Glu Trp
    1790                1795                1800

Gln Cys Gln Lys Arg Phe Ser Ile Ser Leu Ala Cys Glu Lys Met
    1805                1810                1815

Thr Ser Ser Thr Ser Ser Lys Thr Ala Thr Ile Gly Gly Arg Leu
    1820                1825                1830

Lys Gln Val Asn Ser Pro Gln Glu Ala Ser Val Glu Asp Asp Gly
    1835                1840                1845

Phe Pro Val His Gly Ser Asp Cys Ala Val Val Gly Leu Ala
    1850                1855                1860

Val Cys Trp Gly Gly Lys Asp Ala Tyr Tyr Leu Ser Leu Gln Lys
    1865                1870                1875

Glu Gln Lys Gln Ser Glu Met Ser Pro Ser Leu Ala Pro Pro Pro
    1880                1885                1890

Leu Asp Ala Thr Leu Thr Val Lys Glu Arg Met Glu Tyr Leu Gln
    1895                1900                1905

Ser Cys Leu Gln Lys Lys Ser Asp Gln Glu Arg Ser Val Val Thr
    1910                1915                1920

Tyr Asp Phe Ile Gln Thr Tyr Lys Val Leu Leu Leu Ser Cys Gly
    1925                1930                1935

Ile Ser Leu Glu Pro Ser Tyr Glu Asp Pro Lys Val Ala Cys Trp
    1940                1945                1950

Leu Leu Asp Pro Asp Ser Lys Glu Pro Thr Leu His Ser Ile Val
    1955                1960                1965

Thr Ser Phe Leu Pro His Glu Leu Ala Leu Leu Glu Gly Ile Glu
    1970                1975                1980

Thr Gly Pro Gly Ile Gln Ser Leu Gly Leu Asn Val Asn Thr Asp
    1985                1990                1995

His Ser Gly Arg Tyr Arg Ala Ser Val Glu Ser Val Leu Ile Phe
    2000                2005                2010

Asn Ser Met Asn Gln Leu Asn Ser Met Leu Gln Lys Glu Asn Leu
    2015                2020                2025

His Asp Ile Phe Cys Lys Val Glu Met Pro Ser Gln Tyr Cys Leu
    2030                2035                2040

Ala Leu Leu Glu Leu Asn Gly Ile Gly Phe Ser Thr Ala Glu Cys
    2045                2050                2055

Glu Thr Gln Lys His Ile Met Gln Ala Lys Leu Asp Ala Ile Glu
    2060                2065                2070

Thr Gln Ala Tyr Gln Leu Ala Gly His Ser Phe Ser Phe Thr Ser
```

```
            2075                2080                2085
Ala Asp Asp Ile Ala Gln Val Leu Phe Leu Glu Leu Lys Leu Pro
        2090                2095                2100

Pro Asn Gly Glu Met Lys Thr Gln Gly Gly Arg Lys Thr Leu Gly
        2105                2110                2115

Ser Thr Arg Arg Gly Thr Glu Ser Asp Arg Lys Leu Arg Leu Gly
        2120                2125                2130

Arg Arg Phe Ser Thr Ser Lys Asp Ile Leu Asn Lys Leu Lys Asp
        2135                2140                2145

Leu His Pro Leu Pro Gly Leu Ile Leu Glu Trp Arg Arg Ile Ser
        2150                2155                2160

Asn Ala Ile Thr Lys Val Val Phe Pro Leu Gln Arg Glu Lys His
        2165                2170                2175

Leu Asn Pro Phe Leu Arg Met Glu Arg Ile Tyr Pro Val Ser Gln
        2180                2185                2190

Ser His Thr Ala Thr Gly Arg Ile Thr Phe Thr Glu Pro Asn Ile
        2195                2200                2205

Gln Asn Val Pro Arg Asp Phe Glu Ile Lys Met Pro Thr Leu Val
        2210                2215                2220

Arg Glu Ser Pro Pro Ser Gln Ala Ser Gly Lys Gly Gln Leu Ala
        2225                2230                2235

Met Ala Arg Gln Asn Gln Lys Val Tyr Gly Leu His Pro Gly Gln
        2240                2245                2250

Arg Thr Val Leu Glu Lys Thr Ser Asp Arg Gly Val Pro Phe Ser
        2255                2260                2265

Val Ser Met Arg His Ala Phe Val Pro Phe Pro Gly Gly Leu Ile
        2270                2275                2280

Leu Ala Ala Asp Tyr Ser Gln Leu Glu Leu Arg Ile Leu Ala His
        2285                2290                2295

Leu Ser Arg Asp Cys Arg Leu Ile Gln Val Leu Asn Ser Gly Ala
        2300                2305                2310

Asp Val Phe Arg Ser Ile Ala Ala Glu Trp Lys Met Ile Glu Pro
        2315                2320                2325

Asp Ala Val Gly Asp Asn Leu Arg Gln Gln Ala Lys Gln Ile Cys
        2330                2335                2340

Tyr Gly Ile Ile Tyr Gly Met Gly Ala Lys Ser Leu Gly Glu Gln
        2345                2350                2355

Met Gly Ile Lys Glu Asn Asp Ala Ala Cys Tyr Ile Asp Ser Phe
        2360                2365                2370

Lys Ser Arg Tyr Lys Gly Ile Asn His Phe Met Arg Asp Thr Val
        2375                2380                2385

Lys Asn Cys Arg Arg Asp Gly Phe Val Glu Thr Ile Leu Gly Arg
        2390                2395                2400

Arg Arg Tyr Leu Pro Gly Ile Lys Asp Asn Asn Pro Tyr His Lys
        2405                2410                2415

Ala His Ala Glu Arg Gln Ala Ile Asn Thr Thr Val Gln Gly Ser
        2420                2425                2430

Ala Ala Asp Ile Val Lys Val Ala Thr Val Asn Ile Gln Lys Gln
        2435                2440                2445

Leu Glu Thr Phe His Pro Thr Phe Lys Ser His Gly His Arg Glu
        2450                2455                2460

Ser Met Leu Gln Ser Asp Arg Ala Gly Leu Leu Pro Lys Arg Lys
        2465                2470                2475
```

```
Val Lys Gly Met Phe Cys Pro Met Arg Gly Gly Phe Phe Ile Leu
    2480            2485                2490

Gln Leu His Asp Glu Leu Leu Tyr Glu Val Ala Glu Glu Asp Val
    2495                2500                2505

Val Gln Val Ala Gln Ile Val Lys Asn Glu Met Glu Cys Ala Ile
2510            2515                2520

Lys Leu Ser Val Lys Leu Lys
    2525            2530

<210> SEQ ID NO 14
<211> LENGTH: 2577
<212> TYPE: PRT
<213> ORGANISM: Alligator sinensis

<400> SEQUENCE: 14

Met Ala Phe Phe Ser Lys Gly Gln Cys Gln Arg Met Asn Ile Pro Glu
1               5                   10                  15

Asp Gln Ala Asp Lys Leu Leu Leu Ala Ser Trp Gly Leu Pro Lys Ala
            20                  25                  30

Val Leu Glu Lys Tyr His Ser Leu Gly Val Val His Met Phe Lys Trp
        35                  40                  45

Gln Ala Glu Cys Leu Met Leu Gly Gln Val Leu Glu Gly Lys Asn Leu
    50                  55                  60

Val Tyr Ser Ala Pro Thr Ser Ala Gly Lys Thr Leu Val Ala Glu Leu
65                  70                  75                  80

Leu Ile Leu Lys Arg Val Leu Glu Thr His Lys Lys Ala Leu Phe Ile
                85                  90                  95

Leu Pro Phe Val Ser Val Ala Lys Glu Lys Lys Tyr Tyr Leu Gln Ala
            100                 105                 110

Leu Phe Gln Glu Val Gly Val Arg Val Glu Gly Tyr Met Gly Ser Thr
        115                 120                 125

Ser Pro Ala Gly Arg Phe Ser Thr Leu Asp Val Ala Val Cys Thr Ile
    130                 135                 140

Glu Arg Ala Asn Gly Leu Ile Asn Arg Leu Ile Glu Glu Asn Gln Met
145                 150                 155                 160

Asp Leu Leu Gly Met Val Val Asp Glu Leu His Met Leu Gly Asp
            165                 170                 175

Ser His Arg Gly Tyr Leu Leu Glu Leu Leu Leu Thr Lys Val Arg Phe
            180                 185                 190

Ile Thr Glu Lys Val Thr Lys Arg Gln Ala Lys Ala Ser Ser Pro Ala
        195                 200                 205

Phe Gly Gly Ile Gln Ile Val Gly Met Ser Ala Thr Leu Pro Asn Leu
    210                 215                 220

His Leu Leu Ala Ser Trp Leu Asn Ala Glu Leu Tyr His Thr Asp Phe
225                 230                 235                 240

Arg Pro Val Pro Leu Met Glu Trp Val Lys Ile Gly Ser Asn Ile Tyr
                245                 250                 255

Asp Ser Ser Met Asn Leu Val Arg Glu Phe Gln Pro Met Leu Gln Leu
            260                 265                 270

Lys Gly Asp Glu Asp His Val Ser Leu Cys Tyr Glu Thr Val Arg
        275                 280                 285

Asp Gly His Ser Val Leu Leu Phe Cys Pro Ser Lys Asn Trp Cys Glu
    290                 295                 300

Lys Leu Ala Asn Ile Ile Ala Arg Glu Phe Cys Asn Leu Gln Leu Ser
```

```
            305                 310                 315                 320
Asp Arg Lys Thr Ser Asn Leu Pro Pro Ile Pro Leu Tyr Lys Glu Ala
                325                 330                 335

Ile Glu Glu Val Met Asp Gln Leu Arg Arg Ser Leu Ser Gly Leu Asp
                340                 345                 350

Ser Val Leu Gln Arg Thr Leu Pro Trp Gly Val Ala Phe His His Ala
                355                 360                 365

Gly Leu Thr Phe Asp Glu Arg Asp Val Ile Glu Gly Ala Phe Arg Gln
            370                 375                 380

Gly Leu Ile Arg Val Leu Ala Ala Thr Ser Thr Leu Ser Ser Gly Val
385                 390                 395                 400

Asn Leu Pro Ala Arg Arg Val Ile Ile Arg Thr Pro Val Phe Gly Gly
                405                 410                 415

Lys Leu Leu Asp Ile Leu Ala Tyr Lys Gln Met Ala Gly Arg Ala Gly
                420                 425                 430

Arg Lys Gly Ala Asp Thr Val Gly Glu Ser Ile Leu Val Cys Lys Pro
            435                 440                 445

Ser Glu Arg Ser Lys Gly Ile Ala Leu Leu Gln Gly Ser Leu Lys Pro
            450                 455                 460

Val Arg Ser Cys Leu Leu Arg Arg Glu Gly Glu Gly Ile Thr Ser Ser
465                 470                 475                 480

Met Ile Arg Ala Ile Leu Glu Ile Ile Val Gly Gly Val Ala Ser Thr
                485                 490                 495

Pro Asp Asp Val Arg Thr Tyr Ala Ser Cys Thr Leu Leu Val Ala Ser
            500                 505                 510

Leu Lys Asp Asn Glu Gln Gly Ser Glu Lys Asn Glu Asp Gly Val Gln
            515                 520                 525

Asn Gly Ala Ile Glu Ala Cys Val Ala Trp Leu Leu Gln Asn Glu Phe
            530                 535                 540

Ile Gln Val Ser Gly Pro Ser Asp Gly Val Lys Ala Glu Val Tyr Cys
545                 550                 555                 560

Pro Thr His Leu Gly Ser Ala Thr Leu Ser Ser Ser Leu Ser Pro Met
                565                 570                 575

Glu Ala Leu Glu Ile Phe Ala Asp Leu Gln Arg Ala Met Lys Gly Phe
                580                 585                 590

Val Leu Glu Asn Asp Leu His Ile Val Tyr Leu Val Thr Pro Val Tyr
                595                 600                 605

Glu Glu Trp Thr Thr Ile Asp Trp Tyr Gln Phe Phe Cys Leu Trp Glu
            610                 615                 620

Lys Leu Pro Ala Ser Met Lys Arg Val Ala Glu Leu Val Gly Ile Glu
625                 630                 635                 640

Glu Gly Phe Leu Ala Arg Ser Val Lys Gly Lys Ile Ile Ala Lys Thr
                645                 650                 655

Glu Lys Gln His Arg Gln Met Ala Ile His Lys Arg Phe Phe Thr Ser
            660                 665                 670

Leu Ala Leu Leu Asp Leu Ile Ser Glu Val Pro Leu Lys Asp Ile Thr
            675                 680                 685

Lys Arg Tyr Gly Cys Ser Arg Gly Gln Leu Gln Ser Leu Gln Gln Ser
            690                 695                 700

Ala Ala Thr Tyr Ala Gly Met Val Thr Val Phe Ser Asn Arg Leu Gly
705                 710                 715                 720

Trp His Asn Met Glu Gln Leu Leu Ser Gln Phe Gln Ser Arg Leu Thr
                725                 730                 735
```

-continued

```
Phe Gly Val His Arg Glu Leu Cys Asp Leu Val Arg Val Ser Leu Leu
            740                 745                 750

Asn Ala Gln Arg Ala Arg Ala Leu Tyr Asn Thr Gly Phe Ile Thr Val
            755                 760                 765

Ala Asp Leu Ala Lys Ala Asn Pro Ala Asp Val Glu Thr Ala Leu Lys
        770                 775                 780

Thr Thr Val Pro Phe Lys Ser Leu Arg Arg Ala Val Asp Glu Asp Glu
785                 790                 795                 800

Glu Ala Ala Glu Glu Arg Arg Asn Ala Arg Cys Ile Trp Met Ala Gly
                805                 810                 815

Met Lys His Val Thr Glu Asn Glu Ala Ala Ser Leu Val Glu Glu
            820                 825                 830

Ala Arg Met Leu Leu Gln Gln Asp Leu Ala Val Met Gly Val Gln Trp
                835                 840                 845

Asn Pro Asp Ser Tyr Leu Asp Ser Glu Ser Ser Ser Met Ile Ser
    850                 855                 860

Ser Glu Ser Glu Leu Glu Asp Arg Lys Tyr Arg Leu Ser Arg Glu Gly
865                 870                 875                 880

Ser Phe Glu Thr Leu Lys Ala Phe Asn Lys Glu Arg Tyr Gly Leu His
                885                 890                 895

Pro Asn Ser Gln Ser Gly Thr Ser Ala Lys Ile Glu Lys Gly Asn Lys
            900                 905                 910

Arg Leu Leu Gly Ala Ser Thr Pro Lys Gly Arg Leu Gln Ser Glu Ala
            915                 920                 925

Gln Ile Asp Gln Ile Gln Thr Glu Glu Gly Asn Ile Asp Val Ile Val
        930                 935                 940

Gln Ser Ala Arg Lys Arg Pro His Leu Ser Lys Asp Lys Glu Asn Met
945                 950                 955                 960

Glu Phe Thr Ser Lys Arg Lys Ser Lys Ala Gly Phe Arg Glu Thr Ser
                965                 970                 975

Gln Glu Ser Pro Thr Glu Glu Gly Lys Arg Pro Thr Leu Ser Phe Val
            980                 985                 990

Pro Thr Lys Thr Ser Ala Val Cys Arg Pro Arg Arg Ile Met Gly Gly
            995                 1000                1005

Ser Leu Asn Gln Ser Arg Asn Cys Ser Arg Ala Leu Lys Gln His
    1010                1015                1020

Arg Ser Leu Leu Glu Glu Ser Arg Arg Gln Ile Thr Gly Ile Lys
    1025                1030                1035

Gly Pro Pro Leu Ser Arg His Ser Ser Ser Glu Ser Lys Ser Phe
    1040                1045                1050

Pro Asp Gly Ser Asn Lys Glu Leu Thr Glu Lys Gly Ser Leu Val
    1055                1060                1065

His Lys Asp Lys Ile Ser Gly Ser Phe His Glu His Tyr Pro Leu
    1070                1075                1080

Ile Gly Ser Lys Glu Lys Met Glu Gly Leu Leu Met Glu Pro Ser
    1085                1090                1095

Val Thr Asn Glu Cys Lys Pro Lys Glu Lys Thr Ile Cys Gln Ala
    1100                1105                1110

Ser Arg Asp Val Ile Met Arg Asp Ala Ala Thr Val Arg Met Glu
    1115                1120                1125

Thr Ser Asp Thr Val Gly Gly Leu Met Ile Pro Ser Arg Glu Leu
    1130                1135                1140
```

-continued

```
Lys Asn Glu Asn Ile Gly Ala Lys Asp Ser Lys Val His Ala Gly
1145                1150                1155

Lys Lys Tyr Ala Lys Arg Ile Ser Gly Lys Gln Gln Met Ile Leu
1160                1165                1170

Asp Thr Asp Leu Cys Asn Glu Ile Val Ser Ser Ala Lys Thr
1175                1180                1185

His Val Ser Asp Gly Ala Tyr Lys Gln Lys Thr Val Cys Tyr Glu
1190                1195                1200

Pro Lys Ser Cys Leu Phe Pro Ile Gln Ser Lys Ser Lys His Ser
1205                1210                1215

Ser Glu Ser Pro Asn Gly Val Leu Phe Lys Ser Gly Val Gly
1220                1225                1230

Lys Ala Ala Asp Asn Gln Pro Glu Asp Phe Leu Arg Asp Ser Ile
1235                1240                1245

Ile Lys Ser Arg Ala Val Cys Ile Ala Lys Ser Lys Asn Gly
1250                1255                1260

Tyr Ala His Asp Leu Ser Leu Gly Tyr Gly Tyr Phe Glu Asp Ser
1265                1270                1275

Phe Gln Leu Asp Thr Gln Thr Asp Arg Ile Ile Gln Gln Gln Val
1280                1285                1290

Ala Ser Glu Ile Ala Gly His Gln Gly Ala Lys Gly Thr Glu Leu
1295                1300                1305

Ala Ala Ile Ala Val Gln Lys Thr Phe Thr Lys Leu Pro Cys Asp
1310                1315                1320

Asn Ala Phe Gln Thr Glu Ser Val Ala Asp Lys Asn Leu Val Ala
1325                1330                1335

Ala Phe Arg Glu Met Asp Ser Ser Gly Leu Val Thr Thr Leu Gly
1340                1345                1350

Met Lys Gln Pro Thr Asp Leu Cys Cys Ser Asp Lys Thr Leu Gly
1355                1360                1365

Ser Val Ser Ser Cys Leu Gln Ser Ala Val Lys Phe Pro Asp Ala
1370                1375                1380

Ala Leu Cys Leu Arg Gly Asn Asp Phe Ser Val Thr Asp Ser Gln
1385                1390                1395

Leu His Ser Phe Leu Gln Gly Tyr Leu Thr Gln Pro Ser Val Lys
1400                1405                1410

Glu Ser Val Cys Leu Gly Leu Gln Asn Gly Ala Pro Val Ser Asn
1415                1420                1425

Gly Gln Asn Pro His Ile Ile His Val Gln Val Glu Cys His Pro
1430                1435                1440

Ile Pro Glu Thr Ser Leu Asn Thr Ser Asn Ser Leu Leu Phe Glu
1445                1450                1455

Asp Ser Phe Ser Asp Leu Asn Asp Pro Ser Gly Ile Arg Ala Gly
1460                1465                1470

Glu Ala Glu Gly Val Glu Thr Arg Glu Gln Glu Ile Leu Pro Phe
1475                1480                1485

Pro Pro Asn Thr Ile Ser Ser Leu Val Gly Cys Leu His Gln
1490                1495                1500

Gln Ser Trp Gly Pro Ile Gln Asp Val Trp Ser Ile Asn Gln Val
1505                1510                1515

Glu Glu Gln Gln Pro Pro Gln Cys Asn Asp Ala Ser Leu Thr Phe
1520                1525                1530

Ser Glu Ile Asp Ser Phe Gln Leu Ala Glu Ala Phe Asp Asn Val
```

```
            1535                1540                1545

Ser Ser Pro Pro Phe Gln Gly Asp Leu Pro Ser Ala Ala Leu Val
    1550                1555                1560

Glu Pro Glu Leu Arg Lys Ser Val Ala Gln Glu Asp Ser Gly Pro
    1565                1570                1575

Met Asp Ile Lys Gly Asp Lys Ser Val Arg Pro Gln Lys Ala Gln
    1580                1585                1590

Gln Asn Val Lys Lys Asn Pro Asn Ser Ile Val Trp Ser Glu His
    1595                1600                1605

Ser Phe Glu Leu Ser Pro Gly Leu Gln Glu Ile Leu Asp Lys Trp
    1610                1615                1620

Pro Ser Pro Ser Gly Asn Lys Pro Ala Ser Ser Pro Ser Ile
    1625                1630                1635

Pro Gly Ser Lys Glu Lys Leu Val Leu Ser Asn Cys Ser Gln Glu
    1640                1645                1650

Gln Gly Ala Val Phe Glu Phe Gly Cys Gly Gln Lys Lys Pro Leu
    1655                1660                1665

Pro Leu Cys Gln Gly Leu Glu Asn Tyr Phe Thr Gly Arg Glu Ser
    1670                1675                1680

Asn Arg Gly Ala Leu Glu Gln Lys Pro Asn Cys Ser Pro Lys Phe
    1685                1690                1695

Leu Lys Gly Ser Ser Arg Lys Arg Asp Pro Gln Pro Asp Ile Ser
    1700                1705                1710

Asn Gly Leu Ile Pro Pro Thr Pro Pro Met Glu Pro Ala Pro Lys
    1715                1720                1725

Ser Phe Gly Met Ser Ser Leu Lys Ser Gly Lys Lys Lys Asp Val
    1730                1735                1740

Ile Leu Met Asn Glu Gly Pro Leu Cys Gln Val Leu Gln Asn Gly
    1745                1750                1755

Ile Pro Val Ser Asp Gln Gln Ile Glu Thr Leu Gln Phe Asn Pro
    1760                1765                1770

Glu Asn Gly Asp Pro Leu Glu Ile Asp Pro Val Lys Glu Asp Ser
    1775                1780                1785

Val Ile Asp Gln Asp Phe Ser Leu Gln Leu Ser Gln Asp Ile Leu
    1790                1795                1800

Pro Leu Ile Ser Cys Ser Ala Glu Ser Phe Thr Ile Ile Asp Val
    1805                1810                1815

Ala Ser Asp Met Ala Leu Phe Gln Thr Phe Ile Gln Glu Trp Arg
    1820                1825                1830

Asn Lys Asn Arg Phe Ala Ile Ser Val Ala Cys Glu Arg Thr Lys
    1835                1840                1845

Arg Leu Leu Ser Ser Arg Ser Thr Ile Gly Gly Arg Phe Lys Gln
    1850                1855                1860

Val Arg Ser Pro Gln Gln Ile Gln Val Lys Asp Asp Gly Phe Pro
    1865                1870                1875

Ile Lys Gly Cys Glu Asp Thr Leu Ile Val Gly Leu Ala Val Cys
    1880                1885                1890

Trp Gly Gly Lys Asp Ala Tyr Tyr Val Ser Leu Gln Gln Lys Ala
    1895                1900                1905

Asp Asp Gln Ala Glu Val Ser Ala Ser Leu Ala Pro Pro Ala Leu
    1910                1915                1920

Asp Gln Asn Leu Ser Val Thr Glu Arg Leu Cys His Leu Gln Ser
    1925                1930                1935
```

```
Cys Leu Gln Lys Glu Pro Glu Gly Lys His Cys Leu Val Met Tyr
    1940            1945            1950

Asp Phe Ile Gln His Tyr Lys Thr Leu Leu Met Ala Cys Gly Ile
    1955            1960            1965

Ser Leu Glu Gly Ser Phe Glu Asp Pro Lys Val Ala Cys Trp Leu
    1970            1975            1980

Leu Asp Pro Gly Ser Lys Glu Arg Thr Leu His Asn Met Val Thr
    1985            1990            1995

Ser Phe Leu Pro His Glu Leu Pro Leu Leu Glu Gly Ile Gly Thr
    2000            2005            2010

Gly Gln Gly Val Gln Ser Leu Gly Leu Ser Ala Ser Ala Asp His
    2015            2020            2025

Ser Gly Arg Tyr Arg Ala Ala Val Glu Ser Val Leu Ile Phe Gly
    2030            2035            2040

Ile Met Asn Gln Leu Asn Thr Leu Leu Gln Lys Glu Asn Leu Thr
    2045            2050            2055

Asp Ala Phe Cys Lys Val Glu Met Pro Thr Gln Tyr Cys Leu Ala
    2060            2065            2070

Leu Leu Glu Leu Asn Gly Ile Gly Phe Ser Thr Val Ala Cys Glu
    2075            2080            2085

Thr Gln Lys His Ile Met Gln Ala Lys Leu Asn Glu Ile Glu Thr
    2090            2095            2100

Gln Ala Tyr Gln Leu Ala Gly His Ser Phe Ser Leu Thr Ser Pro
    2105            2110            2115

Asp Asp Ile Ala Glu Val Leu Phe Leu Glu Leu Lys Leu Pro Asn
    2120            2125            2130

Gly Asp Val Lys Ala Gln Gly Asn Lys Lys Thr Leu Gly Tyr Thr
    2135            2140            2145

Arg Arg Cys Thr Thr Lys Gly His Arg Ile Arg Leu Gly Lys Gln
    2150            2155            2160

Phe Ser Thr Thr Lys Asp Ala Leu Glu Lys Leu Lys Thr Leu His
    2165            2170            2175

Pro Leu Pro Gly Leu Ile Leu Glu Trp Arg Arg Ile Thr Asn Ala
    2180            2185            2190

Val Thr Lys Val Val Phe Pro Leu Gln Arg Glu Lys Arg Leu Asn
    2195            2200            2205

Ser Leu Leu Gly Met Glu Arg Ile Tyr Pro Ile Ser Gln Thr His
    2210            2215            2220

Thr Ala Thr Gly Arg Ile Ser Phe Ala Glu Pro Asn Ile Gln Asn
    2225            2230            2235

Val Pro Lys Asp Phe Glu Ile Glu Met Pro Thr Leu Val Glu Glu
    2240            2245            2250

Ser Pro Pro Ser Gln Ala Arg Arg Asn Val Ser Ala Leu Pro Gly
    2255            2260            2265

Ala Arg Ser Arg Lys His His Ser Ile Leu Pro Gln Gly Ser Asn
    2270            2275            2280

Ser Val Ala Glu Glu Gly Pro Lys Gly Arg Gly Met Pro Phe Ser
    2285            2290            2295

Val Ser Met Arg His Ala Phe Val Pro Phe Pro Gly Gly Leu Ile
    2300            2305            2310

Leu Ala Ala Asp Tyr Ser Gln Ile Glu Leu Arg Ile Leu Ala His
    2315            2320            2325
```

```
Leu Ser Gly Asp Arg Arg Leu Ile Gln Ala Leu Asn Ser Gly Ala
    2330                2335                2340

Asp Val Phe Lys Ser Ile Ala Ala Glu Trp Lys Met Ile Asp Pro
    2345                2350                2355

Glu Ala Val Arg Asp Asp Thr Arg Gln Gln Ala Lys Gln Ile Cys
    2360                2365                2370

Tyr Gly Ile Ile Tyr Gly Ile Gly Ala Lys Ser Leu Gly Glu Gln
    2375                2380                2385

Met Gly Val Glu Glu Asn Asp Ala Ala Ser Tyr Ile Asp Ser Phe
    2390                2395                2400

Lys Ser Arg Tyr Lys Gly Ile Gln Lys Phe Leu Arg Glu Thr Val
    2405                2410                2415

Asn Asn Cys Ser Arg Asp Gly Phe Val Lys Thr Ile Leu Gly Arg
    2420                2425                2430

Arg Arg Tyr Leu Pro Ala Ile Arg Asp Pro Asn Pro Tyr Ser Lys
    2435                2440                2445

Ala His Ala Glu Arg Gln Ala Val Asn Thr Thr Val Gln Gly Ser
    2450                2455                2460

Ala Ala Asp Leu Val Lys Thr Ala Thr Val Asn Ile Gln Arg Arg
    2465                2470                2475

Leu Glu Ala Phe Pro Ser Thr Ile Lys Ser His Gly His Leu Glu
    2480                2485                2490

Ser Ser Phe Gln Met Asp Arg Ala Gly Arg Leu Glu Arg Arg Arg
    2495                2500                2505

Asn Arg Arg Met Leu His Pro Ile Thr Gly Gly Phe Phe Ile Leu
    2510                2515                2520

Gln Leu His Asp Glu Leu Leu Tyr Glu Val Ala Glu Asp Asp Val
    2525                2530                2535

Ile Gln Val Ala Gln Ile Val Lys His Glu Met Glu Asn Ala Met
    2540                2545                2550

Lys Leu Ser Val Lys Leu Asn Val Lys Val Arg Ile Gly Pro Ser
    2555                2560                2565

Trp Gly Asp Leu Gln Asp Leu Glu Leu
    2570                2575

<210> SEQ ID NO 15
<211> LENGTH: 2596
<212> TYPE: PRT
<213> ORGANISM: Pan troglodytes

<400> SEQUENCE: 15

Met Asn Leu Leu Arg Arg Ser Gly Lys Arg Arg Ser Glu Ser Gly
1               5                   10                  15

Ser Asp Ser Phe Ser Gly Ser Gly Asp Ser Ser Asp Ser Pro Gln
                20                  25                  30

Leu Leu Ser Gly Ser Val Leu Ser Pro Pro Gly Leu Gly Arg Cys
            35                  40                  45

Leu Lys Asp Arg Gly Arg Gln Ser Ala Ala Ala Gly Glu Cys Lys
        50                  55                  60

Pro Thr Val Pro Asp Tyr Glu Ile Asp Lys Leu Leu Leu Ala Asn Trp
65                  70                  75                  80

Gly Leu Pro Lys Ala Val Leu Glu Lys Tyr His Ser Phe Gly Val Lys
                85                  90                  95

Lys Met Phe Glu Trp Gln Ala Glu Cys Leu Leu Leu Gly Gln Val Leu
                100                 105                 110
```

```
Glu Gly Lys Asn Leu Val Tyr Ser Ala Pro Thr Ser Ala Gly Lys Thr
        115                 120                 125

Leu Val Ala Glu Leu Leu Ile Leu Lys Arg Val Leu Glu Met Arg Lys
130                 135                 140

Lys Ala Leu Phe Ile Leu Pro Phe Val Ser Val Ala Lys Glu Lys Lys
145                 150                 155                 160

Tyr Tyr Leu Gln Ser Leu Phe Gln Val Gly Ile Lys Val Asp Gly
                    165                 170                 175

Tyr Met Gly Ser Thr Ser Pro Ser Arg His Phe Ser Ser Leu Asp Ile
                180                 185                 190

Ala Val Cys Thr Ile Glu Arg Ala Asn Gly Leu Ile Asn Arg Leu Ile
            195                 200                 205

Glu Glu Asn Lys Met Asp Leu Leu Gly Met Val Val Asp Glu Leu
        210                 215                 220

His Met Leu Gly Asp Ser His Arg Gly Tyr Leu Leu Glu Leu Leu Leu
225                 230                 235                 240

Thr Lys Ile Cys Tyr Ile Thr Arg Lys Ser Ala Ser Cys Gln Ala Asp
                245                 250                 255

Leu Ala Ser Ser Leu Ser Asn Ala Val Gln Ile Val Gly Met Ser Ala
                260                 265                 270

Thr Leu Pro Asn Leu Glu Leu Val Ala Ser Trp Leu Asn Ala Glu Leu
                275                 280                 285

Tyr His Thr Asp Phe Arg Pro Val Pro Leu Leu Glu Ser Val Lys Val
        290                 295                 300

Gly Asn Ser Ile Tyr Asp Ser Ser Met Lys Leu Val Arg Glu Phe Glu
305                 310                 315                 320

Pro Met Leu Gln Val Lys Gly Asp Glu Asp His Val Val Ser Leu Cys
                325                 330                 335

Tyr Glu Thr Ile Arg Asp Asn His Ser Val Leu Leu Phe Cys Pro Ser
                340                 345                 350

Lys Lys Trp Cys Glu Lys Leu Ala Asp Ile Ile Ala Arg Glu Phe Tyr
            355                 360                 365

Asn Leu His His Gln Ala Glu Gly Leu Val Lys Pro Ser Glu Cys Pro
        370                 375                 380

Pro Val Ile Leu Glu Gln Lys Glu Leu Leu Glu Val Met Asp Gln Leu
385                 390                 395                 400

Arg Arg Leu Pro Ser Gly Leu Asp Ser Val Leu Gln Lys Thr Val Pro
                405                 410                 415

Trp Gly Val Ala Phe His His Ala Gly Leu Thr Phe Glu Glu Arg Asp
                420                 425                 430

Ile Ile Glu Gly Ala Phe Arg Gln Gly Leu Ile Arg Val Leu Ala Ala
            435                 440                 445

Thr Ser Thr Leu Ser Ser Gly Val Asn Leu Pro Ala Arg Arg Val Ile
450                 455                 460

Ile Arg Thr Pro Ile Phe Gly Gly Arg Pro Leu Asp Ile Leu Thr Tyr
465                 470                 475                 480

Lys Gln Met Val Gly Arg Ala Gly Arg Lys Gly Val Asp Thr Val Gly
                485                 490                 495

Glu Ser Ile Leu Ile Cys Lys Asn Ser Glu Lys Ser Lys Gly Ile Ala
                500                 505                 510

Leu Leu Gln Gly Ser Leu Lys Pro Val Arg Ser Cys Leu Gln Arg Arg
                515                 520                 525
```

```
Glu Gly Glu Glu Val Thr Ala Ser Met Ile Arg Ala Ile Leu Glu Ile
        530                 535                 540

Ile Val Gly Gly Val Ala Ser Thr Ser Gln Asp Met His Thr Tyr Ala
545                 550                 555                 560

Ala Cys Thr Phe Leu Ala Ala Ser Met Lys Glu Gly Lys Gln Gly Ile
                565                 570                 575

Gln Arg Asn Gln Glu Ser Val Gln Leu Gly Ala Ile Glu Ala Cys Val
            580                 585                 590

Met Trp Leu Leu Glu Asn Glu Phe Ile Gln Ser Thr Glu Ala Ser Asp
        595                 600                 605

Gly Thr Glu Gly Lys Val Tyr His Pro Thr His Leu Gly Ser Ala Thr
    610                 615                 620

Leu Ser Ser Ser Leu Ser Pro Ala Asp Thr Leu Asp Ile Phe Ala Asp
625                 630                 635                 640

Leu Gln Arg Ala Met Lys Gly Phe Val Leu Glu Asn Asp Leu His Ile
                645                 650                 655

Leu Tyr Leu Val Thr Pro Met Phe Glu Asp Trp Thr Thr Ile Asp Trp
            660                 665                 670

Tyr Arg Phe Phe Cys Leu Trp Glu Lys Leu Pro Thr Ser Met Lys Arg
        675                 680                 685

Val Ala Glu Leu Val Gly Val Glu Glu Gly Phe Leu Ala Arg Cys Val
    690                 695                 700

Lys Gly Lys Val Val Ala Arg Thr Glu Arg Gln His Arg Gln Met Ala
705                 710                 715                 720

Ile His Lys Arg Phe Phe Thr Ser Leu Val Leu Leu Asp Leu Ile Ser
                725                 730                 735

Glu Val Pro Leu Arg Glu Ile Asn Gln Lys Tyr Gly Cys Asn Arg Gly
            740                 745                 750

Gln Ile Gln Ser Leu Gln Gln Ser Ala Ala Val Tyr Ala Gly Met Ile
        755                 760                 765

Thr Val Phe Ser Asn Arg Leu Gly Trp His Asn Met Glu Leu Leu Leu
    770                 775                 780

Ser Gln Phe Gln Lys Arg Leu Thr Phe Gly Ile Gln Arg Glu Leu Cys
785                 790                 795                 800

Asp Leu Val Arg Val Ser Leu Leu Asn Ala Gln Arg Ala Arg Val Leu
                805                 810                 815

Tyr Ala Ser Gly Phe His Thr Val Ala Asp Leu Ala Arg Ala Asn Ile
            820                 825                 830

Val Glu Val Glu Val Ile Leu Lys Asn Ala Val Pro Phe Lys Ser Ala
        835                 840                 845

Arg Lys Ala Val Asp Glu Glu Glu Ala Val Glu Glu Arg Arg Asn
    850                 855                 860

Met Arg Thr Ile Trp Val Thr Gly Arg Lys Gly Leu Thr Glu Arg Glu
865                 870                 875                 880

Ala Ala Ala Leu Ile Val Glu Glu Ala Arg Met Ile Leu Gln Gln Asp
                885                 890                 895

Leu Val Glu Met Gly Val Gln Trp Asn Pro Cys Ala Leu Leu His Ser
            900                 905                 910

Ser Thr Cys Ser Leu Thr His Ser Glu Ser Glu Val Lys Glu His Thr
        915                 920                 925

Phe Ile Ser Gln Thr Lys Ser Ser Tyr Lys Lys Leu Thr Ser Lys Asn
    930                 935                 940

Lys Ser Asn Thr Ile Phe Ser Asp Ser Tyr Ile Lys His Ser Pro Asn
```

-continued

```
            945                 950                 955                 960
Ile Val Gln Asp Leu Asn Lys Ser Arg Glu His Thr Ser Ser Phe Asn
                    965                 970                 975
Cys Asn Phe Gln Asn Gly Asn Gln Glu His Gln Arg Cys Ser Ile Phe
                    980                 985                 990
Arg Ala Arg Lys Arg Ala Ser Leu Asp Ile Asn Lys Glu Lys Pro Gly
                    995                 1000                1005
Ala Ser Gln Asn Glu Gly Glu Thr Ser Asp Lys Lys Val Val Gln
        1010                1015                1020
Thr Phe Ser Arg Lys Thr Lys Lys Ala Pro Leu Asn Phe Asn Ser
        1025                1030                1035
Glu Lys Met Ser Arg Ser Phe Arg Ser Trp Lys His Arg Lys His
        1040                1045                1050
Leu Lys Arg Ser Arg Asp Ser Ser Pro Leu Lys Asp Ser Gly Ala
        1055                1060                1065
Cys Arg Ile His Leu Gln Gly Gln Thr Leu Ser Asn Pro Ser Leu
        1070                1075                1080
Cys Glu Asp Pro Phe Thr Leu Asp Glu Lys Lys Thr Glu Phe Arg
        1085                1090                1095
Asn Ser Gly Pro Phe Ala Lys Asn Val Ser Leu Ser Gly Lys Glu
        1100                1105                1110
Lys Asp Asn Lys Thr Ser Phe Pro Leu Gln Ile Lys Gln Asn Cys
        1115                1120                1125
Ser Trp Asn Ile Thr Leu Thr Asn Asp Asn Phe Val Glu His Ile
        1130                1135                1140
Val Thr Gly Ser Gln Ser Lys Asn Val Thr Cys Gln Ala Thr Ser
        1145                1150                1155
Val Val Ser Glu Lys Gly Arg Gly Val Ala Val Glu Ala Glu Lys
        1160                1165                1170
Ile Asn Glu Val Leu Ile Gln Asn Gly Ser Lys Asn Gln Asn Val
        1175                1180                1185
Tyr Ile Lys His His Asp Ile His Pro Ile Asn Gln Tyr Leu Arg
        1190                1195                1200
Lys Gln Ser His Glu Gln Thr Ser Thr Ile Thr Lys Gln Lys Asn
        1205                1210                1215
Ile Ile Glu Arg Gln Met Pro Cys Glu Ala Val Ser Ser Tyr Ile
        1220                1225                1230
Asn Arg Asp Ser Asn Val Thr Ile Asn Cys Glu Arg Ile Lys Leu
        1235                1240                1245
Asn Thr Glu Glu Asn Lys Pro Ser His Phe Gln Ala Leu Gly Asp
        1250                1255                1260
Asp Ile Ser Arg Thr Val Ile Pro Ser Glu Val Leu Pro Ser Ala
        1265                1270                1275
Gly Ala Phe Ser Lys Ser Glu Gly Gln His Glu Asn Phe Leu Asn
        1280                1285                1290
Ile Ser Arg Leu Gln Glu Lys Thr Gly Thr Tyr Thr Thr Asn Lys
        1295                1300                1305
Thr Lys Asn Asn His Val Ser Asp Leu Gly Leu Val Leu Cys Asp
        1310                1315                1320
Phe Glu Asp Ser Phe Tyr Leu Asp Thr Gln Ser Glu Lys Ile Ile
        1325                1330                1335
Gln Gln Met Ala Thr Glu Asn Ala Lys Leu Gly Ala Lys Asp Thr
        1340                1345                1350
```

```
Asn Leu Ala Ala Gly Ile Met Gln Lys Ser Leu Val Gln Gln Asn
    1355                1360                1365

Ser Met Asn Ser Phe Gln Lys Glu Cys His Ile Pro Phe Pro Ala
    1370                1375                1380

Glu Gln His Pro Leu Gly Ala Thr Lys Ile Asp His Leu Asp Leu
    1385                1390                1395

Lys Thr Val Gly Thr Met Lys Gln Ser Thr Asp Ser His Gly Val
    1400                1405                1410

Asp Ile Leu Thr Pro Glu Ser Pro Ile Phe His Ser Pro Ile Leu
    1415                1420                1425

Leu Glu Glu Asn Gly Leu Phe Leu Lys Lys Asn Glu Val Ser Val
    1430                1435                1440

Thr Asp Ser Gln Leu Asn Ser Phe Leu Gln Gly Tyr Gln Thr Gln
    1445                1450                1455

Glu Thr Val Lys Pro Val Ile Pro Leu Ile Pro Gln Lys Arg Thr
    1460                1465                1470

Pro Thr Gly Val Glu Gly Glu Cys Leu Pro Val Pro Glu Thr Ser
    1475                1480                1485

Leu Asn Met Ser Asp Ser Leu Leu Phe Asp Ser Phe Ser Asp Asp
    1490                1495                1500

Tyr Leu Val Lys Glu Gln Leu Pro Asp Met Gln Met Lys Glu Pro
    1505                1510                1515

Leu Pro Ser Glu Val Thr Ser Asn His Phe Ser Asp Ser Leu Cys
    1520                1525                1530

Leu Gln Glu Asp Leu Ile Arg Lys Ser Asn Val Asn Glu Asn Gln
    1535                1540                1545

Asp Thr His Gln Gln Leu Thr Cys Ser Asn Asp Glu Ser Ile Ile
    1550                1555                1560

Phe Ser Glu Met Asp Ser Val Gln Met Val Glu Ala Leu Asp Asn
    1565                1570                1575

Ala Asp Ile Phe Pro Val Gln Glu Lys Asn His Thr Val Val Ser
    1580                1585                1590

Pro Arg Ala Leu Glu Leu Ser Asp Pro Val Leu Asp Glu His His
    1595                1600                1605

Gln Gly Asp Gln Asp Gly Gly Asp Gln Asp Glu Arg Ala Glu Lys
    1610                1615                1620

Ser Lys Leu Thr Gly Thr Arg Gln Asn His Ser Phe Ile Trp Ser
    1625                1630                1635

Gly Ala Ser Phe Asp Leu Ser Pro Gly Leu Gln Arg Ile Leu Asp
    1640                1645                1650

Lys Val Ser Ser Pro Leu Glu Asn Glu Lys Leu Lys Ser Met Thr
    1655                1660                1665

Ile Asn Phe Ser Ser Leu Asn Arg Lys Asn Thr Glu Leu Asn Glu
    1670                1675                1680

Glu Gln Glu Val Ile Ser Asn Leu Glu Thr Lys Gln Val Gln Gly
    1685                1690                1695

Ile Ser Phe Ser Ser Asn Asn Glu Val Lys Ser Lys Ile Glu Met
    1700                1705                1710

Leu Glu Asn Asn Ala Asn His Asp Glu Thr Ser Ser Leu Leu Pro
    1715                1720                1725

Arg Lys Glu Ser Asn Ile Val Asp Asp Asn Gly Leu Ile Pro Pro
    1730                1735                1740
```

```
Thr Pro Ile Pro Thr Ser Ala Ser Lys Leu Thr Phe Pro Gly Ile
1745                1750                1755

Leu Glu Thr Pro Val Asn Pro Trp Lys Thr Asn Asn Val Leu Gln
1760                1765                1770

Pro Gly Glu Ser Tyr Leu Phe Gly Ser Pro Ser Asp Ile Lys Asn
1775                1780                1785

His Asp Leu Ser Pro Gly Ser Arg Asn Gly Phe Lys Asp Asn Ser
1790                1795                1800

Pro Ile Ser Asp Thr Ser Phe Ser Leu Gln Leu Ser Gln Asp Gly
1805                1810                1815

Leu Gln Leu Thr Pro Ala Ser Ser Ser Ser Glu Ser Leu Ala Ile
1820                1825                1830

Ile Asp Val Ala Ser Asp Gln Asn Leu Phe Gln Thr Phe Ile Lys
1835                1840                1845

Glu Trp Arg Cys Lys Lys Arg Phe Ser Ile Ser Leu Ala Cys Glu
1850                1855                1860

Lys Ile Arg Ser Leu Thr Ser Ser Lys Thr Ala Thr Ile Gly Ser
1865                1870                1875

Arg Phe Lys Gln Ala Ser Ser Pro Gln Glu Ile Pro Ile Arg Asp
1880                1885                1890

Asp Gly Phe Pro Ile Lys Gly Cys Asp Asp Ile Leu Val Val Gly
1895                1900                1905

Leu Ala Val Cys Trp Gly Gly Arg Asp Ala Tyr Tyr Phe Ser Leu
1910                1915                1920

Gln Lys Glu Gln Lys His Ser Glu Ile Ser Ala Ser Leu Val Pro
1925                1930                1935

Pro Ser Leu Asp Pro Ser Leu Thr Leu Lys Asp Arg Met Trp Tyr
1940                1945                1950

Leu Gln Ser Cys Leu Arg Lys Glu Ser Asp Lys Glu Cys Ser Val
1955                1960                1965

Val Ile Tyr Asp Phe Ile Gln Ser Tyr Lys Ile Leu Leu Leu Ser
1970                1975                1980

Cys Gly Ile Ser Leu Glu Gln Ser Tyr Glu Asp Pro Lys Val Ala
1985                1990                1995

Cys Trp Leu Leu Asp Pro Asp Ser Gln Glu Pro Thr Leu His Ser
2000                2005                2010

Ile Val Thr Ser Phe Leu Pro His Glu Leu Pro Leu Leu Glu Gly
2015                2020                2025

Met Glu Thr Ser Gln Gly Ile Gln Ser Leu Gly Leu Asn Ala Gly
2030                2035                2040

Ser Glu His Ser Gly Arg Tyr Arg Ala Ser Val Glu Ser Ile Leu
2045                2050                2055

Ile Phe Asn Ser Met Asn Gln Leu Asn Ser Leu Leu Gln Lys Glu
2060                2065                2070

Asn Leu Gln Asp Val Phe Arg Lys Val Glu Met Pro Ser Gln Tyr
2075                2080                2085

Cys Leu Ala Leu Leu Glu Leu Asn Gly Ile Gly Phe Ser Thr Ala
2090                2095                2100

Glu Cys Glu Ser Gln Lys His Ile Met Gln Ala Lys Leu Asp Ala
2105                2110                2115

Ile Glu Thr Gln Ala Tyr Gln Leu Ala Gly His Ser Phe Ser Phe
2120                2125                2130

Thr Ser Ser Asp Asp Ile Ala Glu Val Leu Phe Leu Glu Leu Lys
```

```
                2135                2140                2145

Leu Pro Pro Asn Arg Glu Met Lys Asn Gln Gly Ser Lys Lys Thr
    2150                2155                2160

Leu Gly Ser Thr Arg Arg Gly Ile Asp Asn Gly Arg Lys Leu Arg
    2165                2170                2175

Leu Gly Arg Gln Phe Ser Thr Ser Lys Asp Val Leu Asn Lys Leu
    2180                2185                2190

Lys Ala Leu His Pro Leu Pro Gly Leu Ile Leu Glu Trp Arg Arg
    2195                2200                2205

Ile Thr Asn Ala Ile Thr Lys Val Val Phe Pro Leu Gln Arg Glu
    2210                2215                2220

Lys Arg Leu Asn Pro Phe Leu Gly Met Glu Arg Ile Tyr Pro Val
    2225                2230                2235

Ser Gln Ser His Thr Ala Thr Gly Arg Ile Thr Phe Ile Glu Pro
    2240                2245                2250

Asn Ile Gln Asn Val Pro Arg Asp Phe Glu Ile Lys Met Pro Thr
    2255                2260                2265

Leu Val Gly Glu Ser Pro Pro Ser Gln Ala Val Gly Lys Gly Leu
    2270                2275                2280

Leu Pro Met Gly Arg Gly Lys Tyr Lys Lys Gly Phe Ser Val Asn
    2285                2290                2295

Pro Arg Cys Gln Ala Gln Met Glu Glu Arg Ala Ala Asp Arg Gly
    2300                2305                2310

Met Pro Phe Ser Ile Ser Met Arg His Ala Phe Val Pro Phe Pro
    2315                2320                2325

Gly Gly Ser Ile Leu Ala Ala Asp Tyr Ser Gln Leu Glu Leu Arg
    2330                2335                2340

Ile Leu Ala His Leu Ser His Asp Arg Arg Leu Ile Gln Val Leu
    2345                2350                2355

Asn Thr Gly Ala Asp Val Phe Arg Ser Ile Ala Ala Glu Trp Lys
    2360                2365                2370

Met Ile Glu Pro Glu Ser Val Gly Asp Asp Leu Arg Gln Gln Ala
    2375                2380                2385

Lys Gln Ile Cys Tyr Gly Ile Ile Tyr Gly Met Gly Ala Lys Ser
    2390                2395                2400

Leu Gly Glu Gln Met Gly Ile Lys Glu Asn Asp Ala Ala Cys Tyr
    2405                2410                2415

Ile Asp Ser Phe Lys Ser Arg Tyr Thr Gly Ile Asn Gln Phe Met
    2420                2425                2430

Thr Glu Thr Val Lys Asn Cys Lys Arg Asp Gly Phe Val Gln Thr
    2435                2440                2445

Ile Leu Gly Arg Arg Arg Tyr Leu Pro Gly Ile Lys Asp Asn Asn
    2450                2455                2460

Pro Tyr Arg Lys Ala His Ala Glu Arg Gln Ala Ile Asn Thr Ile
    2465                2470                2475

Val Gln Gly Ser Ala Ala Asp Ile Val Lys Ile Ala Thr Val Asn
    2480                2485                2490

Ile Gln Lys Gln Leu Glu Thr Phe His Ser Thr Phe Lys Ser His
    2495                2500                2505

Gly His Arg Glu Gly Met Leu Gln Ser Asp Arg Thr Gly Leu Ser
    2510                2515                2520

Arg Lys Arg Lys Leu Gln Gly Met Phe Cys Pro Ile Arg Gly Gly
    2525                2530                2535
```

Phe Phe Ile Leu Gln Leu His Asp Glu Leu Leu Tyr Glu Val Ala
    2540                2545                2550

Glu Glu Asp Val Val Gln Val Ala Gln Ile Val Lys Asn Glu Met
    2555                2560                2565

Glu Ser Ala Val Lys Leu Ser Val Lys Leu Lys Val Lys Val Lys
    2570                2575                2580

Ile Gly Ala Ser Trp Gly Glu Leu Lys Asp Phe Asp Val
    2585                2590                2595

<210> SEQ ID NO 16
<211> LENGTH: 2665
<212> TYPE: PRT
<213> ORGANISM: Fundulus heteroclitus

<400> SEQUENCE: 16

Met Arg Pro Trp Gln Gln Pro Arg Asp Pro Gly Val Cys His Val Gly
1               5                   10                  15

Glu Glu Asn Ala Arg Met Ala Ser Gly Pro Leu Lys Lys Lys Ser Tyr
            20                  25                  30

Leu Gly Gln His Gln Ile Lys Lys Thr Ser Ile Pro Ala Gly Asp
        35                  40                  45

His Glu Pro Thr Asp Gly Asp Gly Leu Leu Gln Lys Pro Ser Asp Lys
    50                  55                  60

Thr Asn Arg Ala Gln Ser Ser Gly Arg Asp Gly Leu Met Gly Gly Arg
65                  70                  75                  80

Gly Ala Leu Leu Pro Leu Gly Glu Ser Thr Leu Ala Leu Asp Glu Glu
                85                  90                  95

Met Leu Gln Thr Leu Asp Ala Ala Asp Leu Ser Lys Gly Asp Val Lys
            100                 105                 110

Arg Asp Gly Lys Gly Ala Phe Pro Pro Arg Pro Ala Pro Gln Thr
        115                 120                 125

Ala Arg Leu Lys Leu Asp Gly Lys Pro Lys Val Asp Gly Glu Ser
    130                 135                 140

Leu Pro Phe Thr Asn Gly Ala Glu Asp Pro Gln Gln Gly Gly Cys Lys
145                 150                 155                 160

Pro Arg Trp Asp Ser Asn Lys Pro Gly Trp Arg Ala Asp Cys Lys Asp
                165                 170                 175

Leu Ala Gln Lys Leu Leu Phe Ser Glu Asp Ser Gly Glu Ala Asp Arg
            180                 185                 190

Cys Thr Arg Asn Gln Glu Asn Asn Arg Ser Asp Ala Pro Ala Ser
        195                 200                 205

Ala Ser Ala Leu Pro Cys Lys Glu Thr Arg Ser Arg Gln Lys Ala Gly
    210                 215                 220

Gly Ser Arg Lys Gln Glu Leu Arg Gly Arg Gly Ser Pro Ser Asp
225                 230                 235                 240

Gly Lys Asp Lys Ser Met Lys Asn Thr Asp Pro Pro Leu Asp Val Ser
                245                 250                 255

Thr Asp Tyr Ile Leu Phe Ser Pro Thr Arg Leu Ala Glu Ala Arg Arg
            260                 265                 270

Arg Ala Lys Leu Gln Gln Ser Leu His Asn Gln Ser Val Ser Val Leu
        275                 280                 285

Thr Val Pro Ser Gly Leu Glu Leu Ser Thr Leu Ser Asp Thr Leu Pro
    290                 295                 300

Pro Pro Gly Val Ala Val Arg Ala Pro Glu Arg Gln Ala Glu Lys Leu

```
            305                 310                 315                 320
        Leu Leu Ser Ser Trp Gly Leu Pro Lys Pro Val Leu Glu Arg Tyr Gln
                        325                 330                 335

Asn His Gly Val Thr Arg Met Phe Glu Trp Gln Ala Gln Cys Leu Ala
                        340                 345                 350

Val Gly Gln Ala Leu Arg Gly Asn Leu Val Tyr Ser Ala Pro Thr
                        355                 360                 365

Ser Ala Gly Lys Thr Leu Val Ser Glu Leu Leu Ile Leu Lys Arg Val
                        370                 375                 380

Leu Glu Thr Arg Arg Lys Ala Leu Phe Ile Leu Pro Phe Val Ser Val
        385                 390                 395                 400

Ala Lys Glu Lys Met His Tyr Leu Gln Ser Val Phe Glu Glu Ala Gly
                        405                 410                 415

Ile Arg Val Glu Gly Tyr Met Gly Ser Thr Ser Ala Ala Gly Gly Phe
                        420                 425                 430

Thr Thr Leu Asp Val Ala Val Cys Thr Ile Glu Lys Ala Asn Ser Leu
                        435                 440                 445

Ile Asn Arg Leu Ile Glu Glu Asn Ser Met Asp Leu Leu Gly Val Val
                        450                 455                 460

Val Val Asp Glu Leu His Met Val Gly Asp Ser Arg Gly Gly Tyr Leu
        465                 470                 475                 480

Leu Glu Leu Leu Leu Thr Lys Ile Arg Tyr Ile Ala Gln Lys Gln Asn
                        485                 490                 495

Thr Ser Gly Ser Leu Ala Glu Gly Val Gln Ile Ile Gly Met Ser Ala
                        500                 505                 510

Thr Leu Pro Asn Leu Ser Leu Leu Ala Gly Trp Leu Gly Ala Asp Leu
                        515                 520                 525

Tyr Gln Thr Asp Tyr Arg Pro Val Pro Leu Gln Glu His Leu Lys Val
                        530                 535                 540

Gly Gly Asn Ile Tyr Asp Arg Ser Leu Ser Val Val Arg Gln Phe Thr
        545                 550                 555                 560

Pro Ala Leu Asn Val Lys Gly Asp Asp His Ile Val Ser Leu Cys
                        565                 570                 575

Tyr Glu Thr Val Arg Glu Gly His Ser Val Leu Leu Phe Cys Pro Ser
                        580                 585                 590

Lys Asn Trp Cys Glu Lys Leu Ala Asp Thr Ile Ala Arg Ala Phe Phe
                        595                 600                 605

Asn Leu Arg Asn Thr Asp Pro Gln Ser Glu Gly Val Pro Pro Pro Val
                        610                 615                 620

Cys Leu Asp Thr Ala Gly Leu Val Asp Val Ile Ala Gln Leu Arg Arg
        625                 630                 635                 640

Thr Pro Ala Gly Leu Asp Pro Ile Leu Gln Arg Thr Val Pro Trp Gly
                        645                 650                 655

Val Gly Phe His His Ala Gly Leu Thr Phe Asp Glu Arg Asp Val Leu
                        660                 665                 670

Glu Gly Ala Phe Arg Gln Gly Leu Val Arg Val Leu Ala Ala Thr Ser
                        675                 680                 685

Thr Leu Ser Ser Gly Val Asn Leu Pro Ala Arg Arg Val Val Ile Arg
                        690                 695                 700

Thr Pro Val Phe Asn Gly Arg Leu Leu Asp Pro Leu Thr Tyr Lys Gln
        705                 710                 715                 720

Met Ala Gly Arg Ala Gly Arg Lys Gly Val Asp Thr Thr Gly Glu Ser
                        725                 730                 735
```

```
Val Leu Val Cys Lys Gln Ser Glu His Gln Lys Gly Ile Ser Leu Leu
            740                 745                 750

Gln Gly Ala Leu Gln Pro Ile Ser Ser Cys Leu Val Arg Arg Glu Gly
            755                 760                 765

Glu Gly Val Thr Thr Ser Met Leu Arg Ala Ile Leu Glu Val Ile Val
            770                 775                 780

Gly Gly Val Ala Ser Ser Pro Arg Asp Val Arg Leu Tyr Ala Ser Cys
785                 790                 795                 800

Ser Leu Leu Ala Ala Ser Thr Lys Gly Asp Gly Lys Glu Ser Thr
                805                 810                 815

Glu Glu Thr Ser Ser Gly Ala Ile Glu Ala Cys Val Asp Trp Leu Met
            820                 825                 830

Gly Asn Glu Phe Ile Ser Ile Gln Arg Asp Gly Gln Asp Glu Gln Tyr
            835                 840                 845

Cys Pro Thr Gln Leu Gly Ala Ala Thr Leu Ser Ser Ser Leu Ser Pro
            850                 855                 860

Pro Glu Ala Leu Gly Ile Phe Ala Asp Leu Gln Arg Ala Met Lys Gly
865                 870                 875                 880

Phe Val Leu Glu Ser Asp Leu His Ile Leu Tyr Leu Ile Thr Pro Leu
            885                 890                 895

Tyr Ala Glu Trp Thr Thr Ile Asp Trp Tyr Gln Phe Phe Cys Leu Trp
            900                 905                 910

Glu Gln Leu Pro Ser Ser Met Lys Arg Val Ala Glu Leu Val Gly Val
            915                 920                 925

Gln Glu Gly Phe Leu Ala Arg Ser Val Ser Gly Lys Ile Val Ala Lys
            930                 935                 940

Thr Glu Lys Gln Leu Arg Gln Met Ala Val His Lys Arg Phe Phe Thr
945                 950                 955                 960

Thr Leu Val Leu Gln Asp Leu Val Ser Glu Val Pro Leu Gly Ala Val
            965                 970                 975

Ala Ser Lys Tyr Asn Cys Asn Arg Gly Gln Leu Gln Ser Leu Gln Gln
            980                 985                 990

Ser Ala Ser Thr Tyr Ala Gly Met Val Thr Val Phe Cys Lys Arg Leu
            995                 1000                1005

Gly Trp His Asn Met Glu Leu Leu Leu Ser Gln Tyr Gln Thr Arg
            1010                1015                1020

Leu Ser Phe Gly Val Gln Arg Glu Leu Val Asp Leu Val Arg Leu
            1025                1030                1035

Ser Leu Leu Asn Ala Thr Arg Ala Arg Ala Leu Tyr Ala Gln Gly
            1040                1045                1050

Leu Cys Thr Val Ala Gln Val Ala Arg Ala Pro Val Ala Asp Val
            1055                1060                1065

Glu Lys Ala Leu Arg Asn Ala Val Pro Phe Lys Ser Ser Lys Arg
            1070                1075                1080

Ala Val Asp Glu Ser Glu Met Glu Ala Ala Glu Arg Arg Asn Leu
            1085                1090                1095

Arg Cys Val Trp Val Thr Gly Gly Arg Ala Leu Thr Glu Gln Glu
            1100                1105                1110

Ala Ala Ala Glu Ile Val Ser Glu Ala Arg Leu Leu Leu Gln Glu
            1115                1120                1125

Asp Leu Ala Gln Leu Gly Val His Trp Asp Pro Ser Thr Leu Pro
            1130                1135                1140
```

```
Pro Gln Ala Pro Ser Gly Ser Ser Asp Asp Ser His Ser Gly
1145                1150                1155

Asp Ser Asp Ala Ala Ser Ala Pro Arg Val Ala Pro Arg Arg Ser
1160                1165                1170

Pro Met Arg Arg Thr Glu Gly His Pro Ser Gly Thr His Thr Gly
1175                1180                1185

Arg Arg Asn Val Ser Lys Ser Arg Gly Glu Glu Ile Gly Arg Asp
1190                1195                1200

Ala Glu Ile Gln Glu Lys Val Ala Tyr Gly Lys Gly Ala Leu Glu
1205                1210                1215

Gly Glu Ala Arg Lys Pro Asp Val Thr Asp Pro Glu Ile Ser Asp
1220                1225                1230

Val Leu Val Glu Arg Ala Glu Gly Arg Asn Glu Ala Lys Pro Ser
1235                1240                1245

Thr Ser Arg Gln Asp Glu Ala Glu His Val Glu Asp Lys Gln Glu
1250                1255                1260

Thr Ala Gly Ala Val Gln His Gly Gly Arg Leu Glu Ser Ile Ser
1265                1270                1275

Leu Val Glu Glu Asp Arg Arg Lys Arg Asn Lys Ser Val Glu Glu
1280                1285                1290

Gln Thr His His Tyr Leu Asn Gln Pro Ala Val Glu Met Ser Leu
1295                1300                1305

Thr Gln Glu Leu Ala Glu Ile Val Ser Ser Pro Leu Pro Pro Pro
1310                1315                1320

Pro Pro Gln Pro Gln Pro Pro Pro Ser Pro Ala Pro Pro Pro Arg
1325                1330                1335

Phe Arg Ala Pro Val Ser Arg Leu Ala His Arg Pro Ser Ala Pro
1340                1345                1350

Thr Ser Thr Gly Lys Gly Gly Cys Ser Thr Ser Pro Leu Leu Pro
1355                1360                1365

Arg Thr Pro Lys His Ser Ala Ala Leu Arg Lys Val Leu Gln Ser
1370                1375                1380

Ile Gln Thr Gly Arg Gly Val Gln Asp Arg Leu Gln Pro Ala Asp
1385                1390                1395

Leu Ser Pro Ser Lys Val Pro Asn Ala Ala Pro Val Thr Leu Gln
1400                1405                1410

Glu Asn Pro Asp Val Ala Ser Thr Pro Pro Gly Ala Asp Ser Ala
1415                1420                1425

Pro Leu Phe Thr Pro Glu Ala Lys Arg Arg Arg Thr Glu Ala Gly
1430                1435                1440

Gly Val Asp Arg Phe Ser Ser Pro Glu Leu Tyr Ala Gly Ser Lys
1445                1450                1455

Thr Asp Glu Glu Glu Gln Gly Asp Ala Glu Glu Glu Glu Glu Glu
1460                1465                1470

Glu Ser Phe Gly Arg Ser Leu Asp Leu Asp Thr Gln Thr Glu Arg
1475                1480                1485

Met Ile Ala Gln Arg Pro Leu Thr Gly Thr Ala Gly Gly Arg Asp
1490                1495                1500

Glu Ala Gly Glu Gln Gln Gly Glu Arg Arg Gly Asp Arg Val Lys
1505                1510                1515

Gly Pro Asp Asp Asp Arg Arg Asp Glu Ala Glu Gly Pro Glu Thr
1520                1525                1530

Ala Ala Ala Arg Phe Gln Ile Ser Val Thr Glu Ser Gln Met Glu
```

```
                   1535                1540                1545

Leu Ile Leu Asn Ser Asn Pro Arg Ala Ser Pro Ser Pro Ala Arg
                   1550                1555                1560

Gly Asp Thr Asp Gln Ala Gly Asp Asp Arg Gln Leu Ser Asp Asn
                   1565                1570                1575

Asn Glu Ala Ala Ala Glu Ser Pro Asp Gly Ser Ser Gly Phe Leu
                   1580                1585                1590

Phe Asp Ser Met His Asp Ser Ala Leu Leu Asp Thr Leu Leu Leu
                   1595                1600                1605

Asn Pro Ser Pro Glu Pro Ala Gly Glu Glu Glu Pro Ala Gly
                   1610                1615                1620

Pro Ala Pro Ala Pro Ser Ala Gln Gln Lys Arg Arg Ser Glu Leu
                   1625                1630                1635

Leu Ala Asn Gln Glu Ala Glu Glu Gln Glu Ala Val Arg Trp Gly
                   1640                1645                1650

Glu Ser Phe Phe Cys Leu Ser Glu Trp Gly Glu Ser Phe Leu Val
                   1655                1660                1665

Gly Glu Ala Phe Leu Gly Arg Gln Ala Leu Ser Arg His Ala Glu
                   1670                1675                1680

Gly Gly Glu Gly Asn Gln Gly Leu Gln Gln Pro Ser Lys Glu Glu
                   1685                1690                1695

Glu Ser Glu Glu Glu Lys Ala Gly Gly Arg Gln Arg Asp Glu Glu
                   1700                1705                1710

Lys Asp Ala Lys His Val Glu Lys Leu Thr Gly Glu Glu Arg Glu
                   1715                1720                1725

Asn Leu Ile Glu Asn Asp Val Leu Lys Thr Pro Gly Val Gln Asn
                   1730                1735                1740

Ser Pro Glu Ser Ala Phe Tyr Cys Ser Pro Gly Leu Gln Glu Ile
                   1745                1750                1755

Phe Asp Arg Trp Pro Ser Met Ser Asp Gln Pro Gly Pro Thr Ala
                   1760                1765                1770

Asp Thr Ala Asp Ala Thr Glu Leu Pro Arg Pro Ala Thr Gln Pro
                   1775                1780                1785

Gly Arg Lys Arg Lys Gln Pro Gln Arg Pro Asp Ala Thr Gln Lys
                   1790                1795                1800

Ala Gln Pro Pro Glu Arg Pro Gly Ser Ala Gly Asp Leu Ile Pro
                   1805                1810                1815

Pro Thr Gln Glu Thr Ala Pro Val Thr Pro Arg Val Lys Leu Thr
                   1820                1825                1830

Thr Ser Ser Val Leu Ser Pro Ala Val Thr Gln Pro Leu Lys Gln
                   1835                1840                1845

Ser Thr Pro Ser His Arg Leu Gln Glu Gly Pro Thr Asp Gly Glu
                   1850                1855                1860

Arg Ala Thr Ala His Ala Ala Val Ser Val Ser Asp Arg Arg Pro
                   1865                1870                1875

Gln Arg Ser Pro Pro Thr Gly Arg Ser Leu Phe Phe Pro Pro Gln
                   1880                1885                1890

Thr Ala Ala Ser Pro Pro Ser Pro Arg Pro Glu Pro Pro Ser Asp
                   1895                1900                1905

Ala Glu Ser Pro Val Ser Pro Gly Gly Phe Ala Leu Gln Leu Ser
                   1910                1915                1920

Gln Asp Ala Ser Leu Leu Cys Ser Asp Ser Gly Ser Phe Ser Ile
                   1925                1930                1935
```

```
Ile Asp Val Ala Ser Asp Arg Arg Leu Phe Asp Thr Phe Ile Lys
    1940            1945                1950

Glu Trp Glu Thr Lys Glu Arg Phe Ser Val Ala Leu Ala Cys Glu
    1955            1960                1965

Arg Arg Ala His Arg Arg Pro Glu Asp Asp Thr Gly Gly Arg
    1970            1975                1980

Arg Lys Arg Ala Ser Ala Ala His Pro Thr Pro Asp Gly Phe Pro
    1985            1990                1995

Val Gly Asp Asp Glu Gly Arg Thr Leu Ile Gly Leu Ser Val Cys
    2000            2005                2010

Trp Gly Ala Arg Asp Ala Tyr Tyr Val Ser Leu Gln Gln Glu Gln
    2015            2020                2025

Ser Glu Gly Leu Ser Ser Ser Leu Ala Pro Pro Leu Asp Lys
    2030            2035                2040

Ala Leu Pro Val Thr Gln Arg Leu Gln Arg Val Lys Ala Cys Leu
    2045            2050                2055

Ser Ala Ala Pro Ser Gly Arg Arg Gly Arg Ala Val Val Val Tyr
    2060            2065                2070

Asp Ile Ile Lys Val Tyr Lys Arg Leu Val Arg Ser Cys Gly Ile
    2075            2080                2085

Ser Leu Glu Gly Asn Tyr Glu Asp Pro Lys Val Ala Cys Trp Leu
    2090            2095                2100

Leu Asp Pro Gly Arg Glu Glu Arg Thr Leu Pro Asn Met Val Thr
    2105            2110                2115

Val Tyr Cys Pro Glu Glu Leu Pro Leu Val Asp Gly Leu Gly Asn
    2120            2125                2130

Ala His Ser His Cys Pro Arg Val Arg Ala Ala Thr Glu Ser Val
    2135            2140                2145

Leu Val His Ala Val Met Gln His Leu Ser Gly Leu Leu Glu Arg
    2150            2155                2160

Asp Gly Ala Leu Asp Val Phe Arg Arg Thr Glu Met Pro Ser Gln
    2165            2170                2175

Val Cys Leu Ala Leu Leu Glu Leu Asn Gly Val Gly Phe Ser Ala
    2180            2185                2190

Glu Glu Cys Glu Arg Gln Lys His Val Met Gln Ala Lys Leu Ser
    2195            2200                2205

Ala Leu Glu Ala Glu Ala Tyr Ser Leu Ala Gly His Ser Phe Ser
    2210            2215                2220

Leu Thr Ser Val Asp Asp Val Ala Gln Val Leu Phe Leu Glu Leu
    2225            2230                2235

His Leu Pro Pro Asn Gly Asp Val Asp Gly Pro Arg Ser Lys Lys
    2240            2245                2250

Thr Leu Gly Tyr Thr Arg Arg Gly Gly Gly Arg Ala Arg Leu Gly
    2255            2260                2265

Lys Gln Phe Ser Thr Thr Lys Asp Val Leu Glu Lys Leu Arg Pro
    2270            2275                2280

Leu His Pro Leu Pro Gly Val Ile Leu Glu Trp Arg Arg Ile Thr
    2285            2290                2295

Asn Ala Leu Thr Lys Val Val Phe Pro Leu Gln Arg Glu Lys Arg
    2300            2305                2310

Tyr Glu Pro Thr Leu Asp Met Asp Arg Ile Tyr Pro Val Ala Gln
    2315            2320                2325
```

```
Thr His Thr Ala Thr Gly Arg Val Ser Phe Thr Glu Pro Asn Ile
    2330            2335                2340

Gln Asn Val Pro Lys Asp Phe Glu Ile Ser Leu Pro Thr Val Val
    2345            2350                2355

Gly Glu Ser Pro Pro Ser Gln Gly Gly Phe Gln Met Pro Asn Arg
    2360            2365                2370

Pro Gly Arg Arg Arg Ser Val Ala Pro Leu Pro Ala Ala Ala Asp
    2375            2380                2385

Gln Gly Pro Ala Phe Ser Val Ser Met Arg His Ala Phe Val Pro
    2390            2395                2400

Phe Ser Gly Gly Met Ile Leu Ala Ala Asp Tyr Ser Gln Leu Glu
    2405            2410                2415

Leu Arg Val Leu Ala His Leu Ser Lys Asp Gln Arg Leu Leu Gln
    2420            2425                2430

Val Leu Asn Gly Gly Ala Asp Val Phe Arg Cys Ile Ala Ala Glu
    2435            2440                2445

Trp Lys Ser Val Glu Pro Ala Ser Val Gln Asp Asp Leu Arg Gln
    2450            2455                2460

Gln Ala Lys Gln Ile Cys Tyr Gly Ile Ile Tyr Gly Met Gly Ala
    2465            2470                2475

Lys Ser Leu Gly Glu Gln Met Gly Val Glu Glu Asn Asp Ala Ala
    2480            2485                2490

Cys Tyr Ile Glu Ser Phe Lys Ala Arg Tyr Lys Gly Ile Asn Ala
    2495            2500                2505

Phe Leu Lys Gln Thr Val Lys Lys Cys Leu Lys Asp Gly Tyr Val
    2510            2515                2520

Gln Thr Leu Met Gly Arg Arg Tyr Leu Ala Gly Ile Ala Asn
    2525            2530                2535

Ala Asn Pro His Val Lys Ala His Ala Glu Arg Gln Ala Val Asn
    2540            2545                2550

Thr Thr Val Gln Gly Ser Ala Ala Asp Ile Val Lys Leu Ala Thr
    2555            2560                2565

Val Asn Ile Gln Lys Arg Leu Arg Glu Thr Tyr Pro Ser Ala Pro
    2570            2575                2580

Leu Ser His Gln His Ala His Ser Ala His Asn Asn Gln Arg Arg
    2585            2590                2595

Phe Gly Thr Ser Arg Leu Arg Gly Ala Tyr Phe Ile Leu Gln Leu
    2600            2605                2610

His Asp Glu Leu Ile Tyr Glu Thr Thr Glu Arg Asp Leu Ile Gln
    2615            2620                2625

Val Ala Gln Ile Val Lys Arg Glu Met Glu Ser Ala Val Lys Leu
    2630            2635                2640

Tyr Val Lys Leu Lys Ala Lys Val Lys Val Gly Pro Ser Trp Gly
    2645            2650                2655

Asn Leu Gln Asp Leu Asp Ile
    2660            2665

<210> SEQ ID NO 17
<211> LENGTH: 2674
<212> TYPE: PRT
<213> ORGANISM: Crassostrea gigas

<400> SEQUENCE: 17

Met Thr Ser Lys Ser Lys Asn Gly Gly Met Glu Leu Asp Ala Ser Phe
1               5                   10                  15
```

```
Ser Ser Ser Phe Cys Thr Glu Leu Asp Ala Gln Met Leu Val Ala Met
            20                  25                  30

Glu Thr Met Glu Lys Gln Pro Arg Ser Gln Lys Ser Leu Pro Lys Gly
        35                  40                  45

Thr Lys Lys Asn Ser Pro Val Leu Thr Ser Thr Pro Gln Ser Val Thr
 50                  55                  60

Pro Leu Pro Arg Arg Gln Ala Gln Leu Met Lys Ser Leu Phe Thr Leu
 65                  70                  75                  80

Gln Ser Pro Leu Asn Asp Ser Leu Phe Ser Pro Phe Ser Ser Gln Thr
                 85                  90                  95

Thr Asp Asn Val Lys Asp Gly Glu Gln Leu Thr Pro Ser Ser Ala Met
            100                 105                 110

Asn Gly Lys Pro Cys Arg Lys Arg Thr Arg Lys Val Leu Asn Glu Ile
            115                 120                 125

Ile Asn Glu Lys Glu Arg Ile Asp Glu Asp Asn Gly Asp Lys Leu Leu
130                 135                 140

Leu Lys Asn Trp Gly Leu Pro Glu Pro Val Met Lys Gln Tyr Ser Asp
145                 150                 155                 160

Lys Gly Ile Thr Ser Met Phe Glu Trp Gln Ala Glu Cys Leu Cys Leu
                165                 170                 175

Pro Gly Val Leu Asp Gly Gly Asn Leu Val Tyr Ser Ala Pro Thr Ser
            180                 185                 190

Ala Gly Lys Thr Met Val Ala Glu Leu Leu Val Leu Lys Arg Val Leu
            195                 200                 205

Glu Thr Lys Lys Lys Ala Ile Ile Ile Leu Pro Phe Val Ser Val Ala
210                 215                 220

Arg Glu Lys Met Phe Tyr Leu Gln Gln Leu Tyr Gln Glu Val Gly Val
225                 230                 235                 240

Ser Val Ser Gly Phe Met Gly Ser Tyr Ser Pro Pro Gly Gly Leu Ser
                245                 250                 255

Gln Val Asp Val Ala Val Cys Thr Ile Glu Lys Gly Asn Gly Leu Ile
            260                 265                 270

Asn Arg Leu Met Glu Glu Asn Arg Leu Asp Gln Leu Gly Ile Val Val
            275                 280                 285

Ile Asp Glu Leu His Leu Val Gly Asp Gln His Arg Gly Tyr Leu Leu
290                 295                 300

Glu Leu Met Leu Thr Lys Ile Arg Phe Leu Ser Gln Arg Met Lys Lys
305                 310                 315                 320

Pro Asp Pro Gln Asn Met Glu Ser Ser Thr Glu Gly Ile Gln Ile
                325                 330                 335

Ile Gly Met Ser Ala Thr Leu Pro Asn Leu Asp Leu Leu Ala Arg Trp
                340                 345                 350

Leu Asp Ala Thr Leu Tyr Arg Thr Asp Tyr Arg Pro Val Pro Leu Thr
            355                 360                 365

Glu Cys Val Lys Leu Gly Ala Asp Ile Phe Asp Ser Arg Leu Gln Lys
            370                 375                 380

Ile Arg Glu Val Asp Leu Ser Val Thr Phe Lys Gly Asp Thr Asp His
385                 390                 395                 400

Val Val Pro Leu Cys Leu Glu Thr Leu Arg Asp Gly His Ser Val Leu
                405                 410                 415

Ile Phe Cys Pro Thr Lys Asn Trp Cys Glu Lys Leu Ala Glu Thr Ile
            420                 425                 430
```

```
Ala Arg Glu Phe Tyr Gly Ile Leu Lys Lys Ala Pro Val Asp Met Gln
            435                 440                 445

Ala Asn Gln Gly Ser Gly Gly Asn Pro Pro Ser Pro Cys Leu Pro Leu
        450                 455                 460

Ser Arg Ala Ser Leu Gln Glu Val Val Glu Gln Leu Arg Arg Thr Pro
465                 470                 475                 480

Val Gly Leu Asp Ser Thr Leu Gly Lys Thr Val Pro Tyr Gly Val Ala
                485                 490                 495

Tyr His His Ala Gly Lys Tyr Gln His Lys Phe Ile Val Arg Val Lys
            500                 505                 510

Glu Asp Pro Gly Gly Ala Arg Leu Tyr Pro Glu Glu Asp Cys Pro Tyr
        515                 520                 525

Val Val Ala His His His Thr Gly Leu Thr Phe Asp Glu Arg Asp Ile
        530                 535                 540

Leu Glu Gly Ala Phe Arg Gln Gly Ala Val Lys Val Leu Ile Ala Thr
545                 550                 555                 560

Ser Thr Leu Ser Ser Gly Val Asn Leu Pro Ala Arg Arg Val Ile Ile
                565                 570                 575

Arg Thr Pro Leu Phe His Gly Lys Thr Ile Asp Phe Leu Thr Tyr Lys
            580                 585                 590

Gln Met Ile Gly Arg Ala Gly Arg Lys Gly Val Asp Thr Gln Gly Glu
            595                 600                 605

Ser Ile Leu Ile Cys Lys Pro Gly Glu Arg Ser Lys Ala Val Thr Leu
            610                 615                 620

Val Gln Ser Ala Leu Pro Pro Val Ser Ser Cys Leu Ile Lys Asn Gln
625                 630                 635                 640

Gly Glu Gln Leu Ser Ser Ser Met Lys Arg Ala Ile Leu Glu Ile Val
                645                 650                 655

Val Ser Gly Val Ala Asp Ser Val Thr Asp Val Thr Ala Tyr Ala Ser
                660                 665                 670

Cys Thr Met Leu Ala Ala Ser Leu Asp Thr Ser Ser Asp Gln Thr Gln
            675                 680                 685

Gly Met Ile Ser Ala Cys Ile Gln Phe Leu Gln Glu Asn Glu Phe Val
            690                 695                 700

Ser Leu Gln Arg Val Gln Ser Ser Asp Gly Val Tyr Glu Asp Arg Phe
705                 710                 715                 720

Val Pro Thr Gln Leu Gly Ala Ala Val Leu Ala Ser Ser Leu Ser Pro
                725                 730                 735

Asp Glu Gly Leu Ser Val Phe Ala Glu Leu Gln Lys Ala Arg Gln Cys
            740                 745                 750

Phe Val Leu Glu Asn Glu Leu His Ile Val Tyr Leu Val Thr Pro Ile
            755                 760                 765

Tyr Ser Leu Asp Leu Gly Ala Gly Met Asn Trp Tyr Lys Phe Tyr Cys
770                 775                 780

Leu Trp Asp Lys Leu Ser Pro Asp Lys Lys Arg Val Ala Gln Leu Val
785                 790                 795                 800

Gly Val Ser Glu Ala Phe Leu Thr Arg Ala Ile Gln Gly Arg Ile Pro
                805                 810                 815

Thr Lys Thr Glu Asn Gln Ile Arg Ser Leu Ala Ile His Lys Arg Phe
            820                 825                 830

Tyr Thr Ser Leu Ile Leu Ser Asp Leu Val Gln Glu Val Pro Leu Gly
            835                 840                 845

Glu Val Cys His Arg Tyr Gly Ala Asn Lys Gly Gln Leu Gln Ser Leu
```

-continued

```
            850                 855                 860
Gln Gln Thr Ala Ala Thr Phe Ala Gly Met Val Thr Val Phe Cys Ala
865                 870                 875                 880
Arg Leu Gly Trp Tyr Asn Leu Glu Leu Ile Leu Gly Gln Phe Gln His
                885                 890                 895
Arg Leu Thr Phe Gly Ile Gln Arg Glu Leu Cys Asp Leu Val Arg Leu
                    900                 905                 910
Thr Leu Leu Asn Gly Gln Arg Ala Arg Val Leu Tyr Asp Gly Gly Phe
            915                 920                 925
His Thr Val Ala Ala Leu Ala Asn Ala Ser Val Ser Asp Val Glu Lys
        930                 935                 940
Ile Phe Lys Lys Ser Ser Pro Phe Gln Ser Ser Lys Lys Leu Glu Asn
945                 950                 955                 960
Glu Thr Glu Trp Glu Ala Ala Arg Arg Gln Ser Arg Cys Ile Trp
                965                 970                 975
Leu Thr Gly Arg Lys Gly Ala Thr Glu Arg Glu Ala Ala Gln Ala Ile
                980                 985                 990
Ile Gln Glu Ala Lys Ser Leu Ile Gln Gln Glu Leu Gly Gly Leu Gly
            995                 1000                1005
Ile Gln Trp Lys Thr Pro Asp Thr Arg Lys Ser Leu Glu Glu Gly
        1010                1015                1020
Ser Asn Pro Asp Gln Asn Gly Met Asp Cys Ser Arg Asp Leu Glu
    1025                1030                1035
Lys Ser Ser Asn Asn His Gln Ile Gly Leu Met Lys Met Lys Ser
    1040                1045                1050
Lys Gly Ser Val Arg Lys Arg Ser Leu Ser Arg Lys Ser Pro
    1055                1060                1065
Ala Leu Ser Gln Ala Arg Ser Ser Arg Gly Lys Gly Phe Asn Arg
    1070                1075                1080
Gln Glu Lys Ser Val Val Ile Ser Pro Pro Ser Phe Asn Ser Gln
    1085                1090                1095
Ser Arg Arg Asn Lys Ser Asn Ile Gly Thr Asp Ser Gly Ser Gly
    1100                1105                1110
Lys Pro Cys Asp Asn Asp Cys Ile Val Ile Val Asp Asp Ser Ser
    1115                1120                1125
Gly Asp Pro Asn Glu Arg Gln Gly Asn Lys Glu Ile Pro Ser Ile
    1130                1135                1140
Lys Asp Phe Val Val Arg Gln Ile Glu Glu Gln Ser Cys Gln Gln
    1145                1150                1155
Arg Asn Arg Asn Asn Pro Glu Lys Arg Asp Cys Glu Lys Asn Cys
    1160                1165                1170
Thr Ser Glu Val Arg Val Gln Pro Asn His Met Tyr His Lys Asp
    1175                1180                1185
Gln Leu Gln Ile Asp Leu Val Lys Thr Asn Ala Asn Cys Asn Glu
    1190                1195                1200
Glu Ala Gly Lys Gln Leu Thr Gly Leu His Glu Ala Arg Glu Lys
    1205                1210                1215
Pro Arg Val Glu Ala Ile Lys Ala Asn Pro Ser Arg Cys Thr Glu
    1220                1225                1230
Arg Glu Asn Val Ser Ala Ser Ser Ser Ser Ser Ser Ser Ser
    1235                1240                1245
Thr Ser Ser Ser Val Ile Asn Ser Ser Ser Arg Pro Ala Glu Asp
    1250                1255                1260
```

```
Ser His Val Phe Lys Ser Pro Ile Phe Ser Ser Val Ser Thr Gly
1265                1270                1275

Ile Lys Lys Ser Gly Pro Lys Thr Arg Ser Ser Ser Phe Pro Leu
1280                1285                1290

Ser Thr Leu Ser Thr Ser Ser Thr Ser Leu Gly Ser Ser Thr Ala
1295                1300                1305

Ser Val Val Met Ser Pro Gln Leu Ala Lys Asn Lys Asn Asp Leu
1310                1315                1320

Ile Lys Ile Pro Ser Asn Lys Arg Asn Ala Met Pro Asn Gln Ser
1325                1330                1335

Ile Gln Arg Gly Ile Leu Ser Gly Val Gln Gln Ile Ile Thr Asn
1340                1345                1350

Ser Thr Asp Leu Glu Thr Val Asn Gly Lys Leu Asn Glu His Glu
1355                1360                1365

Ser Asp Val Arg Thr Ile Asn Glu Arg Arg Gln Lys Ala Asp Leu
1370                1375                1380

Thr Pro Glu Ala Asn Phe Arg Glu Leu Arg Asp Arg Gly Asp Ser
1385                1390                1395

Glu Glu Arg Lys Lys Leu Gln Glu Ile Lys Val Asn Lys Thr Ile
1400                1405                1410

Glu Pro Met Ile Cys Ser Glu Asp Phe Ala Asp Ser Phe Val Phe
1415                1420                1425

Glu Ser Gln Met Asp Gly Asn Met Glu Ala Phe Pro Gly Leu Cys
1430                1435                1440

Asn Glu Val Ser Gln Ser Leu Gln Ser Lys Lys Thr Leu Gly Asp
1445                1450                1455

Ser Glu Lys Ile Asn Ser Lys Ile Val Val Asp Lys Ile Ile Glu
1460                1465                1470

Lys Gln Ile Asn Ser Asn Gly Phe Phe Gln Pro Asn Gly Ser Ser
1475                1480                1485

Ser Ser Lys Lys His Leu Val Arg Asn Ala His Ile Val Val Glu
1490                1495                1500

Lys His Arg Thr Asn Thr Ala Leu Ser Thr Ala Asp Ala Ala Thr
1505                1510                1515

Val Asn Lys Glu Gln Val Asp Asp Glu His Ser Thr Asp Gly Asn
1520                1525                1530

Asp Met Asn Leu Ser Cys Ser Leu Leu Ser Ser His Asp Val Ser
1535                1540                1545

Cys Asp Leu Leu Pro Ala Ser Asn Phe Glu Lys Cys Met Val Ser
1550                1555                1560

Asp Asp Glu Ser Asp Val Cys Arg Asp Glu Ser Tyr Arg Asp Leu
1565                1570                1575

Arg Ile Pro Tyr Leu Ser Gly Gln Glu Ala Ala Cys Phe Asp Gly
1580                1585                1590

Asn Glu Arg Lys Ala Asp Leu Ala Leu Gly Gly Tyr Gln Ile Ser
1595                1600                1605

Gln Gly Leu Leu Gln Glu Leu Asp Glu Thr Phe Ser Glu Glu Cys
1610                1615                1620

Ser Gln Gly Ser Lys Gly Gln Ser Gln Arg Ser Ala Gly Gln Gly
1625                1630                1635

Gly Ser Phe Lys Asn Gly Lys Lys Gln Asn Asn Asn Ser Ile Asp
1640                1645                1650
```

```
Gly Met Glu Ala Ser Lys Val Glu Gln Gly Lys Ala Thr Glu Gln
    1655             1660                 1665

Asn Leu Lys Thr Phe Glu Lys Lys Asn Gly Gln Ile Ile Glu
    1670             1675                 1680

Arg Lys Met Glu Glu Ala Glu Val Gly Val Thr Glu Glu Met Asp
    1685             1690                 1695

Asp Ser Leu Thr Leu Ser Met Val Tyr Glu Val Ile Glu Asn Cys
    1700             1705                 1710

Asp Lys Gly Gln Cys Asn Lys Asn Leu Asn Ser Lys Thr Asp Lys
    1715             1720                 1725

Ser Asn Thr Asn Gln Leu Thr Ser Arg Arg Ser Gln Arg Asn
    1730             1735                 1740

Ala Lys Ser Asn Ser Lys Lys Thr Asn Glu Ile Ile Cys Glu Glu
    1745             1750                 1755

Leu Ile Ser Lys Lys Ser Ser Glu Cys Asn Lys Arg Ser Thr Leu
    1760             1765                 1770

Lys Ser Lys Glu Ser Ser Phe Thr Lys Val Lys Cys Ser Arg Ser
    1775             1780                 1785

Ser Gln Asp Lys Asp Lys Arg Leu Ser Pro Gly Thr Leu Ala Phe
    1790             1795                 1800

Leu Asp Asp Leu His Thr Ser Leu Asp Thr Asp Ser Asp Thr Ile
    1805             1810                 1815

Val Met Lys Thr Pro Leu Cys Gln Arg Arg Arg Gly Asn Asn Asn
    1820             1825                 1830

Lys Glu Gly Ser Thr Arg Asp Ser Val Val Met Asp Glu Val Met
    1835             1840                 1845

Asp Glu Asp Leu Gln Asn Glu Tyr Ser Gly Asp Asn Val Arg
    1850             1855                 1860

Thr Asn Glu Cys Leu Ser Pro Thr Pro Pro Arg Leu Ser Leu Val
    1865             1870                 1875

Asn Ser Pro Lys Thr Ile Arg Lys Ala Thr Pro Asn Arg His Arg
    1880             1885                 1890

Pro Gln Lys Gln Asp Asp Arg Arg Ser Ala Arg Lys Asn Ile Glu
    1895             1900                 1905

Ser Leu Gly Val Ser Met Lys Asn Ser Lys Val Pro Phe Val Glu
    1910             1915                 1920

Ser Ala Lys Ser Ala Glu Glu Val Arg Glu Trp Asn Ser Gly
    1925             1930                 1935

Lys Leu Glu Ser Pro Thr Gly Glu Asp Pro Pro Tyr Val Glu Arg
    1940             1945                 1950

Gly Pro Val Val Asp Pro Asn Glu Thr Gly Ile Pro Pro Ser Gln
    1955             1960                 1965

Gly Ala Phe Thr Ile Ile Asp Val Cys Ala Asp Lys Val Leu Phe
    1970             1975                 1980

Asp Thr Phe Ile Lys Glu Trp Asn Cys Gln Pro Ser Phe Ala Ile
    1985             1990                 1995

Ser Leu Ala Cys Ile Asn Lys Pro Arg Asp Pro Val Thr Thr Thr
    2000             2005                 2010

Gly Gly Ile Gly Ala Lys Phe Thr Glu Ala Gly Asp Thr Gly His
    2015             2020                 2025

Lys Ser Ser Lys Val Lys Thr Thr Glu Pro Gly Val Ala Ser Arg
    2030             2035                 2040

Gly Ile Pro Val Trp Gly Val Asn Leu Val Ile Thr Gly Val Ala
```

```
              2045                2050                2055

Val Ser Trp Gly Asp Arg Asp Ala Tyr Phe Ile Thr Leu Thr Ser
              2060                2065                2070

Glu Asn Ile Glu Asp Glu Glu Asp Thr Asp Leu Ser Pro Pro Asp
              2075                2080                2085

Leu Asp Lys Ser Leu Ser Val Thr Ala Arg Leu Ala Ala Ile Arg
              2090                2095                2100

Gln Val Leu Glu Arg Lys Asp Ser Phe Thr Val Ile Ala Met Asp
              2105                2110                2115

Ala Lys Ala Cys Tyr Gly Ala Leu Glu Arg Ser Cys Gly Ile Cys
              2120                2125                2130

Cys Gln Gly Glu Phe Gln Asp Pro Lys Val Ala Thr Trp Leu Leu
              2135                2140                2145

Asp Pro Gly Ala Lys Glu Lys Asn Leu His Arg Met Val His Asp
              2150                2155                2160

Tyr Leu Pro Leu Glu Ala Phe Leu Leu Glu Asp Ile Gly Gly Gly
              2165                2170                2175

Val Gly Tyr Gly Ser Ile Gly Met Ser Pro Glu Asn Pro Gly Ser
              2180                2185                2190

Ser Arg Val Arg Ser Cys Thr Glu Ala Val Leu Leu Thr His Leu
              2195                2200                2205

Met Gln Phe Tyr Thr Leu Cys Phe Asn Asp Glu Glu Cys Glu Arg
              2210                2215                2220

Gln Lys Asn Ile Met Val Ala Arg Leu Gly Asp Leu Glu Glu Gln
              2225                2230                2235

Ala Tyr Arg Cys Val Gly His Gln Phe Ser Leu Thr Ser Thr Glu
              2240                2245                2250

Asp Leu Ser Gln Ile Leu Phe Ile Glu Leu Gln Leu Pro Val Asn
              2255                2260                2265

Gly Asp Pro Ser Ser Leu Gly Gln Pro Met Arg Pro Asn Arg Arg
              2270                2275                2280

Ala Pro Asn Ser His Arg Gly Arg Gln Lys Ser Gln Phe Ser Thr
              2285                2290                2295

Thr Lys Glu Val Leu Glu Lys Leu Arg Pro Leu His Pro Phe Pro
              2300                2305                2310

Gly Ile Leu Leu Glu Trp Arg Arg Ile Ser Gly Ser Leu Thr Lys
              2315                2320                2325

Val Val Phe Ala Leu Gln Lys Glu Lys Val Tyr Cys Glu Asn Leu
              2330                2335                2340

Gly Met His Arg Ile Phe Thr Asp Val Gln Tyr Phe Thr Ala Thr
              2345                2350                2355

Gly Arg Val Ser Leu Ser Glu Pro Asn Leu Gln Asn Val Pro Lys
              2360                2365                2370

Asp Phe Leu Ile Ser Val Ser Ala Pro Val Glu Asn Phe Asn Gln
              2375                2380                2385

Trp Asp Ala Ala Gly His Arg Asn Lys Asn Arg Asn Ser Gly Gln
              2390                2395                2400

Thr Ser Phe Asn Val Ser Met Arg His Ala Phe Ile Pro Phe Pro
              2405                2410                2415

Gly Gly Val Leu Leu Ala Ala Asp Tyr Ser Gln Leu Glu Leu Arg
              2420                2425                2430

Met Ile Ala His Leu Ser Gln Asp Ser Lys Leu Ile Lys Ile Leu
              2435                2440                2445
```

Asn Gly Asp Gly Asp Val Phe Lys Leu Ile Thr Ala Gln Trp Lys
            2450                2455                2460

Ser Ile Ser Val Glu Glu Val Thr Pro Glu Gln Arg Gln Gln Ala
        2465                2470                2475

Lys Gln Ile Cys Tyr Gly Met Ile Tyr Gly Ile Gly Ala Lys Ala
    2480                2485                2490

Leu Gly Asp Thr Leu Gly Val Glu Glu Asn Asp Ala Ala Ala Phe
    2495                2500                2505

Ile Gln Thr Phe Lys Ser Lys Tyr Pro Gly Met Arg Arg Tyr Leu
2510                2515                2520

Lys Asp Thr Val Asp Lys Cys Cys Lys Asn Gly Tyr Val Glu Thr
    2525                2530                2535

Ile Ser Gly Arg Arg Arg Tyr Leu Pro Ser Ile Ser Asn Lys Lys
    2540                2545                2550

Pro Tyr Val Arg Ala His Ala Glu Arg Gln Ala Val Asn Thr Thr
    2555                2560                2565

Val Gln Gly Ser Ala Ala Asp Leu Val Lys Val Ala Met Asn Arg
    2570                2575                2580

Ile Asp Asp Arg Leu Ser Ala Met Phe Pro Leu Ser Lys Lys Thr
    2585                2590                2595

Phe Ser Tyr Lys Glu Asp Glu Val Gln Gly Ile Glu Leu Ser Ser
    2600                2605                2610

Asp Arg Cys Cys Leu Val Leu Gln Leu His Asp Glu Leu Ile Tyr
    2615                2620                2625

Glu Val Thr Glu Arg Cys Leu Gly Gln Ala Ala Lys Val Ile Lys
    2630                2635                2640

Glu Glu Met Glu Thr Ala Met Thr Leu Ser Val Lys Met Pro Val
    2645                2650                2655

Lys Val Lys Ser Gly Leu Ser Trp Ala Thr Met Gln Asp Leu Ala
    2660                2665                2670

Val

<210> SEQ ID NO 18
<211> LENGTH: 2544
<212> TYPE: PRT
<213> ORGANISM: Mus musculus

<400> SEQUENCE: 18

Met Ser Leu Pro Arg Arg Ser Arg Lys Arg Arg Ser Ser Ser Gly
1               5                   10                  15

Ser Asp Thr Phe Ser Gly Asp Gly Asp Ser Phe Val Ser Pro Gln Leu
            20                  25                  30

Arg Cys Gly Pro Val Leu Ser Pro Pro Gly Leu Gly Arg Gly Arg
        35                  40                  45

Arg Leu Thr Gly Thr Gly Thr Asn Lys Arg Arg Val Ser Asp Asp Gln
    50                  55                  60

Ile Asp Gln Leu Leu Leu Ala Asn Trp Gly Leu Pro Lys Ala Val Leu
65                  70                  75                  80

Glu Lys Tyr His Ser Phe Gly Val Arg Lys Met Phe Glu Trp Gln Ala
                85                  90                  95

Glu Cys Leu Leu Leu Gly His Val Leu Glu Gly Lys Asn Leu Val Tyr
            100                 105                 110

Ser Ala Pro Thr Ser Ala Gly Lys Thr Leu Val Ala Glu Leu Leu Ile
        115                 120                 125

```
Leu Lys Arg Val Leu Glu Thr Arg Lys Lys Ala Leu Phe Ile Leu Pro
    130                 135                 140

Phe Val Ser Val Ala Lys Glu Lys Lys Cys Tyr Leu Gln Ser Leu Phe
145                 150                 155                 160

Gln Glu Val Gly Leu Lys Val Asp Gly Tyr Met Gly Ser Thr Ser Pro
                165                 170                 175

Thr Gly Gln Phe Ser Ser Leu Asp Ile Ala Val Cys Thr Ile Glu Arg
                180                 185                 190

Ala Asn Gly Leu Val Asn Arg Leu Ile Glu Glu Asn Lys Met Asp Leu
                195                 200                 205

Leu Gly Met Val Val Asp Glu Leu His Met Leu Gly Asp Ser His
    210                 215                 220

Arg Gly Tyr Leu Leu Glu Leu Leu Thr Lys Ile Cys Tyr Val Thr
225                 230                 235                 240

Arg Lys Ser Ala Ser His Gln Ala Glu Ser Ala Ser Thr Leu Ser Asn
                245                 250                 255

Ala Val Gln Ile Val Gly Met Ser Ala Thr Leu Pro Asn Leu Gln Leu
                260                 265                 270

Val Ala Ser Trp Leu Asn Ala Glu Leu Tyr His Thr Asp Phe Arg Pro
        275                 280                 285

Val Pro Leu Leu Glu Ser Ile Lys Ile Gly Asn Ser Ile Tyr Asp Ser
    290                 295                 300

Ser Met Lys Leu Val Arg Glu Phe Gln Pro Leu Leu Gln Val Lys Gly
305                 310                 315                 320

Asp Glu Asp His Ile Val Ser Leu Cys Tyr Glu Thr Ile Gln Asp Asn
                325                 330                 335

His Ser Val Leu Ile Phe Cys Pro Ser Lys Lys Trp Cys Glu Lys Val
                340                 345                 350

Ala Asp Ile Ile Ala Arg Glu Phe Tyr Asn Leu His His Gln Pro Glu
                355                 360                 365

Gly Leu Val Lys Ser Ser Glu Phe Pro Pro Val Ile Leu Asp Gln Lys
    370                 375                 380

Ser Leu Leu Glu Val Met Asp Gln Leu Lys Arg Ser Pro Ser Gly Leu
385                 390                 395                 400

Asp Ser Val Leu Lys Asn Thr Val Pro Trp Gly Val Ala Phe His His
                405                 410                 415

Ala Gly Leu Thr Phe Glu Glu Arg Asp Ile Ile Glu Gly Ala Phe Arg
                420                 425                 430

Gln Gly Phe Ile Arg Val Leu Ala Ala Thr Ser Thr Leu Ser Ser Gly
        435                 440                 445

Val Asn Leu Pro Ala Arg Arg Val Ile Ile Arg Thr Pro Ile Phe Ser
    450                 455                 460

Gly Gln Pro Leu Asp Ile Leu Thr Tyr Lys Gln Met Val Gly Arg Ala
465                 470                 475                 480

Gly Arg Lys Gly Val Asp Thr Met Gly Glu Ser Ile Leu Val Cys Lys
                485                 490                 495

Asn Ser Glu Lys Ser Lys Gly Ile Ala Leu Leu Gln Gly Ser Leu Glu
                500                 505                 510

Pro Val His Ser Cys Leu Gln Arg Gln Gly Glu Val Thr Ala Ser Met
        515                 520                 525

Ile Arg Ala Ile Leu Glu Ile Ile Val Gly Gly Val Ala Ser Thr Ser
    530                 535                 540
```

-continued

Gln Asp Met Gln Thr Tyr Ala Ala Cys Thr Phe Leu Ala Ala Ala Ile
545                 550                 555                 560

Gln Glu Gly Lys Gln Gly Met Gln Arg Asn Gln Asp Ala Gln Leu
            565                 570                 575

Gly Ala Ile Asp Ala Cys Val Thr Trp Leu Leu Glu Asn Glu Phe Ile
                580                 585                 590

Gln Val Ala Glu Pro Gly Asp Gly Thr Gly Gly Lys Val Tyr His Pro
            595                 600                 605

Thr His Leu Gly Ser Ala Thr Leu Ser Ser Ser Leu Ser Pro Thr Asp
            610                 615                 620

Thr Leu Asp Ile Phe Ala Asp Leu Gln Arg Ala Met Lys Gly Phe Val
625                 630                 635                 640

Leu Glu Asn Asp Leu His Ile Val Tyr Leu Val Thr Pro Val Phe Glu
                645                 650                 655

Asp Trp Ile Ser Ile Asp Trp Tyr Arg Phe Phe Cys Leu Trp Glu Lys
                660                 665                 670

Leu Pro Thr Ser Met Lys Arg Val Ala Glu Leu Val Gly Val Glu Glu
            675                 680                 685

Gly Phe Leu Ala Arg Cys Val Lys Gly Lys Val Val Ala Arg Thr Glu
690                 695                 700

Arg Gln His Arg Gln Met Ala Ile His Lys Arg Phe Phe Thr Ser Leu
705                 710                 715                 720

Val Leu Leu Asp Leu Ile Ser Glu Ile Pro Leu Lys Asp Ile Asn Gln
                725                 730                 735

Lys Tyr Gly Cys Asn Arg Gly Gln Ile Gln Ser Leu Gln Gln Ser Ala
            740                 745                 750

Ala Val Tyr Ala Gly Met Ile Thr Val Phe Ser Asn Arg Leu Gly Trp
            755                 760                 765

His Asn Met Glu Leu Leu Leu Ser Gln Phe Gln Lys Arg Leu Thr Phe
            770                 775                 780

Gly Ile Gln Arg Glu Leu Cys Asp Leu Ile Arg Val Ser Leu Leu Asn
785                 790                 795                 800

Ala Gln Arg Ala Arg Phe Leu Tyr Ala Ser Gly Phe Leu Thr Val Ala
            805                 810                 815

Asp Leu Ala Arg Ala Asp Ser Ala Glu Val Glu Val Ala Leu Lys Asn
            820                 825                 830

Ser Leu Pro Phe Lys Ser Ala Arg Lys Ala Val Asp Glu Glu Glu Glu
            835                 840                 845

Ala Ala Glu Glu Arg Arg Ser Met Arg Thr Ile Trp Val Thr Gly Lys
850                 855                 860

Gly Leu Ser Ala Arg Glu Ala Ala Ala Leu Ile Val Glu Glu Ala Lys
865                 870                 875                 880

Met Ile Leu Gln Gln Asp Leu Ile Glu Met Gly Val Arg Trp Asp Pro
            885                 890                 895

Lys Ser Pro Leu Ser Ser Ser Thr His Ser Arg Thr Ser Thr Ser Glu
            900                 905                 910

Val Lys Glu His Thr Phe Lys Ser Gln Thr Lys Ser Ser His Lys Arg
            915                 920                 925

Leu Ala Ser Met Gly Arg Asn Ser Ile Arg Ala Ser Gly Ser Asn Asp
            930                 935                 940

Lys Pro Ser Pro Asp Ala Glu Arg Gly Ile Asp Asp Cys Ser Glu His
945                 950                 955                 960

Ala Asp Ser Leu Cys Lys Phe Gln Gly Asn Phe Glu Pro Gln Thr Pro

-continued

```
                965                 970                 975
Ser Ile Cys Thr Ala Arg Lys Arg Thr Ser Leu Gly Ile Asn Lys Glu
            980                 985                 990
Met Leu Arg Lys Ser Leu Lys Glu Gly Lys Pro Ser Thr Lys Glu Val
            995                 1000                1005
Leu Gln Thr Phe Ser Ser Glu Lys Thr Arg Lys Thr Ala Leu Ser
        1010                1015                1020
Phe Ser Ser Glu Gln Val Asn Asn Thr Leu Pro Ser Gly Arg Asp
        1025                1030                1035
Arg Lys Tyr Gln Lys Lys Ser Trp Gly Ser Ser Pro Val Arg Asp
        1040                1045                1050
Ser Gly Met His Arg Gly Asp Leu Gln Gly Gln Thr Met Cys Thr
        1055                1060                1065
Ser Ala Leu Cys Glu Asp Ser Gln Lys Ser Leu Glu Glu Gln Asn
        1070                1075                1080
Ala Glu Phe Arg Ser Pro Gly Leu Phe Ala Lys His Leu Pro Ser
        1085                1090                1095
Cys Ala Lys Glu Lys Cys Lys Lys Pro Ser Leu Pro Leu Gln Arg
        1100                1105                1110
Gln Gln Ala Cys Ser Arg Arg Ser Thr Glu Ser Cys Ala Ala Val
        1115                1120                1125
Gly His Pro Ala Ala Gly Ser Ser Pro Ala Ala Arg Asp Arg
        1130                1135                1140
Arg Gly Leu Ala Ala Arg Glu Thr Glu Lys Gly Asn Glu Ala Leu
        1145                1150                1155
Thr Glu Asn Gly Gly Glu Ser Gln Leu Gln Asp Thr Tyr Pro Val
        1160                1165                1170
Ser Gln Tyr Leu Glu Tyr His Ser Glu Lys His Thr Asn Thr Cys
        1175                1180                1185
Thr Arg Gln Lys Thr Leu Thr Glu Gly Gln Ala Gly Ser Ser Tyr
        1190                1195                1200
Val Ala Arg Asp Ser Asn Asp Ala Ala Pro Ile Lys Cys Glu Arg
        1205                1210                1215
Met Lys Leu Asn Ser Lys Asp Arg Asp Ser Asn Pro Cys Arg Gln
        1220                1225                1230
Ala Leu Gly Ser Tyr Thr Gly Arg Thr Glu Ala Leu Gln Ser Thr
        1235                1240                1245
Ala Lys Leu Gly Gln Ala Gly Gly Gln Cys Glu Asn Leu Leu Asn
        1250                1255                1260
Ser Ser Gly Val Gln Gly Lys Thr Gly Ala His Ala Thr Asn Arg
        1265                1270                1275
Thr Glu His Ser His Ala Ser Asn Pro Ala Phe Cys Asp Phe Gly
        1280                1285                1290
Asp Ser Leu Asp Leu Asp Thr Gln Ser Glu Glu Ile Ile Glu Gln
        1295                1300                1305
Met Ala Thr Glu Asn Thr Met Gln Gly Ala Lys Ala Val Val Ile
        1310                1315                1320
Met Glu Glu Gly Ser Ala Met Gln Asn Lys Cys His Ser Thr Pro
        1325                1330                1335
Gly Asp Gln His Val Pro Gly Ala Ala Asn Thr Asp His Val Asp
        1340                1345                1350
Ser Lys Lys Val Glu Ser Val Lys Ala Asn Thr Glu Lys Asn Ile
        1355                1360                1365
```

-continued

Asn Arg Gly Ala Pro Val Ser Leu Ile Phe His Thr Gln Gly Glu
1370              1375              1380

Asn Gly Ala Cys Phe Lys Gly Asn Glu His Ser Val Thr Asp Ser
1385              1390              1395

Gln Leu Asn Ser Phe Leu Gln Gly Phe Glu Thr Gln Glu Ile Val
1400              1405              1410

Lys Pro Ile Ile Pro Leu Ala Pro Gln Met Arg Thr Pro Thr Gly
1415              1420              1425

Val Glu Glu Glu Ser Leu Pro Glu Thr Ser Leu Asn Met Ser Asp
1430              1435              1440

Ser Ile Leu Phe Asp Ser Phe Gly Glu Asp Gly Phe Gly Gln Gly
1445              1450              1455

Gln Ser Pro Asp Ile Lys Ala Asn Gln Pro Leu Leu Ser Glu Met
1460              1465              1470

Thr Pro Asn His Phe Ser Asn Pro Pro His Pro Gln Glu Asp Pro
1475              1480              1485

Val Met Thr Pro Thr Val Ser Glu Pro Gln Gly Thr Gln Gln Gln
1490              1495              1500

Gly Val Cys Leu Ser Gly Glu Ser Ile Ile Phe Ser Asp Ile Asp
1505              1510              1515

Ser Ala Gln Val Ile Glu Ala Leu Asp Asn Met Ala Ala Phe His
1520              1525              1530

Val Gln Glu Asn Cys Asn Ser Val Ala Leu Lys Thr Leu Glu Pro
1535              1540              1545

Ser Asp Ser Ala Val Leu Gly Asn Glu Cys Pro Gln Gly Lys Leu
1550              1555              1560

Val Arg Gly Asp Gln Asn Glu Gly Ser Pro Lys Pro Lys Leu Thr
1565              1570              1575

Glu Thr Asn Gln Asp Asn Ser Phe Thr Trp Ser Gly Ala Ser Phe
1580              1585              1590

Asn Leu Ser Pro Glu Leu Gln Arg Ile Leu Asp Lys Val Ser Ser
1595              1600              1605

Pro Arg Glu Asn Glu Lys Pro Lys Met Ile His Val Asn Leu Ser
1610              1615              1620

Ser Phe Glu Gly Asn Ser Lys Glu Ser His Glu Arg Glu Glu Ile
1625              1630              1635

Asn Ser Asp Leu Gly Thr Val Gln Arg Thr Ser Val Phe Pro Ser
1640              1645              1650

Asn Glu Val Lys Asn Arg Thr Glu Gly Leu Glu Ser Lys Ala Arg
1655              1660              1665

His Gly Gly Ala Ser Ser Pro Leu Pro Arg Lys Glu Ser Ala Ala
1670              1675              1680

Ala Asp Asp Asn Gly Leu Ile Pro Pro Thr Pro Val Pro Ala Ser
1685              1690              1695

Ala Ser Lys Val Ala Phe Pro Glu Ile Leu Gly Thr Ser Val Lys
1700              1705              1710

Arg Gln Lys Ala Ser Ser Ala Leu Gln Pro Gly Glu Ser Cys Leu
1715              1720              1725

Phe Gly Ser Pro Ser Asp Asn Gln Asn Gln Asp Leu Ser Gln Glu
1730              1735              1740

Leu Arg Asp Ser Leu Lys Asp Tyr Asp Gly Ser Val Ala Asp Thr
1745              1750              1755

```
Ser  Phe  Phe  Leu  Gln  Ser  Gln  Asp  Gly  Leu  Leu  Leu  Thr  Gln  Ala
1760                1765                     1770

Ser  Cys  Ser  Ser  Glu  Ser  Leu  Ala  Ile  Ile  Asp  Val  Ala  Ser  Asp
1775                1780                     1785

Gln  Ile  Leu  Phe  Gln  Thr  Phe  Val  Lys  Glu  Trp  Gln  Cys  Gln  Lys
1790                1795                     1800

Arg  Phe  Ser  Ile  Ser  Leu  Ala  Cys  Glu  Lys  Met  Thr  Ser  Ser  Met
1805                1810                     1815

Ser  Ser  Lys  Thr  Ala  Thr  Ile  Gly  Gly  Lys  Leu  Lys  Gln  Val  Ser
1820                1825                     1830

Leu  Pro  Gln  Glu  Ala  Thr  Val  Glu  Asp  Ala  Gly  Phe  Pro  Val  Arg
1835                1840                     1845

Gly  Cys  Asp  Gly  Ala  Val  Val  Val  Gly  Leu  Ala  Val  Cys  Trp  Gly
1850                1855                     1860

Ala  Lys  Asp  Ala  Tyr  Tyr  Leu  Ser  Leu  Gln  Lys  Glu  Gln  Lys  Gln
1865                1870                     1875

Ser  Glu  Ile  Ser  Pro  Ser  Leu  Ala  Pro  Pro  Leu  Asp  Ala  Thr
1880                1885                     1890

Leu  Thr  Val  Lys  Glu  Arg  Met  Glu  Cys  Leu  Gln  Ser  Cys  Leu  Gln
1895                1900                     1905

Lys  Lys  Ser  Asp  Arg  Glu  Arg  Ser  Val  Val  Thr  Tyr  Asp  Phe  Ile
1910                1915                     1920

Gln  Thr  Tyr  Lys  Val  Leu  Leu  Leu  Ser  Cys  Gly  Ile  Ser  Leu  Glu
1925                1930                     1935

Pro  Ser  Tyr  Glu  Asp  Pro  Lys  Val  Ala  Cys  Trp  Leu  Leu  Asp  Pro
1940                1945                     1950

Asp  Ser  Lys  Glu  Pro  Thr  Leu  His  Ser  Ile  Val  Thr  Ser  Phe  Leu
1955                1960                     1965

Pro  His  Glu  Leu  Ala  Leu  Leu  Glu  Gly  Met  Glu  Thr  Gly  Pro  Gly
1970                1975                     1980

Ile  Gln  Ser  Leu  Gly  Leu  Asn  Val  Asn  Thr  Glu  His  Ser  Gly  Arg
1985                1990                     1995

Tyr  Arg  Ala  Ser  Val  Glu  Ser  Val  Leu  Ile  Phe  Asn  Ser  Met  Asn
2000                2005                     2010

Gln  Leu  Asn  Ser  Leu  Leu  Gln  Lys  Glu  Asn  Leu  His  Asp  Ile  Phe
2015                2020                     2025

Cys  Lys  Val  Glu  Met  Pro  Ser  Gln  Tyr  Cys  Leu  Ala  Leu  Leu  Glu
2030                2035                     2040

Leu  Asn  Gly  Ile  Gly  Phe  Ser  Thr  Ala  Glu  Cys  Glu  Ser  Gln  Lys
2045                2050                     2055

His  Val  Met  Gln  Ala  Lys  Leu  Asp  Ala  Ile  Glu  Thr  Gln  Ala  Tyr
2060                2065                     2070

Gln  Leu  Ala  Gly  His  Ser  Phe  Ser  Phe  Thr  Ser  Ala  Asp  Asp  Ile
2075                2080                     2085

Ala  Gln  Val  Leu  Phe  Leu  Glu  Leu  Lys  Leu  Pro  Pro  Asn  Gly  Glu
2090                2095                     2100

Met  Lys  Thr  Gln  Gly  Ser  Lys  Lys  Thr  Leu  Gly  Ser  Thr  Arg  Arg
2105                2110                     2115

Gly  Asn  Glu  Ser  Gly  Arg  Arg  Met  Arg  Leu  Gly  Arg  Gln  Phe  Ser
2120                2125                     2130

Thr  Ser  Lys  Asp  Ile  Leu  Asn  Lys  Leu  Lys  Gly  Leu  His  Pro  Leu
2135                2140                     2145

Pro  Gly  Leu  Ile  Leu  Glu  Trp  Arg  Arg  Ile  Ser  Asn  Ala  Ile  Thr
```

```
                2150                2155                2160
Lys Val Val Phe Pro Leu Gln Arg Glu Lys His Leu Asn Pro Leu
    2165                2170                2175
Leu Arg Met Glu Arg Ile Tyr Pro Val Ser Gln Ser His Thr Ala
    2180                2185                2190
Thr Gly Arg Ile Thr Phe Thr Glu Pro Asn Ile Gln Asn Val Pro
    2195                2200                2205
Arg Asp Phe Glu Ile Lys Met Pro Thr Leu Val Arg Glu Ser Pro
    2210                2215                2220
Pro Ser Gln Ala Pro Lys Gly Arg Phe Pro Met Ala Ile Gly Gln
    2225                2230                2235
Asp Lys Lys Val Tyr Gly Leu His Pro Gly His Arg Thr Gln Met
    2240                2245                2250
Glu Glu Lys Ala Ser Asp Arg Gly Val Pro Phe Ser Val Ser Met
    2255                2260                2265
Arg His Ala Phe Val Pro Phe Pro Gly Gly Leu Ile Leu Ala Ala
    2270                2275                2280
Asp Tyr Ser Gln Leu Glu Leu Arg Ile Leu Ala His Leu Ser Arg
    2285                2290                2295
Asp Cys Arg Leu Ile Gln Val Leu Asn Thr Gly Ala Asp Val Phe
    2300                2305                2310
Arg Ser Ile Ala Ala Glu Trp Lys Met Ile Glu Pro Asp Ala Val
    2315                2320                2325
Gly Asp Asp Leu Arg Gln His Ala Lys Gln Ile Cys Tyr Gly Ile
    2330                2335                2340
Ile Tyr Gly Met Gly Ala Lys Ser Leu Gly Glu Gln Met Gly Ile
    2345                2350                2355
Lys Glu Asn Asp Ala Ala Ser Tyr Ile Asp Ser Phe Lys Ser Arg
    2360                2365                2370
Tyr Lys Gly Ile Asn His Phe Met Arg Asp Thr Val Lys Asn Cys
    2375                2380                2385
Arg Lys Asn Gly Phe Val Glu Thr Ile Leu Gly Arg Arg Arg Tyr
    2390                2395                2400
Leu Pro Gly Ile Lys Asp Asp Asn Pro Tyr His Lys Ala His Ala
    2405                2410                2415
Glu Arg Gln Ala Ile Asn Thr Thr Val Gln Gly Ser Ala Ala Asp
    2420                2425                2430
Ile Val Lys Ile Ala Thr Val Asn Ile Gln Lys Gln Leu Glu Thr
    2435                2440                2445
Phe Arg Ser Thr Phe Lys Ser His Gly His Arg Glu Ser Met Leu
    2450                2455                2460
Gln Asn Asp Arg Thr Gly Leu Leu Pro Lys Arg Lys Leu Lys Gly
    2465                2470                2475
Met Phe Cys Pro Met Arg Gly Gly Phe Phe Ile Leu Gln Leu His
    2480                2485                2490
Asp Glu Leu Leu Tyr Glu Val Ala Glu Glu Asp Val Val Gln Val
    2495                2500                2505
Ala Gln Ile Val Lys Asn Glu Met Glu Cys Ala Ile Lys Leu Ser
    2510                2515                2520
Val Lys Leu Lys Val Lys Val Lys Ile Gly Ala Ser Trp Gly Glu
    2525                2530                2535
Leu Lys Asp Phe Asp Val
    2540
```

<210> SEQ ID NO 19
<211> LENGTH: 2397
<212> TYPE: DNA
<213> ORGANISM: artificial sequence
<220> FEATURE:
<223> OTHER INFORMATION: synthetic sequence

<400> SEQUENCE: 19

| | | | | | |
|---|---|---|---|---|---|
| ggcttcaagg | acaatagtcc | gatcagtgac | acttctttca | gtttacagct | gtcacaagac | 60 |
| ggccttcaat | taacacctgc | ctccagctca | tccgaaagcc | tttcgatcat | tgacgtcgcc | 120 |
| tcggatcaaa | atttgttcca | gacctttatt | aaagaatggc | gttgcaaaaa | acgcttcagt | 180 |
| atttcgttgg | cgtgtgaaaa | gatccgctct | cttacgtcca | gtaagacagc | gacaatcggt | 240 |
| tcgcgcttca | agcaggccag | ctcacccaa | gagattccca | tccgcgacga | cggttttcct | 300 |
| atcaaagggt | gtgatgacac | tttggtggtg | ggtctggcag | tttgctgggg | aggacgtgat | 360 |
| gcgtattact | tcagcttgca | gaaagaacaa | aaacactccg | aaatctctgc | gtccttggtc | 420 |
| cccccttcat | tggacccatc | attaacgctt | aaagatcgta | tgtggtactt | gcagagttgt | 480 |
| ttacgcaaag | aaagcgacaa | agaatgtagt | gtggtcatct | atgatttcat | ccagagctac | 540 |
| aaaatcttgt | tgttatcctg | tggcatctct | ctggagcaga | gctatgaaga | tccgaaggta | 600 |
| gcctgttggc | ttttggaccc | ggattcgcaa | gagccaaccc | tgcattcaat | cgtcaccagc | 660 |
| ttccttccac | atgaactgcc | tcttttagag | ggaatggaga | cctcgcaggg | aatccaatct | 720 |
| cttggactta | atgctggatc | tgaacacagt | ggacgctatc | gcgcgtcagt | tgaatcaatc | 780 |
| ctgattttta | actcgatgaa | tcaacttaat | tccctgcttc | agaaagaaaa | ccttcaggac | 840 |
| gtctttcgta | aggtggaaat | gccttcgcaa | tattgcttag | ccttattaga | gttgaatgga | 900 |
| atcggatttt | ccactgcaga | gtgtgagtcc | cagaaacata | tcatgcaggc | caaactggat | 960 |
| gcaatcgaga | cacaagctta | ccagcttgcg | ggtcatagct | tcagcttcac | atcctccgac | 1020 |
| gatatcgccg | aagtcttgtt | tttggaatta | aagctgcctc | ctaatcgcga | gatgaagaat | 1080 |
| caaggctcca | agaagacatt | aggttcaacc | cgccgtggaa | tcgacaatgg | tcgtaaatta | 1140 |
| cgtctgggcc | gccagtttag | cacatctaaa | gacgtcctta | ataagctgaa | agccttgcac | 1200 |
| cctcttccgg | gcctgatttt | ggagtggcgc | cgtattacaa | atgccatcac | caaagtagtt | 1260 |
| ttcccattgc | agcgcgagaa | gtgtcttaat | ccattccttg | ggatgagcg | tatctatccc | 1320 |
| gtcagccagt | cacatactgc | aacgggacgc | attactttca | cggagccaaa | catccaaaat | 1380 |
| gtcccccgcg | acttcgagat | taaaatgcct | actctggttg | gggagtctcc | tcctagccaa | 1440 |
| gctgtgggca | agggactgct | gcctatgggt | cgtggcaaat | acaaaaaggg | ctttagtgtt | 1500 |
| aacccacgct | gccaggctca | gatggaggag | cgcgctgcag | atcgtggaat | gccttttct | 1560 |
| atcagcatgc | gtcacgcatt | cgtcccccttc | ccaggggaa | gtatcttagc | ggctgattac | 1620 |
| tctcaattgg | aacttcgtat | tctggcgcac | cttagtcatg | accgtcgctt | gattcaggta | 1680 |
| ctgaatactg | gagcggacgt | gtttcgttcg | attgctgcgg | agtggaaaat | gatcgagccc | 1740 |
| gaatccgtcg | gtgatgatct | tcgtcaacag | gcaaaacaga | tctgttacgg | gatcatctat | 1800 |
| ggaatgggtg | ctaaatcctt | gggtgagcaa | atggggatta | aggagaacga | tgccgcatgc | 1860 |
| tacattgata | gcttcaaatc | acgttacacc | ggtattaatc | aatttatgac | tgagaccgtg | 1920 |
| aaaaactgta | acgtgacgg | cttcgtccaa | acaattttag | ggcgtcgccg | ctatttaccg | 1980 |
| ggaattaagg | acaacaatcc | ctaccgcaaa | gcacatgccg | aacgtcaagc | aatcaacact | 2040 |

```
attgtccaag gttcggctgc tgatatcgtg aaaattgcca cagtcaacat ccagaaacag    2100
ctggagacgt ttcattcaac atttaaaagc cacggacacc gtgaaggcat gctgcaatcg    2160
gaccaaactg gtctgtcacg taagcgtaaa ttgcagggta tgttctgtcc gattcgcgga    2220
ggcttcttta tcttacaatt acacgacgag ctgttgtatg aagttgccga ggaagatgtc    2280
gtccaggtgg ctcagattgt taagaacgaa atggaatctg ctgtgaagtt gtctgtgaag    2340
cttaaagtca aagttaaaat tggtgcttcg tggggggagt tgaaagactt cgatgtt      2397
```

VARIANTS OF FAMILY A DNA POLYMERASE AND USES THEREOF

FIELD OF THE INVENTION

The invention relates to variants of family A DNA polymerase and uses thereof for the enzymatic synthesis of nucleic acid sequences without template. More particularly, the present invention relates to such variants suitable to incorporate terminator modified nucleotides, for the synthesis of nucleic acid molecules with determined or controlled sequences.

INCORPORATION BY REFERENCE OF SEQUENCE LISTING PROVIDED AS A TEXT FILE

Incorporated by reference in its entirety herein is a computer-readable nucleotide/amino acid sequence listing submitted on Feb. 5, 2020 and identified as follows: one 233 kilobyte file named "DNAS-005_B2560PC00_Seq_ Listing_ST25," created Feb. 4, 2020.

BACKGROUND

Methods for de novo chemical synthesis of nucleic acids based on solid-phase phosphoramidite chemistry have been largely used and refined over the past 40 years. The technique consists of a four-step chain elongation cycle that adds one base per cycle onto a growing oligonucleotide chain attached to a solid support matrix. Although it has been the method of choice to synthesize nucleic acids during the past decades, this technology has some notable limitations: It requires the use of multiple solvents and reagents, and due to limitations in chemical reaction efficiency, the length of synthetic oligonucleotides typically do not exceed 150-200 bases. Moreover, these short fragments need to be further assembled to provide the desired DNA sequence.

One alternative to chemical synthesis consists in using template independent DNA polymerases that will add reversible terminator modified nucleotides to a growing single stranded chain of nucleic acids. This allows the addition of one type of nucleotide per cycle in a controlled fashion.

Some native enzymes are able to act on natural nucleotides in the absence of template and so can catalyze the synthesis of nucleic acids in an uncontrolled fashion. However, they are particularly inefficient to incorporate reversible terminator modified nucleotides. Efforts have been made to develop new DNA polymerases able to act on modified nucleotides but the resulting enzymes are not fully satisfactory in term of performance for the synthesis of any type of nucleic acids.

So far only few DNA polymerases that can act efficiently on single strand DNA (without the use of template) have been identified. The most characterized polymerase having such template-independent activity is the Terminal deoxynucleotidyl Transferase (TdT). TdT enzymes have been extensively used to modify single stranded DNA for various types of applications including biotechnology, biomedical research and synthetic biology. However, native TdT is poorly able to use 3'modified nucleotides.

It has also been discovered recently that the human DNA polymerase Pol θ possesses a robust template-independent activity using optimized conditions. In particular, this enzyme is known to be more effective in transferring ribonucleotides to single stranded DNA compared to TdT. As for TdT, the native DNA polymerase Pol θ is unable to recognize efficiently 3'-modified nucleotides.

There is therefore a need to develop new robust and efficient DNA polymerases capable to use modified nucleotides in the absence of template to provide an improved method for the nucleic acid synthesis.

SUMMARY OF THE INVENTION

It is therefore an object of the present invention to provide a variant of a DNA polymerase of family A, and more particularly of a Pol θ, which is able to incorporate a modified terminator nucleotide during the nucleic acid fragment synthesis.

More particularly, it is an object of the invention to provide a variant of a DNA polymerase of family A, which (i) comprises the amino acid sequence set forth in SEQ ID No 2 or a functionally equivalent sequence, with at least one amino acid mutation at any one of the amino acid residue as compared to SEQ ID No 2, (ii) is able to synthesize a nucleic acid fragment without template and (iii) is able to incorporate a modified terminator nucleotide during a nucleic acid fragment synthesis.

Preferably, the variant is a variant of Pol θ, which has at least 40% identity with the amino acid sequence set forth in SEQ ID No 1.

Preferably, the variant shows an increased ability to incorporate a reversible modified terminator nucleotide during a nucleic acid fragment synthesis as compared to a DNA polymerase of SEQ ID No 1.

According to an embodiment, the variant is able to incorporate a 3'O-modified nucleotide.

In an embodiment, the variant comprises at least one mutation, preferably selected from a substitution, a deletion or an addition, in at least one of the amino acid sequence as set forth in SEQ ID No 3, SEQ ID No 4, SEQ ID No 5 or SEQ ID No 6, or functionally equivalent sequences.

For instance, the variant comprises at least one substitution in the amino acid sequence as set forth in SEQ ID No 3, selected from the group consisting of D2330E/R/H/K/T/V/A/G, Y2331F/W/P/H/M/L/V/A, S2332T/N/Q/V/A/G, Q2333N/T/S/A/G/V, L2334M/E/N/F/K/D/A/G, E2335G/A/N/T/S/D, L2336M/E/N/F/K/D/A/G, R2337H/K/D/E/A/G/M/F, I2338V/A/G/L/T/S/D/K/M, L2339M/E/N/F/K/D/A/G/I, wherein the positions are numbered by reference to the amino acid sequence set forth in SEQ ID No 1.

Alternatively or in addition, the variant may comprise at least one substitution in the amino acid sequence as set forth in SEQ ID No 4 selected from the group consisting of P2322A/V/I/L/G/C, G2323C/P/A/V/K/D, G2324C/P/A/V/K/D, S2325L/N/M/V/T/A/G/D/K, I2326V/A/G/L/T/S/D/K/M, L2327M/E/N/F/K/D/A/G/I/V, A2328V/T/G, A2329V/T/G, wherein the positions are numbered by reference to the amino acid sequence set forth in SEQ ID No 1.

Alternatively or in addition, the variant may comprise at least one substitution in the amino acid sequence as set forth in SEQ ID No 5 selected from the group consisting of D2376E/R/H/K/T/V/A/G/N, D2377E/R/H/K/T/V/A/G/N, L2378M/E/N/F/K/D/A/G/I, R2379H/K/D/E/A/G/M/F, Q2380N/T/S/A/G/V, Q2381N/T/S/A/G/V, A2382V/T/G, K2383R/H/D/E/Q/N/C/A/G/S/T, Q2384N/T/S/A/G/V, I2385V/A/G/L/T/S/D/K/M, C2386G/P/A/V/S/N/Q/D/K, Y2387F/W/P/H/M/L/V/A, G2388C/P/A/V/K/D, I2389V/A/G/L/T/S/D/K/M, I2390V/A/G/L/T/S/D/K/M, Y2391F/W/P/H/M/L/V/A, wherein the positions are numbered by reference to the amino acid sequence set forth in SEQ ID No 1.

Alternatively or in addition, the variant may comprise at least one substitution in the amino acid sequence as set forth in SEQ ID No 6 selected from the group consisting of E2199G/A/N/T/S/D/K, W2200Y/F/P/L/I/V/A/G/E, R2201H/K/D/E/A/G/M/F/S/P, R2202H/K/D/E/A/G/M/F/S/P, I2203V/A/G/L/T/S/D/K/M/P, T2204S/N/Q/C/G/M/K/D, wherein the positions are numbered by reference to the amino acid sequence set forth in SEQ ID No 1.

In an embodiment, the variant comprises at least one amino acid mutation, preferably of at least two mutations, more preferably three mutation at position(s) corresponding to residues selected from D2330, D2540 or E2541, or residues functionally equivalent, excluding D2540N/A or E2541Q/A, wherein the positions are numbered by reference to the amino acid sequence set forth in SEQ ID No 1. Preferably, the amino acid mutations are amino acid substitutions selected from D2330E/R/H/K/T/V/A/G, D2540E/K/R/H/Q/S/T/C and E2541D/R/H/K/N/S/T/C, wherein the positions are numbered by reference to the amino acid sequence set forth in SEQ ID No 1.

In an embodiment, the variant comprises at least one amino acid mutation, preferably selected from a substitution, a deletion or an addition, at position(s) corresponding to residues selected from K2181, R2315, F2359, Y2391 and A2477, or residues functionally equivalent, excluding substitution K2181A and deletion of R2315. Preferably, the mutation is a substitution selected from K2181R/H/D/E/Q/N/C/G/S/T, R2315H/K/D/E/A/G/M/F, F2359M/L/I/V/A/G/P/T/K/D, A2477V/T/G.

In an embodiment, the variant comprises at least one amino acid mutation of a residue having side chain groups positioned within 15 Å, 12 Å, 10 Å, 8 Å or 6 Å of a 3'O extremity of a nucleotide, or residue functionally equivalent.

In an embodiment, the variant comprises at least substitution or combination of substitutions as listed in TABLE 9, wherein the positions are numbered by reference to the amino acid sequence set forth in SEQ ID No 1.

In an embodiment, the variant further comprises the amino acid sequence as set forth in SEQ ID No 7.

In an embodiment, the variant has at least 75%, 80%, 85%, 90%, 95%, 97%, 98% or 99% identity to the full length amino acid sequence set forth in SEQ ID No 1, It is also an object of the invention to provide a nucleic acid molecule encoding a variant of a DNA polymerase of family A of the invention.

It is a further object of the invention to provide an expression vector comprising such nucleic acid molecule.

It is a further object of the invention to provide a host cell comprising such nucleic acid molecule or such expression vector.

The present invention also provide a process for producing a variant of a DNA polymerase of family A of the invention, wherein a host cell of the invention is cultivated under culture conditions allowing the expression of the nucleic acid encoding said variant, and wherein the variant is optionally retrieved.

It is also the purpose of the invention to provide the Use of such a variant of a DNA polymerase of family A, for synthesizing a nuclei acid molecule without template, with 3'O-modified nucleotide.

The present invention also provides a process for synthesizing a nucleic acid molecule with template, comprising a step of contacting a nucleic acid primer with both at least one nucleotide, preferably at least one 3'O-modified nucleotide, and a DNA polymerase of family A of the invention.

The present invention also provides a kit for performing a nucleotide incorporation reaction comprising a DNA polymerase of family A of the invention, and one or more nucleotides, preferably one or more 3'O-modified nucleotides, and optionally at least one nucleic acid primer.

DESCRIPTION OF THE INVENTION

Figure 1:
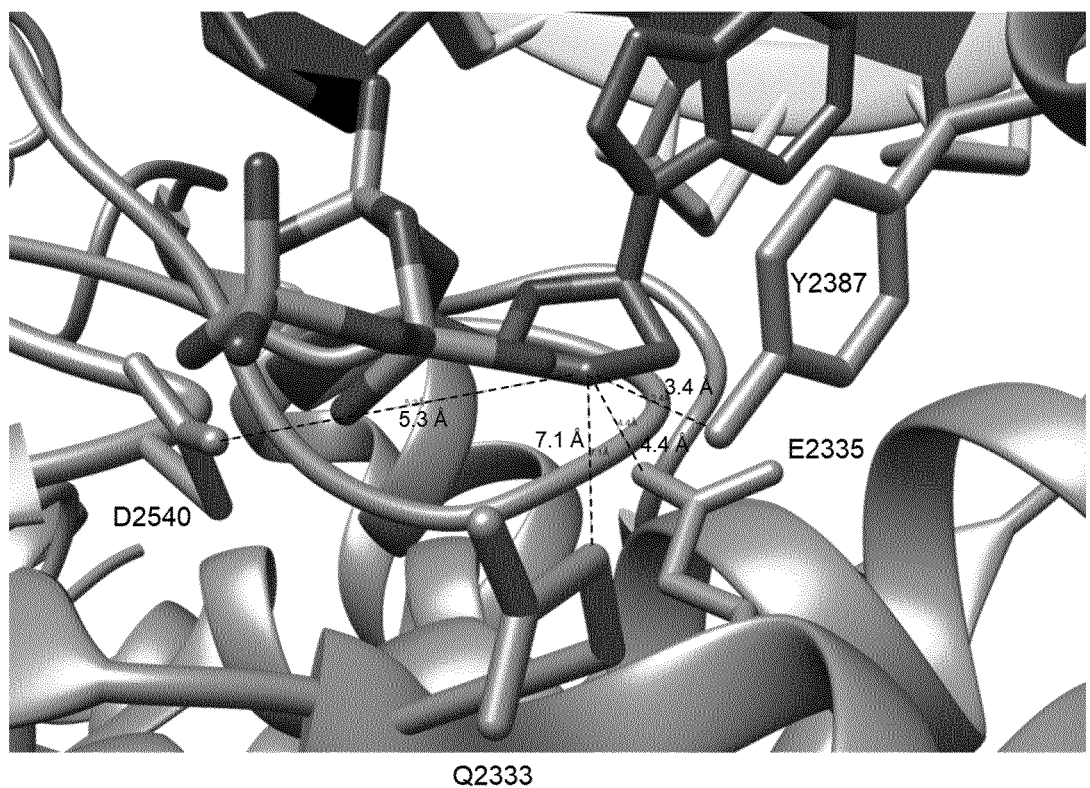
FIG. 1: Structural analysis of the catalytic pocket of the Human Pol Theta (Pol θ) polymerase using PDB crystal structure 4X0P and Chimera software. The picture shows 4 residues Q2333, E2335, Y2387 and D2540 and their respective distance (in angstrom) to the 3' extremity of the sugar ring of a ddATP.

The present invention relates to variants of Family A DNA polymerase, which exhibit increased ability to incorporate modified reversible terminator nucleotides as compared to parent or native Family A DNA polymerases.

Definitions

The DNA polymerase families are divided into seven families based on their sequence homology and crystal structure. Among them, the polymerases of family A are classes either replicative polymerases or repair polymerases. Polymerases from family A are present across very wide range of organisms and microorganisms. Eukaryote and prokaryote cells are expressing polymerases from Family A. Among animals both vertebrates and invertebrates express Family A polymerases. The replicative polymerases have the best fidelity rate and require template strand for activity. The repair polymerases are involved in reparation of various DNA lesions or errors. They show a largely decrease fidelity but retain a high activity rate even in presence of degraded template or for some particular polymerases in absence of template.

The present invention relates of the engineering and subsequent modifications of A Family polymerase. In a particular aspect of the invention the Family A polymerase are from the repair type and have the ability to conserve a high nucleotide incorporation rate even if the template strand is absent.

Polymerase Theta (Pol θ) is a particular polymerase of the A Family. Pol θ belongs to the repair type of Family A polymerases and is naturally implicated in DNA repair and maintenance mechanisms. In particular Pol θ is able to perform DNA repair activity in very bulky lesions. It also has the unique ability to conserve a nucleotide polymerization activity even when no template strand is present. In specific condition and with natural nucleotides, Pol θ is able to elongate with several hundreds of nucleotides, DNA fragments without any complementary strand to be present.

The present invention relates to the engineering and subsequent modifications of Pol θ polymerase. In a particular aspect of the invention Pol θ is used in such condition that it show polymerization activity in absence of any template strand of DNA or other nucleic acid molecules.

Pol θ is able to polymerize both natural deoxyribonucleotides (dNTP) and ribonucleotides (rNTP). Various modified nucleotides, baring permanent labeled modifications on the base moiety of the nucleotide, have been tested for incorporation with Pol θ. Wild type Pol θ enzyme show little to medium incorporation rate of these permanent labeled base-modified nucleotides. However, incorporation of modified reversible terminator nucleotides is not feasible with wild type Pol θ. In particular Pol θ is unable to incorporate 3'O-reversible modified nucleotides.

The present invention relates to modified family A polymerases able to incorporate modified reversible terminator nucleotides.

In the context of the invention, "modified family A DNA polymerases", "modified family A polymerases", "variants of family A DNA polymerases" and "variants of family A polymerases" refer to enzymes that share at least 25% identity with the amino acid sequence of a family A polymerase and comprises at least the amino acid sequence as set forth in SEQ ID No 2 excepting at least one amino acid residue mutation. Preferably, the variant of family A DNA polymerase is a variant of a Pol θ polymerase sharing at least 40% identity with SEQ ID No 1. Alternatively or in addition, the 3D structure of the variant of a Pol θ polymerase shares at least 60% identity with the 3D structure of human Pol θ polymerase. As used herein, such 3D structure identity means that at least 60% of the amino acid residues of the variant have same position and spatial conformation as amino acid residues in the 3D structure of human Pol θ polymerase.

Herein, the terms "peptide", "polypeptide", "protein", "enzyme", refer to a chain of amino acids linked by peptide bonds, regardless of the number of amino acids forming said chain. The amino acids are herein represented by their one-letter or three-letters code according to the following nomenclature: A: alanine (Ala); C: cysteine (Cys); D: aspartic acid (Asp); E: glutamic acid (Glu); F: phenylalanine (Phe); G: glycine (Gly); H: histidine (His); I: isoleucine (Ile); K: lysine (Lys); L: leucine (Leu); M: methionine (Met); N: asparagine (Asn); P: proline (Pro); Q: glutamine (Gln); R: arginine (Arg); S: serine (Ser); T: threonine (Thr); V: valine (Val); W: tryptophan (Trp) and Y: tyrosine (Tyr).

Accordingly, the terms "mutant" and "variant" may be used interchangeably to refer to polypeptides derived from SEQ ID No 2 and comprising a modification or an alteration, i.e., a substitution, insertion, and/or deletion, at one or more (e.g., several) positions and having both a polymerase activity without template and ability to incorporate. The variants may be obtained by various techniques well known in the art. In particular, examples of techniques for altering the DNA sequence encoding the wild-type protein, include, but are not limited to, site-directed mutagenesis, random mutagenesis and synthetic oligonucleotide construction. Mutagenesis activities consists in deleting, inserting or substituting one or several amino-acids in the sequence of the polymerase. Targeted amino-acids could be concomitant or distributed along the whole sequence of the polymerase. Particular motif or structural feature could be targeted for example.

The term "modification" or "alteration" as used herein in relation to a position or amino acid means that the amino acid in the particular position has been modified compared to the amino acid of the wild-type protein.

A "substitution" means that an amino acid residue is replaced by another amino acid residue. Preferably, the term "substitution" refers to the replacement of an amino acid residue by another selected from the naturally-occurring standard 20 amino acid residues, rare naturally occurring amino acid residues (e.g. hydroxyproline, hydroxylysine, allohydroxylysine, 6-N-methylysine, N-ethylglycine, N-methylglycine, N-ethylasparagine, allo-isoleucine, N-methylisoleucine, N-methylvaline, pyroglutamine, aminobutyric acid, ornithine, norleucine, norvaline), and non-naturally occurring amino acid residue, often made synthetically, (e.g. cyclohexyl-alanine). Preferably, the term "substitution" refers to the replacement of an amino acid residue by another selected from the naturally-occurring standard 20 amino acid residues (G, P, A, V, L, I, M, C, F, Y, W, H, K, R, Q, N, E, D, S and T). The sign "+" indicates a combination of substitutions. In the present document, the following terminology is used to designate a substitution: L2382A denotes that amino acid residue (Leucine, L) at position 2382 of the parent sequence is changed to an Alanine (A). A1321V/I/M denotes that amino acid residue (Alanine, A) at position 1321 of the parent sequence is substituted by one of the following amino acids: Valine (V), Isoleucine (I), or Methionine (M). The substitution can be a conservative or non-conservative substitution. Examples of conservative substitutions are within the groups of basic amino acids (arginine, lysine and histidine), acidic amino acids (glutamic acid and aspartic acid), polar amino acids (glutamine, asparagine and threonine), hydrophobic amino acids (methionine, leucine, isoleucine, cysteine and valine), aromatic amino acids (phenylalanine, tryptophan and tyrosine), and small amino acids (glycine, alanine and serine).

The term "deletion", used in relation to an amino acid, means that the amino acid has been removed or is absent.

The term "insertion" means that one or more amino acids have been added.

Unless otherwise specified, the positions disclosed in the present application are numbered by reference to the amino acid sequence set forth in SEQ ID No 1.

As used herein, the term "sequence identity" or "identity" refers to the number (or fraction expressed as a percentage %) of matches (identical amino acid residues) between two polypeptide sequences. The sequence identity is determined by comparing the sequences when aligned so as to maximize overlap and identity while minimizing sequence gaps. In particular, sequence identity may be determined using any of a number of mathematical global or local alignment algorithms, depending on the length of the two sequences. Sequences of similar lengths are preferably aligned using a global alignment algorithms (e.g. Needleman and Wunsch algorithm; Needleman and Wunsch, 1970) which aligns the sequences optimally over the entire length, while sequences of substantially different lengths are preferably aligned using a local alignment algorithm (e.g. Smith and Waterman algorithm (Smith and Waterman, 1981) or Altschul algorithm (Altschul et al., 1997; Altschul et al., 2005)). Alignment for purposes of determining percent amino acid sequence identity can be achieved in various ways that are within the skill in the art, for instance, using publicly available computer software available on internet web sites such as http://blast.ncbi.nlm.nih.gov/ or http://www.ebi.ac.uk/Tools/emboss/). Those skilled in the art can determine appropriate parameters for measuring alignment, including any algorithms needed to achieve maximal alignment over the full length of the sequences being compared. For purposes herein, % amino acid sequence identity values refers to values generated using the pair wise sequence alignment program EMBOSS Needle that creates an optimal global alignment of two sequences using the Needleman-Wunsch algorithm, wherein all search parameters are set to default values, i.e. Scoring matrix=BLOSUM62, Gap open=10, Gap extend=0.5, End gap penalty=false, End gap open=10 and End gap extend=0.5.

Reversible Terminator Modified Nucleotides

In one embodiment, the invention relates to modified Pol θ polymerase able to incorporate modified reversible terminator nucleotides. In a particular embodiment, the invention relates to modified Pol θ polymerases able to incorporate modified 3'O-reversible nucleotides.

In the context of the invention, the expression "Reversible Terminator Modified Nucleotide" refers to a molecule containing a nucleoside (i.e. a base attached to a deoxyribose or ribose sugar molecule) bound to three phosphate groups which has at least one additional group on one of its extremity: 2', 3', 5' or base. Said additional group blocks further addition of nucleotides by preventing the formation of any phosphodiester bond (3'O-modification, 2' or 2'O modifications) or by sterically preventing the polymerase to attached to any nucleic acid fragments that comprises on its 3' extremity such modified reversible terminator nucleotide (5' or base modification). Furthermore, said additional group has a reversible nature allowing that group to be removed through a specific cleaving reaction.

Nucleosides or nucleotide triphosphates include deoxyadenosine triphosphate (dATP), deoxyguanosine triphosphate (dGTP), deoxycytidine triphosphate (dCTP) or deoxythymidine triphosphate (dTTP) for examples of nucleotide containing deoxyribose. Adenosine triphosphate (ATP), guanosine triphosphate (GTP), cytidine triphosphate (CTP) or uridine triphosphate (UTP) are further examples of nucleotide triphosphates containing ribose. Other types of nucleosides may be bound to three phosphates to form nucleotide triphosphates, such as naturally occurring modified nucleosides and artificial nucleosides.

In a particular embodiment, the modified reversible terminator nucleotide is a 3'O modified nucleotide, which comprises a group attached to the 3' end of the nucleotide triphosphate to prevent further nucleotide addition. Said group could have diverse chemical natures, such as azidomethyl, aminoxy, and allyl.

In further particular embodiment, 3'O modified nucleotide refers to nucleotide triphosphate bearing at the 3' extremity either a 3'-O-methyl, 3'-azido, 3'-O-azidomethyl, 3'-O-amino, 3'-aminoxy or 3'-O-allyl group. In a further embodiment, the 3'-blocked nucleotide triphosphate is blocked by either a 3'-O-azidomethyl, 3'-aminoxy or 3'-O-allyl group. In other embodiments, 3'O modified nucleotide refers to nucleotide triphosphate bearing at the 3' extremity either esters, ethers, carbonitriles, phosphates, carbonates, carbamates, hydroxylamine, borates, nitrates, sugars, phosphoramide, phosphoramidates, phenylsulfenates, sulfates, sulfones and amino acids.

In further particular embodiment, 3'O modified nucleotide refers to a nucleotide triphosphate having a terminator effector modifying group such as the ones describe in WO2016034807 incorporated herein by references in its entirety.

According to a first aspect, the invention relates to variants of family A DNA polymerases which exhibit an increased affinity for modified reversible terminator nucleotides, and thereby an increased ability to incorporate such modified nucleotide in a nucleic acid sequence during nucleic acid synthesis, as compared to wild type family A DNA polymerase.

According to a particular aspect, the invention relates to variants of Pol θ polymerases which exhibit an increased affinity for modified reversible terminator nucleotides, and thereby an increased ability to incorporate such modified nucleotide in a nucleic acid sequence during nucleic acid synthesis, as compared to wild type Pol θ polymerase. Particularly, the invention relates to variants of Pol θ polymerases with increased incorporation ability of 3'O-modified nucleotides.

According to another particular aspect, the invention relates to variants of family A DNA polymerases capable of quantitative incorporation of modified reversible terminator nucleotides, more preferably of variants of Pol θ polymerases. Preferably, modified reversible terminator nucleotides are 3'O-modified nucleotides.

According to another aspect, the invention relates to variants of Family A DNA Polymerase able to work with reversible terminator modified nucleotides in a nucleic acids enzymatic synthesis process, and having the ability to produce long length of nucleic acid molecules or derivative of nucleic acids molecules; in particular embodiments, of Pol θ polymerases; in further particular embodiments, of 3'-modified nucleotides.

Depending on the mutation or the combination of mutations, the polymerase will display improved ability to incorporate 3'O modified nucleotides to a growing single stranded chain of nucleic acids. Such improved property finds use in the de novo synthesis of nucleic acids.

Variants of Family A DNA Polymerase

According to the invention, the variants of Family A DNA Polymerase are capable of synthesizing extremely long fragments of nucleic acid molecules before dissociation. Extremely long fragments of nucleic acid molecule having length of more than 50, 100, 200, 300, 400, 500, 600, 700, 800, 900, 1 000, 2 000, 3 000, 4 000, 5 000, 6 000, 7 000, 8 000, 9 000, 10 000, 15 000, 20 000, 30 000, 40 000, 50 000 or 100 000 nucleotides.

It is known that A Family polymerases could be composed by several distinct domains. Pol θ polymerases possesses 3 different domains: helicase domain, central domain and polymerase domain (see table 1 below). The helicase domain has an enzymatic activity related to helicase activity, an ATP consumption activity and nucleic acid strand affinity. The central domain seams to lake of particular specific enzymatic activity. The polymerase domain possesses an enzymatic activity related to nucleotide polymerization and nucleic acid strand affinity.

In a particular embodiment, the present invention contemplates modified Pol θ polymerases baring any mutation or combination previously described applicate to the whole enzyme composed of the three domains: helicase, central and polymerase domain.

In an alternative embodiment, the present invention contemplates modified Pol θ polymerases baring any mutation or combination previously described applicate to the following subdomains: helicase and polymerase domain. In particular, the helicase and polymerase domain could be separated by any amino acid linker, including non-natural amino acids, of any length between 1 and 1000 amino acids. Said linker could be composed in its N-terminal and C-terminal extremity by part or full central domain sequence linked respectively to the helicase and polymerase domains.

Preferably, the variant of the invention comprises at least the amino acid sequence as set forth in SEQ ID No 2, except at least one mutation of an amino acid.

SEQ ID No 2 corresponds to the amino acid residues 2327 to 2339 of SEQ ID No 1, which is the amino acid sequence of the human Pol θ (Pol Theta). Pol θ comprises several domains, as listed in table 1 below, wherein the amino acid positions are numbered by reference to the amino acid sequence set forth in SEQ ID No 1.

TABLE 1

Pol Theta Domains

| Pol Theta Domains | Amino acid positions |
|---|---|
| Helicase domain | 1 to 899 |
| Central domain | 900 to 1818 |
| Polymerase domain | 1819 to 2590 |
| Insert 1 | 2149 to 2170 |
| Insert 2 | 2263 to 2314 |
| Insert 3 | 2496 to 2530 |

According to the invention, the variant (i) comprises the amino acid sequence set forth in SEQ ID No 2 or a functionally equivalent sequence, with at least one amino acid mutation at any one of the amino acid residue as compared to SEQ ID No 2, (ii) is able to synthesize a nucleic acid fragment without template and (iii) is able to incorporate a reversible modified terminator nucleotide during the nucleic acid fragment synthesis.

The variants of the present invention are described according to their mutations on specific residues whose positions are determined by alignment with or reference to the enzymatic sequence SEQ ID No 1, which corresponds to the amino acid sequence of the human Pol θ. In the context of the invention, any variant bearing these same mutations on functionally equivalent residues is also part of the invention.

By "functionally equivalent residue" is meant a residue in a sequence of a DNA polymerase of Pol θ of sequence homologous to SEQ ID No 1 and having an identical functional role.

Functionally equivalent residues are identified by using sequence alignments, for example, using the Mutalin line alignment software (http://multalin.toulouse.inra.fr/multalin/multalin.html; 1988, Nucl. Acids Res., 16 (22), 10881-10890). After alignment, the functionally equivalent residues are at homologous positions on the different sequences considered. Sequence alignments and identification of functionally equivalent residues may be between any of the polymerases of the Polymerase A family, and preferably any Pol θ and their natural variants, including inter-species.

In the context of the invention, "functional fragment" refers to a DNA polymerase fragment of Family A exhibiting DNA polymerase activity. The fragment may comprise 500, 600, 700 or more consecutive amino acids of a polymerase of Family A. Preferably, the fragment comprises at least 770 consecutive amino acids of the polymerase domain of said enzyme. "Functional equivalent sequence" refers to a sequence homologous to the disclosed sequence and having an identical functional role.

SEQ ID No 3

In a particular embodiment, the variant comprises at least a mutated amino acid in the amino acid sequence as set forth in SEQ ID No 3 (DYSQLELRIL), or functional equivalent sequence, in a homologous Pol θ sequence.

SEQ ID No 3 constitutes a succession of amino acids in direct interaction with the incoming nucleotide, in particular with the 3' and 2' extremity of the sugar moiety of the nucleotide. The amino acid residues of SEQ ID No 3 are especially close to the 3' and 2' extremity of the sugar moiety of the nucleotide and are well conserved across different species. Side chains of amino acid residues of SEQ ID No 3 form a steric gate for nucleotide having a bulkier size than natural nucleotides.

In a particular embodiment, the variant comprises one or more substitutions of amino acid residues of SEQ ID No 3. Such residues are adjacent (i.e. successive) or distributed across SEQ ID No 3. Such substitutions are identical or different across the targeted residues.

In a particular embodiment, the variant comprises one or more deletions of amino acid residues of SEQ ID No 3. Such residues are adjacent (i.e. successive) or distributed across SEQ ID No 3.

In a particular embodiment, the variant comprises one or more additions of amino acid residues in one or more locations of SEQ ID No 3. Such locations are adjacent (i.e. successive) or distributed across SEQ ID No 3.

In a particular embodiment, the substitution is selected from the substitutions listed in table 2 below.

TABLE 2

Preferred substitutions in SEQ ID No 3

| Natural Amino Acid | Residue Position | Substitution |
|---|---|---|
| D | 2330 | E; R; H; K; T; V; A; G |
| Y | 2331 | F; W; P; H; M; L; V; A |
| S | 2332 | T; N; Q; V; A; G |
| Q | 2333 | N; T; S; A; G; V |
| L | 2334 | M; E; N; F; K; D; A; G |
| E | 2335 | G; A; N; T; S; D |
| L | 2336 | M; E; N; F; K; D; A; G |
| R | 2337 | H; K; D; E; A; G; M; F |
| I | 2338 | V; A; G; L; T; S; D; K; M |
| L | 2339 | M; E; N; F; K; D; A; G; I |

SEQ ID No 4

In a particular embodiment, the variant comprises at least a mutated amino acid in the amino acid sequence as set forth in SEQ ID No 4 (PGGSILAA), or functional equivalent sequence, in a homologous Pol θ sequence.

SEQ ID No 4 constitutes a structural feature orienting the β-sheet strands of the palm domain of the polymerase. The palm domain of the polymerase is closely interacting with the incoming nucleotide. Altering Motif B sequence will have an influence on palm conformation and lead to a wider catalytic pocket for accepting bulkier nucleotides. Introducing more flexibility or new strand orientation by altering SEQ ID No 4 will change palm domain capacity to accept different size of nucleotides.

In a particular embodiment, the variant comprises one or more substitutions of amino acid residues of SEQ ID No 4. Such residues are adjacent (i.e. successive) or distributed across SEQ ID No 4. Such substitutions are identical or different across the targeted residues.

In a particular embodiment, the variant comprises one or more deletions of amino acid residues of SEQ ID No 4. Such residues are adjacent (i.e. successive) or distributed across SEQ ID No 4.

In a particular embodiment, the variant comprises one or more additions of amino acid residues in one or more locations of SEQ ID No 4. Such locations are adjacent (i.e. successive) or distributed across SEQ ID No 4.

In a particular embodiment, the substitution is selected from the substitutions listed in table 3 below.

TABLE 3

Preferred substitutions in SEQ ID No 4

| Natural Amino Acid | Residue Position | Substitution |
|---|---|---|
| P | 2322 | A; V; I; L; G; C |
| G | 2323 | C; P; A; V; K; D |
| G | 2324 | C; P; A; V; K; D |
| S | 2325 | L; N; M; V; T; A; G; D; K |
| I | 2326 | V; A; G; L; T; S; D; K; M |
| L | 2327 | M; E; N; F; K; D; A; G; I; V |
| A | 2328 | V; T; G |
| A | 2329 | V; T; G |

SEQ ID No 5

In a particular embodiment, the variant comprises at least a mutated amino acid in the amino acid sequence as set forth in SEQ ID No 5 (DDLRQQAKQICYGIIY), or functional equivalent sequence, in a homologous Pol θ sequence, excluding the following substitution mutation: Q2384A.

SEQ ID No 5 constitutes a succession of amino acids in direct interaction with the pyrophosphate moiety of the incoming nucleotide. It has been shown, that altering the natural interaction between the enzyme residues and the pyrophosphate moiety of the nucleotide leads to modification of the nucleotide orientation while conserving the catalytic efficiency of the polymerase enzyme. The result of such alteration is thus a modified polymerase able to add a nucleotide or modified nucleotide in a different orientation, compared to natural orientation of the nucleotide in the wild type enzyme, with same or improved efficiency. The difference in nucleotide orientation can be significantly advantageous for accommodating bulkier nucleotides or nucleotide with a particular modification at a specific extremity such as 3'O-modified nucleotides for example. The Y2391 residue interacts with both 3' and 2' extremity of the sugar moiety of the nucleotide. Altering Y2391 will lead to modification of the space allocated for the nucleotide in the catalytic pocket, especially in the local 3' and 2' extremity of the nucleotide. In particular bulkier 3' or 2' modifying groups bared by modified nucleotides could be process by enzyme having an altered Y2391.

In a particular embodiment, the variant comprises one or more substitutions of amino acid residues of SEQ ID No 5. Such residues are adjacent (i.e. successive) or distributed across SEQ ID No 5. Such substitutions are identical or different across the targeted residues.

In a particular embodiment, the variant comprises one or more deletions of amino acid residues of SEQ ID No 5. Such residues are adjacent (i.e. successive) or distributed across SEQ ID No 5.

In a particular embodiment, the variant comprises one or more additions of amino acid residues in one or more locations of SEQ ID No 5. Such locations are adjacent (i.e. successive) or distributed across SEQ ID No 5.

In particular embodiments, the substitution is selected from the substitutions listed in table 4 below.

TABLE 4

Preferred substitutions in SEQ ID No 5

| Natural Amino Acid | Residue Position | Substitution | Excluded Substitution |
|---|---|---|---|
| D | 2376 | E; R; H; K; T; V; A; G; N | |
| D | 2377 | E; R; H; K; T; V; A; G; N | |
| L | 2378 | M; E; N; F; K; D; A; G; I | |
| R | 2379 | H; K; D; E; A; G; M; F | |
| Q | 2380 | N; T; S; A; G; V | |
| Q | 2381 | N; T; S; A; G; V | |
| A | 2382 | V; T; G | |
| K | 2383 | R; H; D; E; Q; N; C; A; G; S; T | |
| Q | 2384 | N; T; S; G; V | A |
| I | 2385 | V; A; G; L; T; S; D; K; M | |
| C | 2386 | G; P; A; V; S; N; Q; D; K | |
| Y | 2387 | F; W; P; H; M; L; V; A | |
| G | 2388 | C; P; A; V; K; D | |
| I | 2389 | V; A; G; L ;T; S; D; K; M | |
| I | 2390 | V; A; G; L; T; S; D; K; M | |
| Y | 2391 | F; W; P; H; M; L; V; A | |

SEQ ID No 6

In a particular embodiment, the variant comprises at least a mutated amino acid in the amino acid sequence as set forth in SEQ ID No 6 (EWRRIT), or functional equivalent sequence, in a homologous Pol θ sequence excluding the following substitution mutation: R2202A.

SEQ ID No 6 constitutes a succession of amino acids in direct interaction with the different residues that constitute the nucleic acid growing chain. Altering the amino acids of SEQ ID No 6 leads to changes in primer orientation that enable increase of the catalytic pocket volume globally or locally. Such changes in catalytic pocket volume could have an impact on enzyme capacity to accept bulkier nucleotide or nucleotide with a particular modification. Modifying the interaction with the nucleic acid growing chain also leads to modification of the affinity of the enzyme for the primer strand. Such affinity modification impacts enzyme/nucleic acid dissociation characteristics including, but not limited to, dissociation strength and dissociation characteristic time. As a result, altering residues of SEQ ID No 6 changes enzyme affinity for different type of nucleic acid molecules having different structures, such as DNA, RNA, DNA with epigenetic modifications, RNA with epigenetic modifications or XNA as examples.

In a particular embodiment, the variant comprises one or more substitutions of amino acid residues of SEQ ID No 6. Such residues are adjacent (i.e. successive) or distributed across SEQ ID No 6. Such substitutions are identical or different across the targeted residues.

In a particular embodiment, the variant comprises one or more deletions of amino acid residues of SEQ ID No 6. Such residues are adjacent (i.e. successive) or distributed across SEQ ID No 6.

In a particular embodiment, the variant comprises one or more additions of amino acid residues in one or more locations of SEQ ID No 6. Such locations are adjacent (i.e. successive) or distributed across SEQ ID No 6.

In particular embodiments, the substitution is selected from the substitutions listed in table 5 below.

TABLE 5

Preferred substitutions in SEQ ID No 6

| Natural Amino Acid | Residue Position | Substitution | Excluded Substitution |
|---|---|---|---|
| E | 2199 | G; A; N; T; S; D; K | |
| W | 2200 | Y; F; P; L; I; V; A; G; E | |
| R | 2201 | H; K; D; E; G; M; F; S; P | |
| R | 2202 | H; K; D; E; G; M; F; S; P | A |
| I | 2203 | V; A; G; L; T; S; D; K; M; P | |
| T | 2204 | S; N; Q; C; G; M; K; D | |

Catalytic Triad

In a particular embodiment, the variant comprises at least one amino acid mutation, preferably of at least two mutations, more preferably three mutation at position(s) corresponding to residues selected from D2330, D2540 or E2541, or residues functionally equivalent, excluding D2540N/A or E2541Q/A, wherein the positions are numbered by reference to the amino acid sequence set forth in SEQ ID No 1.

The catalytic triad residues are the residues directly involved in the phosphodiester condensation reaction performed by the polymerases. Altering those residues modifies the overall activity of the polymerase enzyme. Alteration of one or more of the catalytic triad residues in association with the use of modified nucleotide advantageously lead to increased incorporation rate of said modified nucleotide due to conformational adaptations sufficient to deal with nucleotide modifications. Some specific substitutions such as D2540N, D2540A, E2541Q or E2541A, alone or in combination are known to suppress the activity of the polymerase. As a result, these substitutions are excluded from the scope of the present invention.

In a particular embodiment, the variant comprises one or more substitutions of amino acid residues selected from D2330, D2540 or E2541. Such substitutions are identical or different across the targeted residues. In a preferred embodiment, the variant comprises a substitution at the amino acid position D2330, D2540 and E2541.

In a particular embodiment, the variant comprises one or more deletions of amino acid residues comprises one or more substitutions of amino acid residues selected from D2330, D2540 or E2541.

In a particular embodiment, the variant comprises one or more additions of amino acid residues before or after one or more of amino acid residues selected from D2330, D2540 or E2541.

In particular embodiments, the substitutions are selected from table 6

TABLE 6

Preferred substitutions in the catalytic triad

| Natural Amino Acid | Residue Position | Substitution | Excluded Substitution |
|---|---|---|---|
| D | 2330 | E; R; H; K; T; V; A; G | |
| D | 2540 | E; K; R; H; Q; S; T; C | N; A |
| E | 2541 | D; R; H; K; N; S; T; C | Q; A |

Other Residues of Interest

In an embodiment of the invention, the variant comprises at least a mutation in one of the following residues composed by K2181, R2315, F2359, or A2477, or a functional equivalent of those residues in a homologous Pol θ sequence; excluding the following substitution mutation: K2181A and the following residue deletion: Δ2315.

The K2181 residue interacts with the nucleic acid growing chain. Effect of alteration of this residue is similar to alteration in residues of SEQ ID No 6. The substitution K2181A alone or in combination is known to reduce the activity of the polymerase. The F2315 residue interacts with the ultimate nucleotide of the nucleic acid growing chain. Effect of alteration of this residue is similar to alteration in residues of SEQ ID No 6. The deletion of R2315 residue alone or in combination is known to reduce the activity of the polymerase. The F2359 residue acts as a satirical gate for nucleotide to enter the catalytic pocket. Altering F2359 leads to modification of the association characteristics between the enzyme and the nucleotide. In particular wider space for modified nucleotide to enter could be obtained by altering F2359. The A2477 residue is implicated in the overall size of the catalytic pocket. Altering A2477 leads to modification of the space allocated for the nucleotide in the catalytic pocket. In particular bulkier modified nucleotides could be processed by enzyme having an altered A2477.

In a particular embodiment, the variant comprises one or more substitutions of amino acid residues selected from K2181, R2315, F2359, or A2477. Such substitutions are identical or different across the targeted residues. In a preferred embodiment, the variant comprises substitutions at all the amino acid positions K2181, R2315, F2359, and A2477.

In a particular embodiment, the variant comprises one or more deletions of amino acid residues comprises one or more substitutions of amino acid residues selected from K2181, R2315, F2359, or A2477.

In a particular embodiment, the variant comprises one or more additions of amino acid residues before or after one or more of amino acid residues selected from K2181, R2315, F2359, or A2477.

In particular embodiments, the substitutions are selected from the table 7.

TABLE 7

Preferred substitutions

| Natural Amino Acid | Residue Position | Substitution | Excluded Substitution |
|---|---|---|---|
| K | 2181 | R; H; D; E; Q; N; C; G; S; T | A |
| R | 2315 | H; K; D; E; A; G; M; F | |
| F | 2359 | M; L; I; V; A; G; P; T; K; D | |
| A | 2477 | V; T; G | |

Steric Enlargement of Catalytic Pocket

Structural 3D models of Family A polymerases provide useful information about nucleotide conformation, catalytic pocket size and steric hindrance of side chains of specific residues. Identification of residues based on their special configuration and interactions with the nucleotide present inside the catalytic pocket is critical.

In a particular embodiment of the invention, the variant comprises at least one amino acid mutation of a residue having side chain groups positioned within 15 Å, 12 Å, 10 Å, or 6 Å of a 3'O extremity of a nucleotide, or residue functionally equivalent.

In a particular embodiment, the present invention contemplates modified Pol θ polymerases in one or several of the residues within 0.6 nm (6 Å) of the 3'O extremity of the nucleotide.

In a particular embodiment, the present invention contemplates modified Pol θ polymerases in one or several of the residues within 1.0 nm (10 Å) of the 3'O extremity of the nucleotide.

In a particular embodiment, the present invention contemplates modified Pol θ polymerases in one or several of the residues within 1.2 nm (12 Å) of the 3'O extremity of the nucleotide.

In a particular embodiment, the present invention contemplates modified Pol θ polymerases in one or several of the residues within 1.5 nm (15 Å) of the 3'O extremity of the nucleotide.

More particularly, according to a particular embodiment, the present invention contemplates modified Pol θ polymerases in one or several of the residues listed in table 8 below.

TABLE 8

Residue positions at 6, 10, 10, and 15 Å

| Residue | Position | Distance (Å) |
| --- | --- | --- |
| Q | 2333 | 6 |
| E | 2335 | 6 |
| Y | 2387 | 6 |
| D | 2540 | 6 |
| R | 2241 | 10 |
| D | 2330 | 10 |
| Y | 2331 | 10 |
| S | 2332 | 10 |
| L | 2334 | 10 |
| L | 2336 | 10 |
| R | 2337 | 10 |
| I | 2338 | 10 |
| F | 2359 | 10 |
| Q | 2380 | 10 |
| K | 2383 | 10 |
| G | 2388 | 10 |
| I | 2390 | 10 |
| Y | 2391 | 10 |
| V | 2473 | 10 |
| Q | 2474 | 10 |
| A | 2477 | 10 |
| A | 2478 | 10 |
| V | 2481 | 10 |
| H | 2539 | 10 |
| T | 2239 | 12 |
| R | 2254 | 12 |
| L | 2339 | 12 |
| L | 2352 | 12 |
| D | 2357 | 12 |
| R | 2379 | 12 |
| Q | 2384 | 12 |
| C | 2386 | 12 |
| I | 2469 | 12 |
| N | 2470 | 12 |
| G | 2475 | 12 |
| S | 2476 | 12 |
| I | 2480 | 12 |
| Q | 2537 | 12 |
| L | 2538 | 12 |
| E | 2541 | 12 |
| M | 2562 | 12 |
| L | 2572 | 12 |
| K | 2575 | 12 |
| T | 2237 | 15 |
| G | 2240 | 15 |
| I | 2242 | 15 |
| T | 2243 | 15 |
| Q | 2250 | 15 |
| R | 2315 | 15 |
| A | 2329 | 15 |
| A | 2340 | 15 |
| H | 2341 | 15 |
| L | 2342 | 15 |
| L | 2348 | 15 |

TABLE 8-continued

Residue positions at 6, 10, 10, and 15 Å

| Residue | Position | Distance (Å) |
| --- | --- | --- |
| G | 2355 | 15 |
| V | 2358 | 15 |
| I | 2362 | 15 |
| Q | 2381 | 15 |
| A | 2382 | 15 |
| I | 2385 | 15 |
| I | 2389 | 15 |
| G | 2392 | 15 |
| M | 2393 | 15 |
| Q | 2401 | 15 |
| I | 2423 | 15 |
| F | 2426 | 15 |
| M | 2427 | 15 |
| T | 2442 | 15 |
| I | 2443 | 15 |
| R | 2446 | 15 |
| T | 2471 | 15 |
| I | 2472 | 15 |
| D | 2479 | 15 |
| A | 2484 | 15 |
| L | 2536 | 15 |
| L | 2542 | 15 |
| L | 2568 | 15 |
| V | 2570 | 15 |
| K | 2573 | 15 |
| V | 2574 | 15 |
| K | 2577 | 15 |
| W | 2582 | 15 |

Mutations and Combination of Mutations

The present invention relates to modified Pol θ polymerases with increased incorporation rate for reversible terminator modified nucleotides. It will be understood that the present invention contemplates any combinations of mutations listed below. In particular combination of two or more substitutions, combination of one or more substitution with residue deletion or addition or both, combination of two or more deletion, combination of deletion and addition, and combination of two of more additions.

It is therefore an object of the invention to provide variants of Pol Theta, which comprise at least a substitution or combination of substitutions as listed in table 9, wherein the positions are numbered by reference to the amino acid sequence set forth in SEQ ID No 1.

TABLE 9

Mutations and combination of substitutions

| Name | Mutations |
| --- | --- |
| DS1 | L2336A + A2328V + Y2387F + E2335G + P2322A + L2334M |
| DS2 | L2336A + A2328V + Y2387F + E2335G + P2322A + L2334G |
| DS3 | L2336A + A2328V + Y2387F + E2335G + P2322A |
| DS4 | L2336A + A2328V + Y2387F + E2335G + P2322V + L2334M |
| DS5 | L2336A + A2328V + Y2387F + E2335G + P2322V + L2334G |
| DS6 | L2336A + A2328V + Y2387F + E2335G + P2322V |
| DS7 | L2336A + A2328V + Y2387F + E2335G + L2334M |
| DS8 | L2336A + A2328V + Y2387F + E2335G + L2334G |
| DS9 | L2336A + A2328V + Y2387F + E2335G |
| DS10 | L2336A + A2328V + Y2387F + E2335A + P2322A + L2334M |
| DS11 | L2336A + A2328V + Y2387F + E2335A + P2322A + L2334G |

TABLE 9-continued

Mutations and combination of substitutions

| Name | Mutations |
|---|---|
| DS12 | L2336A + A2328V + Y2387F + E2335A + P2322A |
| DS13 | L2336A + A2328V + Y2387F + E2335A + P2322V + L2334M |
| DS14 | L2336A + A2328V + Y2387F + E2335A + P2322V + L2334G |
| DS15 | L2336A + A2328V + Y2387F + E2335A + P2322V |
| DS16 | L2336A + A2328V + Y2387F + E2335A + L2334M |
| DS17 | L2336A + A2328V + Y2387F + E2335A + L2334G |
| DS18 | L2336A + A2328V + Y2387F + E2335A |
| DS19 | L2336A + A2328V + Y2387F + P2322A + L2334M |
| DS20 | L2336A + A2328V + Y2387F + P2322A + L2334G |
| DS21 | L2336A + A2328V + Y2387F + P2322A |
| DS22 | L2336A + A2328V + Y2387F + P2322V + L2334M |
| DS23 | L2336A + A2328V + Y2387F + P2322V + L2334G |
| DS24 | L2336A + A2328V + Y2387F + P2322V |
| DS25 | L2336A + A2328V + Y2387F + L2334M |
| DS26 | L2336A + A2328V + Y2387F + L2334G |
| DS27 | L2336A + A2328V + Y2387F |
| DS28 | L2336A + A2328V + E2335G + P2322A + L2334M |
| DS29 | L2336A + A2328V + E2335G + P2322A + L2334G |
| DS30 | L2336A + A2328V + E2335G + P2322A |
| DS31 | L2336A + A2328V + E2335G + P2322V + L2334M |
| DS32 | L2336A + A2328V + E2335G + P2322V + L2334G |
| DS33 | L2336A + A2328V + E2335G + P2322V |
| DS34 | L2336A + A2328V + E2335G + L2334M |
| DS35 | L2336A + A2328V + E2335G + L2334G |
| DS36 | L2336A + A2328V + E2335G |
| DS37 | L2336A + A2328V + E2335A + P2322A + L2334M |
| DS38 | L2336A + A2328V + E2335A + P2322A + L2334G |
| DS39 | L2336A + A2328V + E2335A + P2322A |
| DS40 | L2336A + A2328V + E2335A + P2322V + L2334M |
| DS41 | L2336A + A2328V + E2335A + P2322V + L2334G |
| DS42 | L2336A + A2328V + E2335A + P2322V |
| DS43 | L2336A + A2328V + E2335A + L2334M |
| DS44 | L2336A + A2328V + E2335A + L2334G |
| DS45 | L2336A + A2328V + E2335A |
| DS46 | L2336A + A2328V + P2322A + L2334M |
| DS47 | L2336A + A2328V + P2322A + L2334G |
| DS48 | L2336A + A2328V + P2322A |
| DS49 | L2336A + A2328V + P2322V + L2334M |
| DS50 | L2336A + A2328V + P2322V + L2334G |
| DS51 | L2336A + A2328V + P2322V |
| DS52 | L2336A + A2328V + L2334M |
| DS53 | L2336A + A2328V + L2334G |
| DS54 | L2336A + A2328V |
| DS55 | L2336A + Y2387F + E2335G + P2322A + L2334M |
| DS56 | L2336A + Y2387F + E2335G + P2322A + L2334G |
| DS57 | L2336A + Y2387F + E2335G + P2322A |
| DS58 | L2336A + Y2387F + E2335G + P2322V + L2334M |
| DS59 | L2336A + Y2387F + E2335G + P2322V + L2334G |
| DS60 | L2336A + Y2387F + E2335G + P2322V |
| DS61 | L2336A + Y2387F + E2335G + L2334M |
| DS62 | L2336A + Y2387F + E2335G + L2334G |
| DS63 | L2336A + Y2387F + E2335G |
| DS64 | L2336A + Y2387F + E2335A + P2322A + L2334M |
| DS65 | L2336A + Y2387F + E2335A + P2322A + L2334G |
| DS66 | L2336A + Y2387F + E2335A + P2322A |
| DS67 | L2336A + Y2387F + E2335A + P2322V + L2334M |
| DS68 | L2336A + Y2387F + E2335A + P2322V + L2334G |
| DS69 | L2336A + Y2387F + E2335A + P2322V |
| DS70 | L2336A + Y2387F + E2335A + L2334M |
| DS71 | L2336A + Y2387F + E2335A + L2334G |
| DS72 | L2336A + Y2387F + E2335A |
| DS73 | L2336A + Y2387F + P2322A + L2334M |
| DS74 | L2336A + Y2387F + P2322A + L2334G |
| DS75 | L2336A + Y2387F + P2322A |
| DS76 | L2336A + Y2387F + P2322V + L2334M |
| DS77 | L2336A + Y2387F + P2322V + L2334G |
| DS78 | L2336A + Y2387F + P2322V |
| DS79 | L2336A + Y2387F + L2334M |
| DS80 | L2336A + Y2387F + L2334G |
| DS81 | L2336A + Y2387F |
| DS82 | L2336A + E2335G + P2322A + L2334M |
| DS83 | L2336A + E2335G + P2322A + L2334G |
| DS84 | L2336A + E2335G + P2322A |
| DS85 | L2336A + E2335G + P2322V + L2334M |
| DS86 | L2336A + E2335G + P2322V + L2334G |
| DS87 | L2336A + E2335G + P2322V |
| DS88 | L2336A + E2335G + L2334M |
| DS89 | L2336A + E2335G + L2334G |
| DS90 | L2336A + E2335G |
| DS91 | L2336A + E2335A + P2322A + L2334M |
| DS92 | L2336A + E2335A + P2322A + L2334G |
| DS93 | L2336A + E2335A + P2322A |
| DS94 | L2336A + E2335A + P2322V + L2334M |
| DS95 | L2336A + E2335A + P2322V + L2334G |
| DS96 | L2336A + E2335A + P2322V |
| DS97 | L2336A + E2335A + L2334M |
| DS98 | L2336A + E2335A + L2334G |
| DS99 | L2336A + E2335A |
| DS100 | L2336A + P2322A + L2334M |
| DS101 | L2336A + P2322A + L2334G |
| DS102 | L2336A + P2322A |
| DS103 | L2336A + P2322V + L2334M |
| DS104 | L2336A + P2322V + L2334G |
| DS105 | L2336A + P2322V |
| DS106 | L2336A + L2334M |
| DS107 | L2336A + L2334G |
| DS108 | L2336A |
| DS109 | A2328V + Y2387F + E2335G + P2322A + L2334M |
| DS110 | A2328V + Y2387F + E2335G + P2322A + L2334G |
| DS111 | A2328V + Y2387F + E2335G + P2322A |
| DS112 | A2328V + Y2387F + E2335G + P2322V + L2334M |
| DS113 | A2328V + Y2387F + E2335G + P2322V + L2334G |
| DS114 | A2328V + Y2387F + E2335G + P2322V |
| DS115 | A2328V + Y2387F + E2335G + L2334M |
| DS116 | A2328V + Y2387F + E2335G + L2334G |
| DS117 | A2328V + Y2387F + E2335G |
| DS118 | A2328V + Y2387F + E2335A + P2322A + L2334M |
| DS119 | A2328V + Y2387F + E2335A + P2322A + L2334G |
| DS120 | A2328V + Y2387F + E2335A + P2322A |
| DS121 | A2328V + Y2387F + E2335A + P2322V + L2334M |
| DS122 | A2328V + Y2387F + E2335A + P2322V + L2334G |
| DS123 | A2328V + Y2387F + E2335A + P2322V |
| DS124 | A2328V + Y2387F + E2335A + L2334M |
| DS125 | A2328V + Y2387F + E2335A + L2334G |
| DS126 | A2328V + Y2387F + E2335A |
| DS127 | A2328V + Y2387F + P2322A + L2334M |
| DS128 | A2328V + Y2387F + P2322A + L2334G |
| DS129 | A2328V + Y2387F + P2322A |
| DS130 | A2328V + Y2387F + P2322V + L2334M |
| DS131 | A2328V + Y2387F + P2322V + L2334G |
| DS132 | A2328V + Y2387F + P2322V |
| DS133 | A2328V + Y2387F + L2334M |
| DS134 | A2328V + Y2387F + L2334G |
| DS135 | A2328V + Y2387F |
| DS136 | A2328V + E2335G + P2322A + L2334M |
| DS137 | A2328V + E2335G + P2322A + L2334G |
| DS138 | A2328V + E2335G + P2322A |
| DS139 | A2328V + E2335G + P2322V + L2334M |
| DS140 | A2328V + E2335G + P2322V + L2334G |
| DS141 | A2328V + E2335G + P2322V |
| DS142 | A2328V + E2335G + L2334M |
| DS143 | A2328V + E2335G + L2334G |
| DS144 | A2328V + E2335G |
| DS145 | A2328V + E2335A + P2322A + L2334M |
| DS146 | A2328V + E2335A + P2322A + L2334G |
| DS147 | A2328V + E2335A + P2322A |
| DS148 | A2328V + E2335A + P2322V + L2334M |
| DS149 | A2328V + E2335A + P2322V + L2334G |
| DS150 | A2328V + E2335A + P2322V |
| DS151 | A2328V + E2335A + L2334M |
| DS152 | A2328V + E2335A + L2334G |
| DS153 | A2328V + E2335A |
| DS154 | A2328V + P2322A + L2334M |
| DS155 | A2328V + P2322A + L2334G |
| DS156 | A2328V + P2322A |
| DS157 | A2328V + P2322V + L2334M |
| DS158 | A2328V + P2322V + L2334G |
| DS159 | A2328V + P2322V |
| DS160 | A2328V + L2334M |
| DS161 | A2328V − L2334G |

TABLE 9-continued

Mutations and combination of substitutions

| Name | Mutations |
|---|---|
| DS162 | A2328V |
| DS163 | Y2387F + E2335G + P2322A + L2334M |
| DS164 | Y2387F + E2335G + P2322A + L2334G |
| DS165 | Y2387F + E2335G + P2322A |
| DS166 | Y2387F + E2335G + P2322V + L2334M |
| DS167 | Y2387F + E2335G + P2322V + L2334G |
| DS168 | Y2387F + E2335G + P2322V |
| DS169 | Y2387F + E2335G + L2334M |
| DS170 | Y2387F + E2335G + L2334G |
| DS171 | Y2387F + E2335G |
| DS172 | Y2387F + E2335A + P2322A + L2334M |
| DS173 | Y2387F + E2335A + P2322A + L2334G |
| DS174 | Y2387F + E2335A + P2322A |
| DS175 | Y2387F + E2335A + P2322V + L2334M |
| DS176 | Y2387F + E2335A + P2322V + L2334G |
| DS177 | Y2387F + E2335A + P2322V |
| DS178 | Y2387F + E2335A + L2334M |
| DS179 | Y2387F + E2335A + L2334G |
| DS180 | Y2387F + E2335A |
| DS181 | Y2387F + P2322A + L2334M |
| DS182 | Y2387F + P2322A + L2334G |
| DS183 | Y2387F + P2322A |
| DS184 | Y2387F + P2322V + L2334M |
| DS185 | Y2387F + P2322V + L2334G |
| DS186 | Y2387F + P2322V |
| DS187 | Y2387F + L2334M |
| DS188 | Y2387F + L2334G |
| DS189 | Y2387F |
| DS190 | E2335G + P2322A + L2334M |
| DS191 | E2335G + P2322A + L2334G |
| DS192 | E2335G + P2322A |
| DS193 | E2335G + P2322V + L2334M |
| DS194 | E2335G + P2322V + L2334G |
| DS195 | E2335G + P2322V |
| DS196 | E2335G + L2334M |
| DS197 | E2335G + L2334G |
| DS198 | E2335G |
| DS199 | E2335A + P2322A + L2334M |
| DS200 | E2335A + P2322A + L2334G |
| DS201 | E2335A + P2322A |
| DS202 | E2335A + P2322V + L2334M |
| DS203 | E2335A + P2322V + L2334G |
| DS204 | E2335A + P2322V |
| DS205 | E2335A + L2334M |
| DS206 | E2335A + L2334G |
| DS207 | E2335A |
| DS208 | P2322A + L2334M |
| DS209 | P2322A + L2334G |
| DS210 | P2322A |
| DS211 | P2322V + L2334M |
| DS212 | P2322V + L2334G |
| DS213 | P2322V |
| DS214 | L2334M |
| DS215 | L2334G |

Additional Modifications

In an embodiment, the variant is a variant of Pol θ comprising a modified polymerase domain as described above, which is further preceded in its N-terminal sequence by part or full central domain sequence.

In a further embodiment, the variant comprises the Pol θ polymerase sequence or any of the previously described functional fragments with any one of the mutation or combination of mutations described above, which further includes any type of tagging peptide in its N-terminal, C-terminal or both extremity. Said tagging peptide could be used for purification, identification, increasing expression, secretability or increasing catalytic activity. It will be understood that such different tags are extensively described in the literature and thus all tag known to a skilled person are covered by the present invention.

The variants of the invention can also include one or more exogenous or heterologous features at the N- and/or C-terminal regions of the protein for use, e.g., in the purification of the recombinant polymerase. The polymerases can also include one or more deletions (including domain deletions) that facilitate purification of the protein, e.g., by increasing the solubility of recombinantly produced protein. For e.g., the polypeptide fragment from amino acid position 1792 to 2590 of SEQ ID No 1 has been identified as the shortest active fragment (SEQ ID No 2) of the wild-type DNA polymerase Pol θ. (J. Mol. Biol. (2011) 405, 642-652)

Conversion of Other Family A Polymerases

As previously described Pol θ polymerases possess a polymerase activity even in absence of any template. When Pol θ polymerase domain sequence is aligned to other polymerase domains across the entire polymerase A Family, it appears that specific insertions are present in Pol θ polymerase domain. Deletion of a particular insert known as insert 2 (see table 1) is suppressing the ability of Pol θ to elongate nucleic acid fragment in absence of template.

In a particular embodiment, the present invention contemplates modified Family A polymerases according to the present invention, that are further modified by adding any insert 2 of a Pol θ polymerase in their polymerase domain.

In a further embodiment, the present invention contemplates modified Family A polymerases comprising any functionally equivalent mutations or combination previously described in its polymerase domain, said polymerases would be further modified by adding any insert 2 of a Pol θ polymerase in their polymerase domain.

Alternative Pol θ Polymerases

Human Pol θ polymerase sequence is given by SEQ ID No 1. Pol θ polymerases could be found in many other organisms or microorganisms. All those Pol θ polymerases are good candidate for performing the present invention. In particular, modifications to alter a particular Pol θ polymerase sequence to give said polymerase an increased ability to incorporate rate reversible terminator modified nucleotides, can target any other Pol θ polymerase sequence. In further particular aspect of the present invention, previously describe mutations or combination can target any other Pol θ polymerase sequence.

In particular embodiment modified Pol θ polymerase with increased incorporation rate for reversible terminator modified nucleotides presents at least 80% identity with SEQ ID No 1, in particular at least 85%, 90% 95% 97% 98%, or 99% identity with SEQ ID No 1.

In particular embodiment, the variant is a modified Pol θ polymerase having any of the previously described mutations or combination of mutations and at least 80% identity with SEQ ID No 1, in particular at least 85% 90%, 95%, 97%, 98% or 99% identity with SEQ ID No 1.

The variants according to the present invention are described according to alteration of specific residues having their position determined by SEQ ID No 1. It will be understood that the present invention encompasses any modified Pol θ polymerase bearing identical alteration in any functionally equivalent residue.

Enzymatic Synthesis of Nucleic Acid

It is the purpose of the present invention to provide variants of Family A polymerases that may be used for the synthesis of nucleic acid. More particularly, it is the purpose of the present invention to provide variants of Family A polymerases suitable to add reversible terminator modified nucleotides to an initiating nucleic acid strand. The blocking group may be then removed for allowing a new addition of reversible terminator modified nucleotide.

According to the invention, by use of a variant of the invention, it is possible to implement successive cycle comprising addition and deprotections This process will therefore allow by multiple cycles of addition of a reversible terminator modified nucleotide and further removal of the blocking group to allow the controlled extension of an initiating nucleic acid strand into a defined sequence.

The present invention contemplates the use of modified Family A polymerase according to the present invention in any enzymatic nucleic acid synthesis process. In a particular aspect of the invention the modified Family A polymerase is Pol θ polymerase.

It is also the purpose of the present invention to provide a process for synthesizing a nucleic acid molecule without template, comprising a step of contacting a nucleic acid primer with both at least one nucleotide, preferably at least one 3'O-modified nucleotide, and a variant of the invention.

The present invention contemplates the concept of enzymatic nucleic acids process. In such process, nucleic acids molecules are de novo synthesized in absence of any template strand. Accordingly, ordered sequence of nucleotides are coupled to an initiator nucleic acid fragment with the help of the variant of the invention. It will be understood that quantitative coupling and more generally high coupling efficiency of each nucleotides to the growing nucleic acid chain is of great importance. It also will be understood that non terminator nucleotides such as natural nucleotides or permanent labeled nucleotides will not permit any control over the sequence synthesized and by resulting for example in uncontrolled and undesired poly-additions.

According to a particular embodiment, the enzymatic nucleic acid process comprises:
a. Providing a nucleic acid molecule linked to a solid support;
b. Reacting previous nucleic acid molecule with a reversible terminator modified nucleotide and a modified A Family polymerase according to the present invention;

According to another particular embodiment, the enzymatic nucleic acid process comprises:
a. Providing a nucleic acid molecule linked to a solid support;
b. Adding a reversible terminator modified nucleotide and a modified A Family polymerase according to the present invention;
c. First removing of one or several reagents from the solid support;
d. Reacting the reversible moiety of the reversible terminator modified nucleotide in order to deprotect it for further subsequent elongation;
e. Second removing of one or several reagents from the solid support;
f. Optionally and finally cleaving the nucleic acid molecule from the solid support.

According to another particular embodiment, the enzymatic nucleic acid process comprise cycles subdivided in the following way:
a. a phase of elongation of Xi nucleotides to one end of said fragments, it being possible for X to be between 1 and 5, preferably between: 1 and 3, i being the number of the cycle, making it possible to obtain fragments comprising n+Xi nucleotides, known as first phase, and comprising the following stages:
  a first stage of attaching, to a first support, a first end of initial nucleic acid fragments or nucleic acid fragments in the course of elongation, including n nucleotides,
  a stage of addition of the reagents necessary for the modified A Family polymerase according to the present invention addition,
  a stage of modified A Family polymerase according to the present invention addition of Xi nucleotides to the second end of said nucleic acid fragments, it being possible for X to be between 1 and 5, preferably 1 and 3, i being the number of the cycle,
  an optional stage of removal of the undesirable reagents from the reaction medium,—a stage of detaching, from said first support, said fragments comprising n+Xi nucleotides,
  a first stage of transfer of said fragments comprising n+Xi nucleotides,
b. a phase of purification of the fragments having a correct sequence comprising n+Xi nucleotides, known as second phase, comprising the following successive stages:
  a second stage of attaching, to a second support, said fragments comprising n+Xi nucleotides by their end carrying the Xi nucleotides added during the first phase,
  a stage of removal of the fragments which have not been added to and of the fragments which have not been attached to the second support,
  a stage of detaching said fragments comprising n+Xi nucleotides from said second support,
  an optional stage of removal, from the reaction medium, of the undesirable residual reagents;
c. an optional phase of amplification, preferably enzymatic amplification, such as by PCR, of the fragments having a correct sequence comprising n+Xi nucleotides, known as third phase, comprising the following successive stages:
  a stage of addition of the reagents necessary for the amplification,
  a stage (optionally composed of substages making the process possible) of multiplication by a multiplication factor Yi of the fragments comprising n+Xi nucleotides, i being the cycle number, it being possible for Y to be between 1 and $4 \times 10^{10}$, preferably between 1 and $1 \times 10^9$,
  a stage of transfer of the fragments comprising n+Xi nucleotides,
each cycle being carried out in a reaction medium compatible with an enzymatic addition and an enzymatic amplification, such as an aqueous medium, the synthesis process also comprising, at the end of all of the i elongation cycles, a stage of final amplification by a multiplication factor Yf.

In the context of the invention, the expression "cleaving reaction" refers to any action of substance or physical conditions, which is able to cleave the additional group previously described on reversible terminator nucleotides. A person skilled in the art is able to determine a cleaving reaction for any previously listed group.

In one embodiment, the cleaving agent is a chemical cleaving agent. In an alternative embodiment, the cleaving agent is an enzymatic cleaving agent.

It will be understood by the person skilled in the art that the selection of cleaving agent is dependent on the type of 3'-nucleotide blocking group used. For example, tris(2-carboxyethyl)phosphine (TCEP) can be used to cleave a 3'O-azidomethyl groups, palladium complexes can be used to cleave a 3'O-allyl groups, or sodium nitrite can be used to cleave a 3'O-amino groups. In particular embodiment, the cleaving reaction is involving: TCEP, a palladium complex or sodium nitrite.

In particular embodiment, the cleaving reaction is performed in the presence of additional components such as denaturant (urea, guanidinium chloride, formamide or betaine for example). In a further embodiment, the cleavage reaction is performed with one or more buffers. It will be understood by the person skilled in the art that the choice of buffer is dependent on the exact mechanism of reaction.

The present invention relates to modified A Family polymerases with the capacity to incorporate in a quantitative way reversible terminator modified nucleotides. In a particular aspect, the invention related to Pol θ polymerase with the capacity to incorporate in a quantitative way reversible terminator modified nucleotides.

By "quantitative way" or "quantitative reaction", it is meant a reaction that goes to completion, wherein the reactants are totally converted into the product.

Polymerase that incorporates in a quantitative way reversible terminator nucleotide is a polymerase able to elongate every fragments of nucleic acid with all the nucleotides available leading to the conversion of all the starting fragments of length n to fragment of length n+1.

Initiating Fragments and Solid Support

As used herein, "initiating fragment" refers to a short oligonucleotide sequence with a free 3'-end, which can be further elongated. In one embodiment, the initiating fragment is a DNA initiating fragment. In an alternative embodiment, the initiating fragment is an RNA initiating fragment.

In one embodiment, the initiating fragment possesses between 3 and 100 nucleotides, in particular between 3 and 20 nucleotides.

In one embodiment, the initiating fragment is single-stranded. In an alternative embodiment, the initiating fragment is double-stranded.

In one embodiment, the initiating fragment is immobilized on a solid support. The initiating fragment may be attached with various method to a solid support resulting in a stable under the various enzymatic or synthesis reaction conditions that the fragment will undergo.

In one embodiment, the initiating fragment is immobilized on a solid support via a reversible interacting moiety, such as a chemically-cleavable linker, an antibody/immunogenic epitope, a biotin/biotin binding protein or glutathione-GST tag. In a further embodiment, the initiating fragment is immobilized on a solid support via a chemically-cleavable linker, such as a disulfide, allyl, or azide-masked hemiaminal ether linker.

In an initiating fragment, the immobilized part contains at least one restriction site. The use of restriction enzymes and restriction sites to selectively hydrolyze nucleic acids chain at a specific site is describe in the literature. Any skilled person will be able to choose the appropriate restriction enzyme that will match the initiating fragment cleaving site sequence.

In an alternative embodiment, the initiating fragment contains at least one uridine. Treatment with uracil-DNA glycosylase (UDG) generates an abasic site. Treatment on an appropriate substrate with an apurinic/apyrimidinic (AP) site endonuclease will extract the nucleic acid strand.

Nucleic Acid Molecules

It is also the purpose of the invention to provide a nucleic acid molecule encoding a variant of the invention. As used herein, a "nucleic acid molecule" refers to a polymer of nucleosides. In one embodiment, the nucleic acid is a DNA. In an alternative embodiment, the nucleic acid is RNA. In an alternative embodiment, the nucleic acid is XNA.

It will be understood by a skilled person that each of the previously listed nucleic acid molecule could beat modification on the bases of the nucleotides that constitute the polymeric molecule. Such modifications could be natural modification, such as epigenetic modifications or unnatural modification such as labels.

In one embodiment, nucleic acid molecules are DNA, RNA or XNA bearing naturally occurring epigenetic modifications such as methylation, hydfroxymethylation, formylation or 5-carboxylation.

In one embodiment, nucleic acid molecules are DNA, RNA or XNA bearing unnaturally occurring modifications such as fluorescent tag, fluorescent label and/or interaction groups.

In one embodiment, nucleic acid molecules are polymeric molecules having length of more than 50, 100, 200, 300, 400, 500, 600, 700, 800, 900, 1 000, 2 000, 3 000, 4 000, 5 000, 6 000, 7 000, 8 000, 9 000, 10 000, 15 000, 20 000, 30 000, 40 000, 50 000 or 100 000 nucleotides.

Applications

Described herein is the use of variant of a DNA polymerase of family A to be used for nucleic acid synthesis, oligonucleotide synthesis, probe synthesis, nucleic acid amplification, aptamers, therapeutic nucleic acid molecules, drug target discovery and validation, disease diagnosis, metabolic engineering, data storage, crops improvement, library design, sequencing pools, nucleic acid labeling or attachment or any other application that is involving nucleic acid molecules.

Kits, Enzyme and Nucleotide Composition

A particular aspect of the invention is relative to the composition and the use of kits comprising a modified A Family polymerase according to the invention, or to any particular aspect of the present invention, with optionally any combination of one or more components selected from: an initiating fragment, one or more reversible terminator nucleotides, additional enzyme and reagents used in a cleaving reaction. Said kits can be used in a method of enzymatic nucleic acid synthesis.

The present invention covers the composition of matter comprising modified A Family DNA polymerase according to the invention, or to any particular aspect of the present invention, with reversible terminator modified nucleotide in a mix with appropriate buffer and ratio concentration.

EXAMPLES

Example 1—Generation, Expression and Purification of Modified A Family Polymerase According to the Invention Expression Strain Generation The gene coding for the polymerase domain plus a fragment of the central domain (amino acid 1792 to 2590), ie SEQ 2, has been ordered as a synthetic gene from IDT provider (https://eu.idtdna.com/pages/products/genes/custom-gene-synthesis) with an optimization of the codon sequence for subsequent expression in *E. coli*, resulting in DNA SEQ 19. Through standard restriction ligation techniques, it has been cloned into Champion pET SUMO vector (thermofisher cat. K30001). The resulting vector is named pSUMO-THETA. The pSUMO-THETA vector has been transformed in commercial *E. coli* strain BL21-DE3 (Novagen). Colonies capable of growing on kanamycin LB-agar plates have been isolated for subsequent plasmid extraction. Extracted plasmids have been sent to sequencing using the following primers:

```
T7-pro: TAATACGACTCACTATAGGG        (SEQ ID No 7)

T7-ter: GCTAGTTATTGCTCAGCGG         (SEQ ID No 8)
```

Correct clones are name Ec-PolTheta

Polymerase Variants Generation

The pSUMO-THETA vector is used as starting vector. Specific primers comprising one or several point mutations have been generated from Agilent online software (http://www.genomics.agilent.com:80/primerDesignProgram.jsp). The commercial available kit QuickChange II (Agilent) has been used to generate the desire modified polymerases comprising the target mutations. Experimental procedures have followed the supplier's protocol. The resulting plasmids coding for the DSi variants are named pSUMO-DSi, wherein i is the variant number given in Table 9. After generation of the different pSUMO-DSi vectors, each of them have been sequenced. Vectors with the correct sequence have been transformed in E. coli producer strains, as described before. Clones able to grow on kanamycin LB-agar plates were isolated and name Ec-DSi.

Expression

The Ec-PolTheta and Ec-DSi strains have been used for inoculating 250 mL erlens with 50 mL of LB media supplemented with appropriate amount of kanamycin. After overnight growth at 37° C., appropriate volumes of these precultures have been used to inoculate 5 L erlens with 2 L LB media with kanamycin. The initial OD for the 5 L cultures was chosen to be 0.01. The erlens were put at 37° C. under strong agitation and the OD of the different cultures were regularly checked. After reaching an OD comprised between 0.6 and 0.9, each erlen was supplemented by the addition of 1 mL of 1M IPTG (Isopropyl β-D-1-thiogalactopyranoside, Sigma). The erlens were putting back to agitation under a controlled temperature of 30° C. After overnight expression, the cells were harvested in several pellets. Pellets expressing the same variants were pooled and stored at −20° C., eventually for several months.

Extraction

Previously prepared pellets were thaw in 30 to 37° C. water bath. Once fully thawed, pellets were resuspended in lysis buffer composed of 50 mM tris-HCL (Sigma) pH 7.5, 150 mM NaCl (Sigma), 0.5 mM mercaptoethanol (Sigma), 5% glycerol (Sigma), 20 mM imidazole (Sigma) and 1 tab for 100 mL of protease cocktail inhibitor (Thermofisher). Careful resuspension was carried out in order to avoid premature lysis and remaining of aggregates. Resuspended cells were lysed through several cycles of French press, until full color homogeneity was obtained. Usual pressure used was 14,000 psi. Lysate was then centrifuge for 1 h to 1 h30 at 10,000 rpm. Centrifugate was pass through a 0.2 μm filter to remove any debris before column purification.

Purification

A two-step affinity procedure was used to purify the produced and extracted polymerase enzymes. For the first step a Ni-NTA affinity column (GE Healthcare) was used to bind the polymerases. Initially the column has been washed and equilibrated with 15 column volumes of 50 mM tris-HCL (Sigma) pH 7.5, 150 mM NaCl (Sigma), 0.5 mM 2-mercaptoethanol (Sigma), 5% glycerol (Sigma) and 20 mM imidazole (Sigma). Polymerases were bond to the column after equilibration. Then a washing buffer, composed of 50 mM tris-HCL (Sigma) pH 7.5, 500 mM NaCl (Sigma), 0.5 mM 2-mercaptoethanol (Sigma), 5% glycerol (Sigma) and 20 mM imidazole (Sigma), was apply to the column for 15 column volumes. After wash the polymerases were eluted with 50 mM tris-HCL (Sigma) pH 7.5, 500 mM NaCl (Sigma), 0.5 mM mercaptoethanol (Sigma), 5% glycerol (Sigma) and 0.5M imidazole (Sigma). Fraction corresponding to the highest concentration of polymerases of interest were collected and pooled in a single sample. For the second step a Fast Desalt HR column (GE Healthcare) was used to change the buffer of the samples. The column was first washed and equilibrated with 25 Mm potassium phosphate pH 7.5 (Sigma), 10% (v/v) glycerol (Sigma), 1 mM EDTA (Sigma), 1 mM 2-mercaptoethanol (Sigma) and 75 mM KCl (Sigma). Samples were applied to the column. Then the previously used buffer was applied with a gradient of 0.075 to 0.5M of KCl. Fraction corresponding to the highest concentration of polymerases of interest were collected and pooled to give the final preparation. Small aliquots of this preparation were then flash frozen in liquid nitrogen and stored for long term at −20° C.

Example 2—Three-Dimensional Study of Modified Family A Polymerase According to the Invention Structural analysis of Pol θ polymerase is giving critical information for rational modifications in particular substitution mutations.

Different Pol θ polymerases structures has been found on the PDB (www.rcsb.org/pdb/home/home.do) and analyzed through specific interactive visualization software Chimera (https://www.cgl.ucsf.edu/chimera/).

Distance analysis of residues inside the catalytic pocket is shown in FIG. 1.

Example 3—Activity of the Modified Family A Polymerase According to the Invention Activity of the various mutant generated, expressed and purified according to example 1 is evaluated through the following assay. All the results are compared among themselves in addition to the wild type pol theta and to a control tube lacking any polymerase enzyme.

TABLE 10

| Activity test | | |
| --- | --- | --- |
| Reagent | Concentration | Volume |
| $H_2O$ | — | 2 μL |
| HEPES pH 7.5 | 250 mM | 1 μL |
| 2-mercaptoethanol | 20 mM | 1 μL |
| EDTA | 1 mM | 1 μL |
| MnCl2 | 50 mM | 1 μL |
| BSA | 500 μg/mL | 1 μL |
| dNTP | 1 mM | 1 μL |
| Purified pol theta | 50 μM | 1 μL |
| [$^{32}$P]-primer | 500 nM | 1 μL |

Primer used was the following:

```
                                    (SEQ ID No 9)
5'-AAAAAAAAAAAAAAGGGG-3'
```

It has been initially labeled with [γ-$^{32}$P]-ATP following a DNA labeling standard procedure.

Nucleotides used (noted as dNTP in table 11) are 3'-O-amino-2',3'-dideoxynucleotides-5'-triphosphate (ONH2, Firebird Biosciences) or 3'-biot-EDA-2',3'-dideoxynucleotides-5'-triphosphate (Biot-EDA, Jena Biosciences), such as 3'-O-amino-2',3'-dideoxyadenosine-5'-triphosphate or 3'-biot-EDA-2',3'-dideoxyadenosine-5'-triphosphate for example.

For each different mutant tested, one tube was used for the reaction. The reagents were added in the tube starting from the water and then in the order of Table 10. After 30 min at 37° C. the reaction was stopped by addition of formamide (Sigma).

Gel Analysis

Sample from activity test has been analyzed through polyacrylamide 16% (biorad) denaturing gel. Gel were made just before the analysis by pouring polyacrylamide inside glass plates and let it polymerizes. The gel inside the glass plates was mounted on an adapted tank filed with TBE buffer (Sigma) for the electrophoresis step. The samples to analyze were loaded on the top of the gel.

A tension of 500 to 2,000V was applied between the top and bottom of the gel for 3 to 6 h at room temperature. Once migrated according to the sample target size, system was dismantled and gel was carefully extracted from the glass plate. The gel was then placed in an incubation cassette with a phosphorous screen (Amersham) and incubated for 10 to 60 min before phosphorescence scan through the use of Typhoon instrument (GE Life Sciences).

Figure 2:
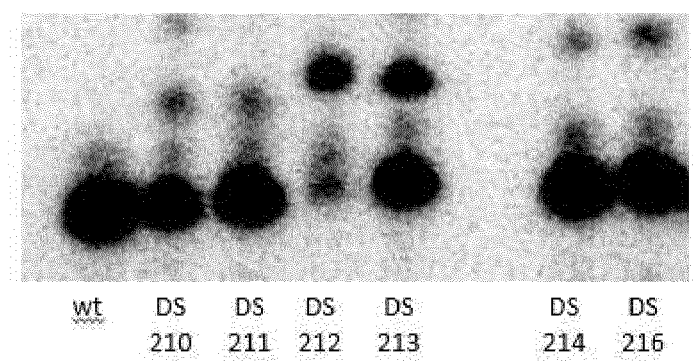
FIG. 2: Elongation assay comparing performances of wild type SEQ2 Pol θ with modified Pol θ enzymes with mutations given by table 10. The assay involves 5' radio labeled primers and 3'-O-amino reversible terminator modified nucleotides: 3'-O-amino-2',3'-dideoxyadenosine-5'-triphosphate. The picture represents a polyacrylamide gel migration of the results of the elongation assay.
Figure 3:
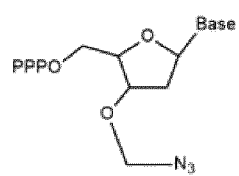
FIG. 3: Example of structure of reversible terminator modified nucleotides. The base moiety could either represent adenine, guanine, cytosine or thymine if natural deoxynucleotides are considered or any other base found in natural of synthetic nucleotides. The OPPP moiety represents the triphosphate group.
Figure 3:
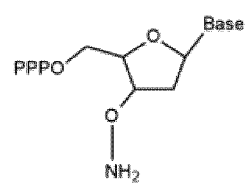
Figure 3:
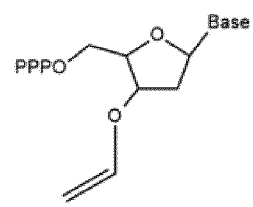
Figure 4:
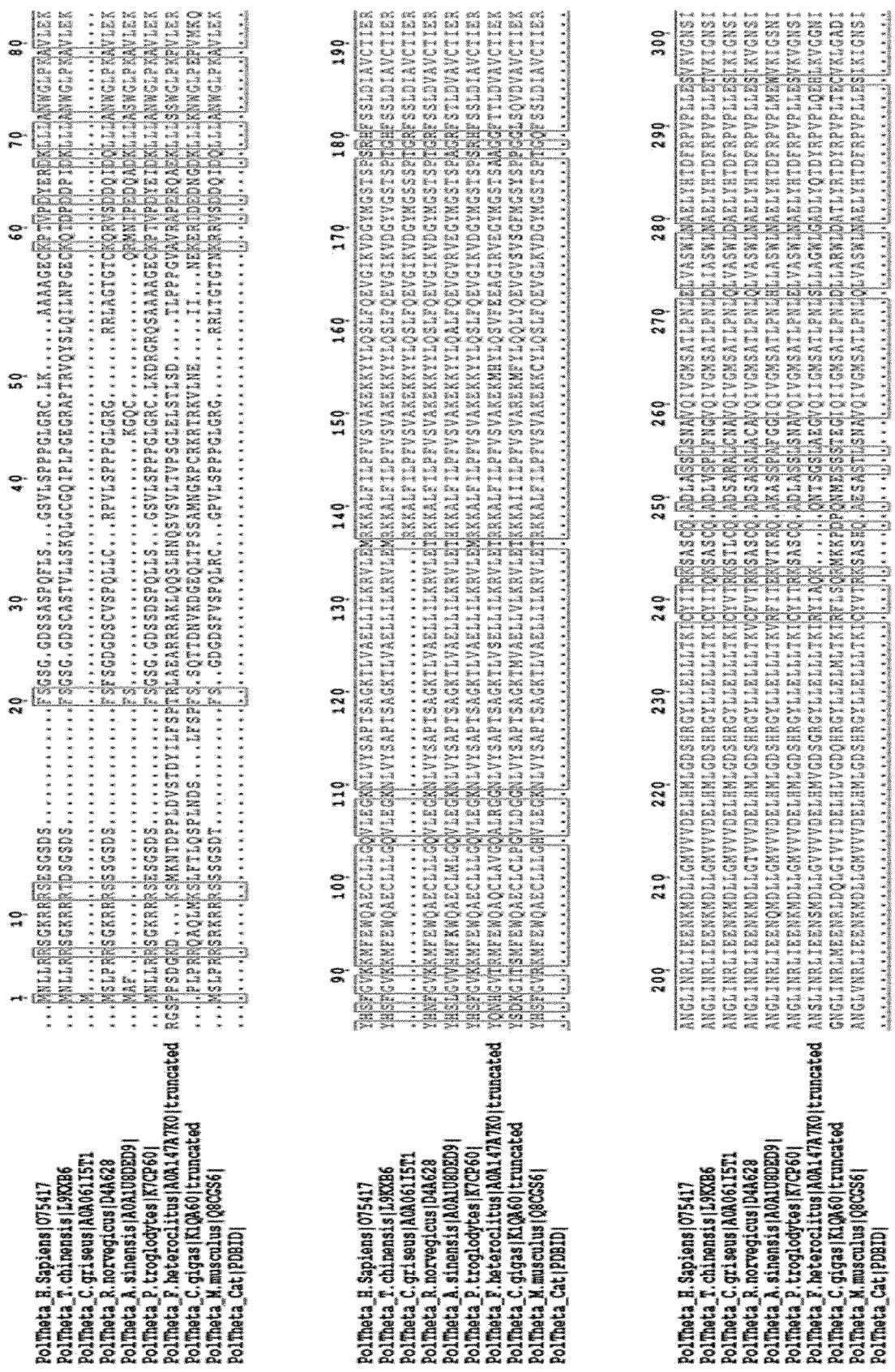
FIG. 4: Amino acid alignment of various Pol θ polymerase: *H. sapiens* (UniProtKB O75417 SEQ ID No 1), *T. chinensis* (UniProtKB L9KXB6 SEQ ID No 11), *C. griseus* (UniProtKB A0A06115T1 SEQ ID No 12), *R. norvegicus* (UniProtKB D4A628 SEQ ID No 13), *A. sinensis* (UniProtKB A0A1U8DED9 SEQ ID No 14), *P. troglodytes* (UniProtKB K7CP60 SEQ ID No 15), *F. heteroclitus* (UniProtKB A0A147A7K0 SEQ ID No 16), *C. gigas* (UniProtKB K1QA60 SEQ ID No 17), *M. musculus* (UniProtKB Q8CGS6 SEQ ID No 18) and *H. sapiens* (partially—SEQ ID No 2).
Figure 4:
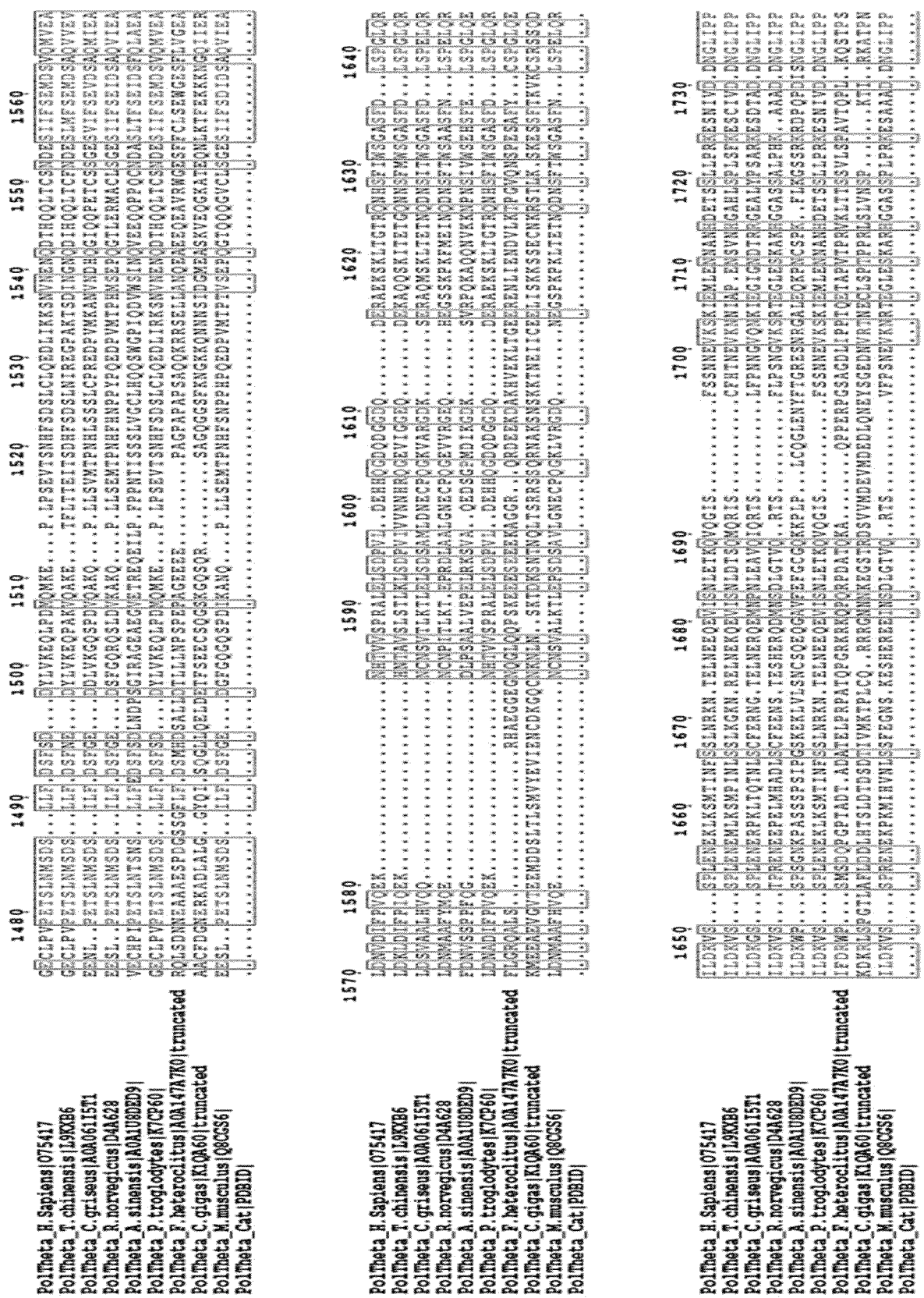
Figure 4:
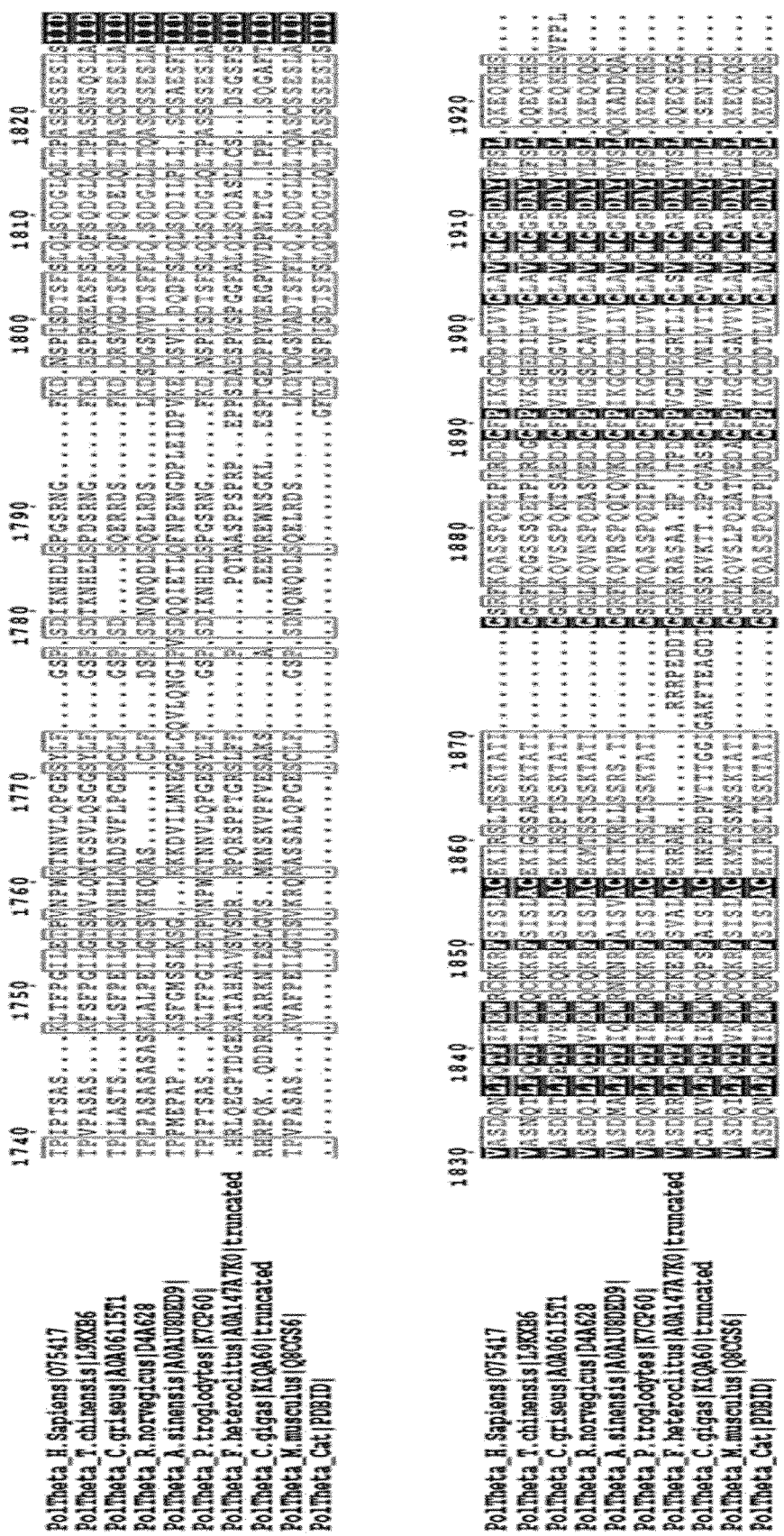
Figure 4:
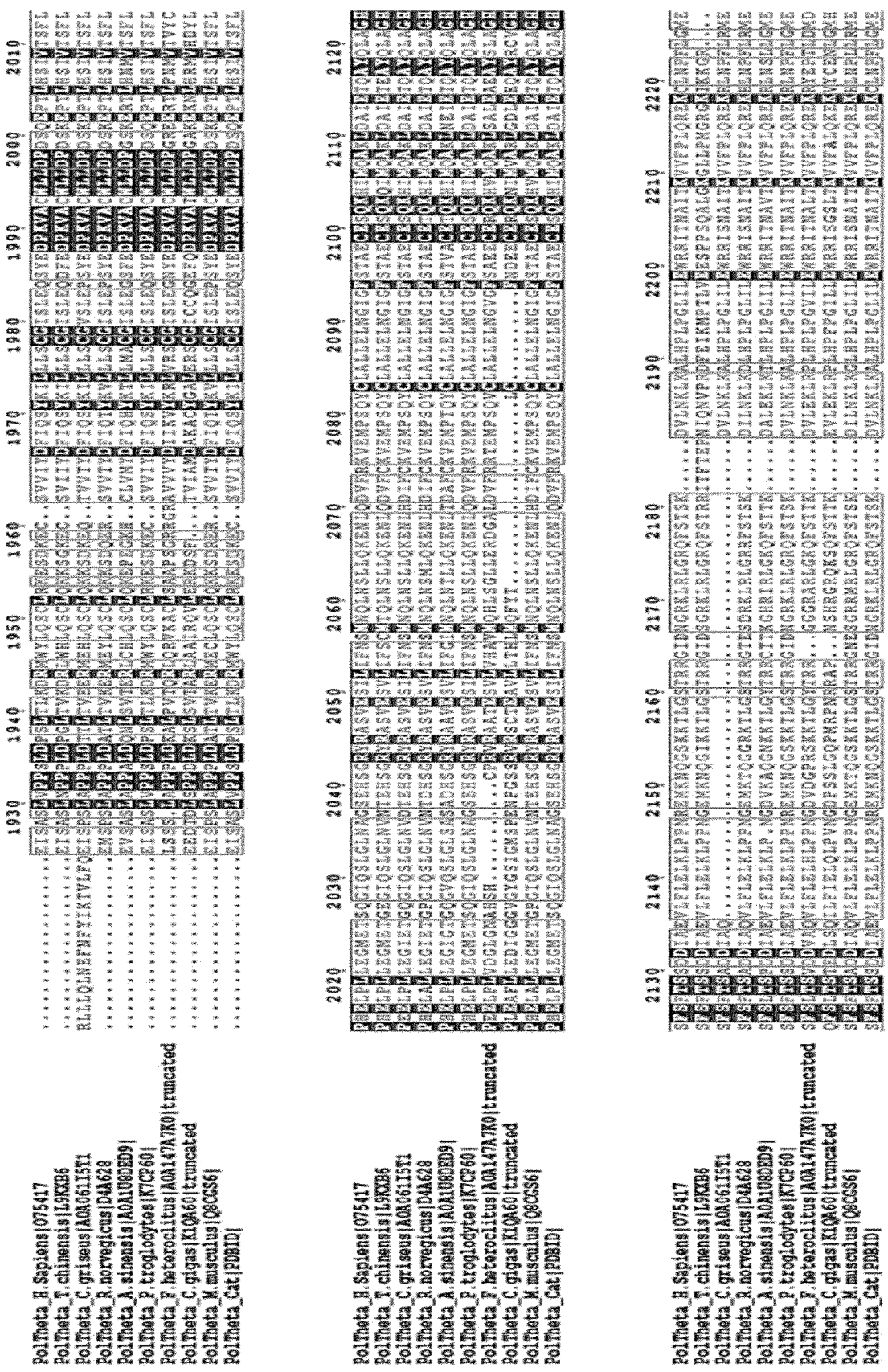
Figure 4:
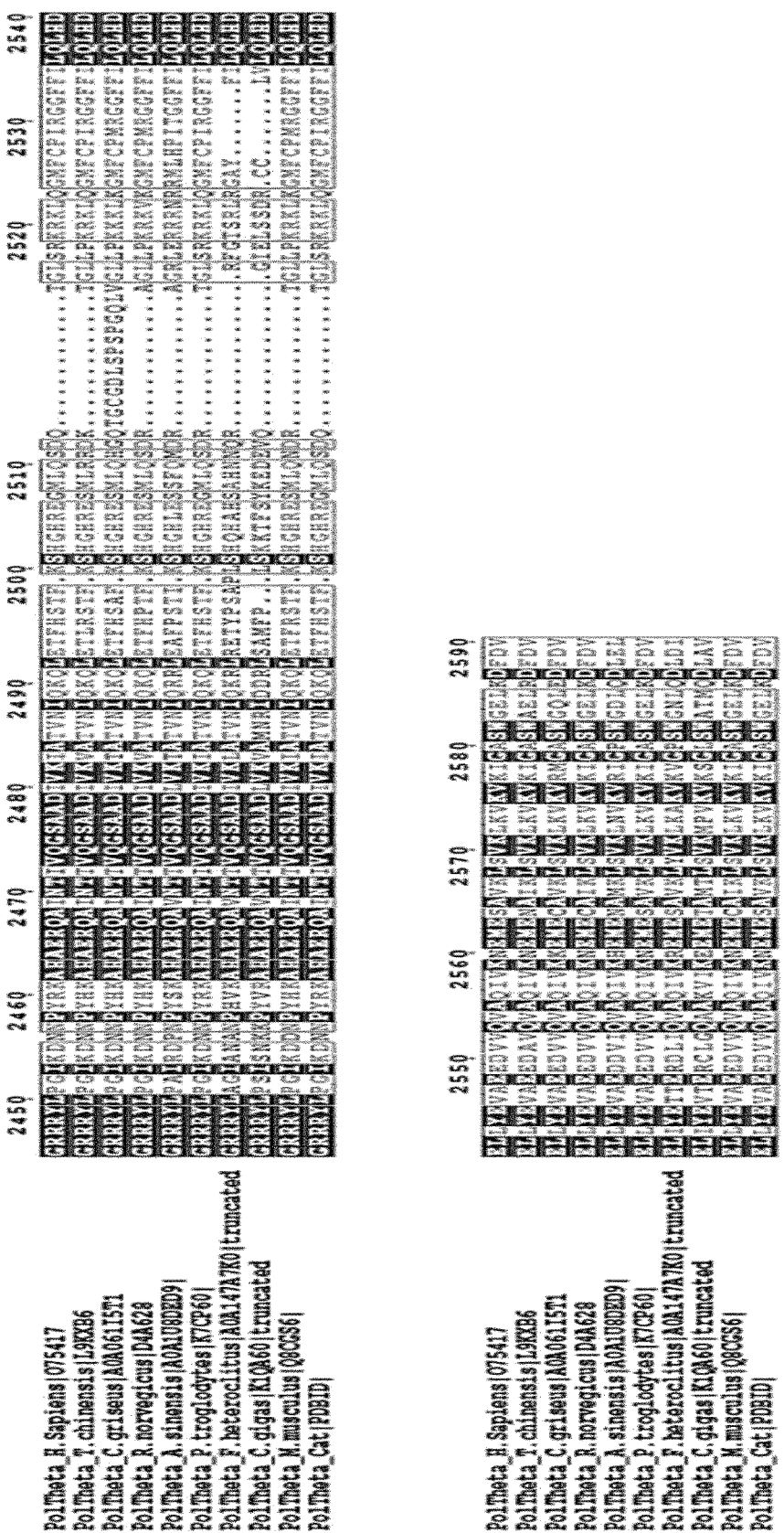

Results are showed on FIG. 2.

The invention claimed is:

1. A DNA polymerase theta variant comprising an amino acid sequence having at least 90% identity to the amino acid sequence set forth in SEQ ID NO:02, wherein the DNA polymerase theta variant comprises an amino acid sequence having at least one substitution or a combination of substitutions selected from:

L2336A, A2328V, Y2387F, E2335G, P2322A, and L2334M;
L2336A, A2328V, Y2387F, E2335G, P2322A, and L2334G;
L2336A, A2328V, Y2387F, E2335G, and P2322A;
L2336A, A2328V, Y2387F, E2335G, P2322V, and L2334M;
L2336A, A2328V, Y2387F, E2335G, P2322V, and L2334G;
L2336A, A2328V, Y2387F, E2335G, and P2322V;
L2336A, A2328V, Y2387F, E2335G, and L2334M;
L2336A, A2328V, Y2387F, E2335G, and L2334G;
L2336A, A2328V, Y2387F, E2335A, P2322A, and L2334M;
L2336A, A2328V, Y2387F, E2335A, P2322A, and L2334G;
L2336A, A2328V, Y2387F, E2335A, and P2322A;
L2336A, A2328V, Y2387F, E2335A, P2322V, and L2334M;
L2336A, A2328V, Y2387F, E2335A, P2322V, and L2334G;
L2336A, A2328V, Y2387F, E2335A, and P2322V;
L2336A, A2328V, Y2387F, E2335A, and L2334M;
L2336A, A2328V, Y2387F, E2335A, and L2334G;
L2336A, A2328V, Y2387F, P2322A, and L2334M;
L2336A, A2328V, Y2387F, P2322A, and L2334G;
L2336A, A2328V, Y2387F, and P2322A;
L2336A, A2328V, Y2387F, P2322V, and L2334M;
L2336A, A2328V, Y2387F, P2322V, and L2334G;
L2336A, A2328V, Y2387F, and P2322V;
L2336A, A2328V, Y2387F, and L2334M;
L2336A, A2328V, Y2387F, and L2334G;
L2336A, A2328V, E2335G, P2322A, and L2334M;
L2336A, A2328V, E2335G, P2322A, and L2334G;
L2336A, A2328V, E2335G, and P2322A;
L2336A, A2328V, E2335G, P2322V, and L2334M;
L2336A, A2328V, E2335G, P2322V, and L2334G;
L2336A, A2328V, E2335G, and P2322V;
L2336A, A2328V, E2335G, and L2334M;
L2336A, A2328V, E2335G, and L2334G;
L2336A, A2328V, E2335A, P2322A, and L2334M;
L2336A, A2328V, E2335A, P2322A, and L2334G;
L2336A, A2328V, E2335A, and P2322A;
L2336A, A2328V, E2335A, P2322V, and L2334M;
L2336A, A2328V, E2335A, P2322V, and L2334G;
L2336A, A2328V, E2335A, and P2322V;
L2336A, A2328V, E2335A, and L2334M;
L2336A, A2328V, E2335A, and L2334G;
L2336A, A2328V, P2322A, and L2334M;
L2336A, A2328V, P2322A, and L2334G;
L2336A, A2328V, and P2322A;
L2336A, A2328V, P2322V, and L2334M;
L2336A, A2328V, P2322V, and L2334G;
L2336A, A2328V, and P2322V;
L2336A, A2328V, and L2334M;
L2336A, A2328V, and L2334G;
L2336A, Y2387F, E2335G, P2322A, and L2334M;
L2336A, Y2387F, E2335G, P2322A, and L2334G;
L2336A, Y2387F, E2335G, and P2322A;
L2336A, Y2387F, E2335G, P2322V, and L2334M;
L2336A, Y2387F, E2335G, P2322V, and L2334G;
L2336A, Y2387F, E2335G, and P2322V;
L2336A, Y2387F, E2335G, and L2334M;
L2336A, Y2387F, E2335G, and L2334G;
L2336A, Y2387F, E2335A, P2322A, and L2334M;
L2336A, Y2387F, E2335A, P2322A, and L2334G;
L2336A, Y2387F, E2335A, and P2322A;
L2336A, Y2387F, E2335A, P2322V, and L2334M;
L2336A, Y2387F, E2335A, P2322V, and L2334G;
L2336A, Y2387F, E2335A, and P2322V;
L2336A, Y2387F, E2335A, and L2334M;
L2336A, Y2387F, E2335A, and L2334G;
L2336A, Y2387F, P2322A, and L2334M;
L2336A, Y2387F, P2322A, and L2334G;
L2336A, Y2387F, and P2322A;
L2336A, Y2387F, P2322V, and L2334M;
L2336A, Y2387F, P2322V, and L2334G;
L2336A, Y2387F, and P2322V;
L2336A, Y2387F, and L2334M;
L2336A, Y2387F, and L2334G;
L2336A, E2335G, P2322A, and L2334M;
L2336A, E2335G, P2322A, and L2334G;
L2336A, E2335G, and P2322A;
L2336A, E2335G, P2322V, and L2334M;
L2336A, E2335G, P2322V, and L2334G;
L2336A, E2335G, and P2322V;
L2336A, E2335G, and L2334M;
L2336A, E2335G, and L2334G;
L2336A, E2335A, P2322A, and L2334M;
L2336A, E2335A, P2322A, and L2334G;
L2336A, E2335A, and P2322A;
L2336A, E2335A, P2322V, and L2334M;
L2336A, E2335A, P2322V, and L2334G;
L2336A, E2335A, and P2322V;
L2336A, E2335A, and L2334M;
L2336A, E2335A, and L2334G;
L2336A, P2322A, and L2334M;
L2336A, P2322A, and L2334G;
L2336A and P2322A;

L2336A, P2322V, and L2334M;
L2336A, P2322V, and L2334G;
L2336A and P2322V;
L2336A and L2334M;
L2336A and L2334G;
A2328V, Y2387F, E2335G, P2322A, and L2334M;
A2328V, Y2387F, E2335G, P2322A, and L2334G;
A2328V, Y2387F, E2335G, and P2322A;
A2328V, Y2387F, E2335G, P2322V, and L2334M;
A2328V, Y2387F, E2335G, P2322V, and L2334G;
A2328V, Y2387F, E2335G, and P2322V;
A2328V, Y2387F, E2335G, and L2334M;
A2328V, Y2387F, E2335G, and L2334G;
A2328V, Y2387F, E2335A, P2322A, and L2334M;
A2328V, Y2387F, E2335A, P2322A, and L2334G;
A2328V, Y2387F, E2335A, and P2322A;
A2328V, Y2387F, E2335A, P2322V, and L2334M;
A2328V, Y2387F, E2335A, P2322V, and L2334G;
A2328V, Y2387F, E2335A, and P2322V;
A2328V, Y2387F, E2335A, and L2334M;
A2328V, Y2387F, E2335A, and L2334G;
A2328V, Y2387F, P2322A, and L2334M;
A2328V, Y2387F, P2322A, and L2334G;
A2328V, Y2387F, and P2322A;
A2328V, Y2387F, P2322V, and L2334M;
A2328V, Y2387F, P2322V, and L2334G;
A2328V, Y2387F, and P2322V;
A2328V, Y2387F, and L2334M;
A2328V, Y2387F, and L2334G;
A2328V, E2335G, P2322A, and L2334M;
A2328V, E2335G, P2322A, and L2334G;
A2328V, E2335G, and P2322A;
A2328V, E2335G, P2322V, and L2334M;
A2328V, E2335G, P2322V, and L2334G;
A2328V, E2335G, and P2322V;
A2328V, E2335G, and L2334M;
A2328V, E2335G, and L2334G;
A2328V, E2335A, P2322A, and L2334M;
A2328V, E2335A, P2322A, and L2334G;
A2328V, E2335A, and P2322A;
A2328V, E2335A, P2322V, and L2334M;
A2328V, E2335A, P2322V, and L2334G;
A2328V, E2335A, and P2322V;
A2328V, E2335A, and L2334M;
A2328V, E2335A, and L2334G;
A2328V, P2322A, and L2334M;
A2328V, P2322A, and L2334G;
A2328V and P2322A;
A2328V, P2322V, and L2334M;
A2328V, P2322V, and L2334G;
A2328V and P2322V;
A2328V and L2334M;
A2328V and L2334G;
Y2387F, E2335G, P2322A, and L2334M;
Y2387F, E2335G, P2322A, and L2334G;
Y2387F, E2335G, and P2322A;
Y2387F, E2335G, P2322V, and L2334M;
Y2387F, E2335G, P2322V, and L2334G;
Y2387F, E2335G, and P2322V;
Y2387F, E2335G, and L2334M;
Y2387F, E2335G, and L2334G;
Y2387F, E2335A, P2322A, and L2334M;
Y2387F, E2335A, P2322A, and L2334G;
Y2387F, E2335A, and P2322A;
Y2387F, E2335A, P2322V, and L2334M;
Y2387F, E2335A, P2322V, and L2334G;
Y2387F, E2335A, and P2322V;
Y2387F, E2335A, and L2334M;
Y2387F, E2335A, and L2334G;
Y2387F, P2322A, and L2334M;
Y2387F, P2322A, and L2334G;
Y2387F and P2322A;
Y2387F, P2322V, and L2334M;
Y2387F, P2322V, and L2334G;
Y2387F and P2322V;
Y2387F and L2334M;
Y2387F and L2334G;
E2335G, P2322A, and L2334M;
E2335G, P2322A, and L2334G;
E2335G and P2322A;
E2335G, P2322V, and L2334M;
E2335G, P2322V, and L2334G;
E2335G and P2322V;
E2335G and L2334M;
E2335G and L2334G;
E2335A, P2322A, and L2334M;
E2335A, P2322A, and L2334G;
E2335A and P2322A;
E2335A, P2322V, and L2334M;
E2335A, P2322V, and L2334G;
E2335A and P2322V;
E2335A and L2334M;
E2335A and L2334G;
P2322A and L2334M;
P2322A and L2334G;
P2322A;
P2322V and L2334M;
P2322V and L2334G;
P2322V;
L2334M; and
L2334G;
wherein the amino acid positions are numbered by reference to the amino acid sequence of SEQ ID NO:01, and amino acid positions D2330, D2540, and E2541 do not have an amino acid substitution, wherein the DNA polymerase theta variant is able to synthesize a nucleic acid fragment without a template and is able to incorporate a 3'-O-amino reversible modified terminator nucleotide into a nucleic acid fragment;
wherein the variant has an increased ability to incorporate the 3'-O-amino reversible modified terminator nucleotide into a nucleic acid fragment as compared to a DNA polymerase comprising the sequence of SEQ ID NO:01.

2. The DNA polymerase theta variant of claim 1, which has at least 95%, 97%, 98% or 99% identity to the full length amino acid sequence set forth in SEQ ID NO:01.

* * * * *